US011752172B2

(12) United States Patent
Sutlu et al.

(10) Patent No.: US 11,752,172 B2
(45) Date of Patent: Sep. 12, 2023

(54) NATURAL KILLER (NK) CELLS EXPRESSING AN ANTIGEN-SPECIFIC FUNCTIONAL T CELL RECEPTOR (TCR) COMPLEX, METHODS FOR PRODUCTION THEREOF, AND METHODS FOR THERAPEUTIC USE THEREOF

(71) Applicants: NOVA SOUTHEASTERN UNIVERSITY, Fort Lauderdale, FL (US); SABANCI ÜNIVERSITESI, Tuzla/Istanbul (TR)

(72) Inventors: Tolga Sutlu, Tuzla/Istanbul (TR); Adil Doganay Duru, Fort Lauderdale, FL (US); Batu Erman, Tuzla/Istanbul (TR)

(73) Assignees: NOVA SOUTHEASTERN UNIVERSITY, Fort Lauderdale, FL (US); SABANCI ÜNIVERSITESI, Tuzla/Istanbul (TR)

( * ) Notice: Subject to any disclaimer, the term of this patent is extended or adjusted under 35 U.S.C. 154(b) by 569 days.

(21) Appl. No.: 16/475,803

(22) PCT Filed: Jan. 4, 2018

(86) PCT No.: PCT/US2018/012403
§ 371 (c)(1),
(2) Date: Jul. 3, 2019

(87) PCT Pub. No.: WO2018/129199
PCT Pub. Date: Jul. 12, 2018

(65) Prior Publication Data
US 2019/0365812 A1 Dec. 5, 2019

Related U.S. Application Data

(60) Provisional application No. 62/442,744, filed on Jan. 5, 2017, provisional application No. 62/442,224, filed on Jan. 4, 2017.

(51) Int. Cl.
*A61K 35/17* (2015.01)
*C07K 14/725* (2006.01)

(52) U.S. Cl.
CPC .......... *A61K 35/17* (2013.01); *C07K 14/7051* (2013.01)

(58) Field of Classification Search
None
See application file for complete search history.

(56) References Cited

U.S. PATENT DOCUMENTS

| | | | |
|---|---|---|---|
| 8,697,854 B2 | 4/2014 | Schendel et al. | |
| 11,155,786 B2 * | 10/2021 | Walchli | A61K 35/17 |
| 2002/0068044 A1 | 6/2002 | Klingemann | |
| 2004/0052770 A1 | 3/2004 | Klingemann | |
| 2004/0120935 A1 | 6/2004 | Pecher | |
| 2008/0247970 A1 | 10/2008 | Campbell | |
| 2008/0247990 A1 | 10/2008 | Champbell | |
| 2014/0099714 A1 | 4/2014 | Klingemann | |

FOREIGN PATENT DOCUMENTS

| | | | |
|---|---|---|---|
| JP | 2015 223143 A | 12/2015 | |
| WO | 2008103471 A2 | 8/2008 | |
| WO | WO-2010088160 A1 * | 8/2010 | ....... G01N 33/57492 |
| WO | 2013057586 A1 | 4/2013 | |
| WO | 2014037422 A1 | 3/2014 | |
| WO | 2014145252 A2 | 9/2014 | |
| WO | 2014183056 A1 | 11/2014 | |
| WO | 2015/054299 | 4/2015 | |
| WO | 2015154012 A1 | 10/2015 | |
| WO | 2016044605 A1 | 3/2016 | |
| WO | 2016/057345 | 4/2016 | |
| WO | 2016116601 A1 | 7/2016 | |
| WO | 2016197108 A1 | 12/2016 | |

OTHER PUBLICATIONS

Phillips et al. (J Exp Med. Apr. 1, 1992;175(4):1055-66). (Year: 1992).*
Vivier et al. (J Immunol. Dec. 15, 1991;147(12):4263-70). (Year: 1991).*
Willemsen et al. (Gene Therapy (2000) 7, 1369-1377). (Year: 2000).*
Maki et al. (J Hematother Stem Cell Res. Jun. 2001;10(3):369-83). (Year: 2001).*
Robbins et al. (Clin Cancer Res; 21(5); 1019-27. 2014). (Year: 2014).*
Gros et al., Nat Med. Apr. 2016;22(4):433-8. (Year: 2016).*
Pasetto et al., Cancer Immunol Res; 4(9); 734-43. 2016. (Year: 2016).*
Parkhurst et al., Clin Cancer Res; 23(10); 2491-505. 2016. (Year: 2016).*
Lanier et al. (Nature. 1989;342(6251):803-805). (Year: 1989).*
Anderson et al. (PNAS, vol. 87, pp. 2274-2278, Mar. 1990). (Year: 1990).*
Roberts et al., Blood. 2007, 109:3198-3206. (Year: 2007).*
Npl1 IPRP International Preliminary Report and Written Opinion for PCT/US18/12403 dated Jul. 9, 2019.
European Search Report dated Nov. 10, 2020, for EP18736672.9 (10 pages).
Topfer, DAP12-Based Activating Chimeric Antigen Receptor for NK Cell Tumor Immunotherapy, Journal of Immunology, vol. 194, No. 7, p. 3201-3212, Mar. 4, 2015.

(Continued)

*Primary Examiner* — Zachary S Skelding
(74) *Attorney, Agent, or Firm* — Fleit Intellectual Property Law; Paul D. Bianco; Katharine Davis Wong

(57) ABSTRACT

The invention provides modified Natural Killer (NK) cells expressing an antigen-specific functional T cell receptor (TCR) complex. These NK cells are used for T cell receptor (TCR) gene therapy in order to circumvent any risk of mispairing of the TCR α and β chains and to provide Major Histocompatibility Complex (MHC)-restricted antigen-specific cytotoxicity to the NK cells. The invention additionally provides methods for producing the modified NK cells, therapeutic compositions including the modified NK cells, and methods for using the modified NK cells in therapy of cancer, viral infections, autoimmunity, and graft versus host disease (GvHD).

16 Claims, 53 Drawing Sheets

Specification includes a Sequence Listing.

(56) References Cited

OTHER PUBLICATIONS

Npl1 International Search Report and Written Opinion for PCT/US18/12403 dated Apr. 13, 2018.
Npl2 Jacob Nattermann et al., HIV-1 infection leads to increased HLA-E expression resulting in impaired function of natural killler cells; Antiviral Therapy 10:95-107; International Medical Press 2005.
Npl3 Paola et al., Alternations in expression and function of signal-transducing proteins in tumor-associated T and natural killer cells in patients with ovarian carcinoma; Clinical Cancer Research vol. 2 161-173, Jan. 1996.
Npl4 Valery Renard et al., Normal development and function of natural killer cells in CD3 mutant mice; Proc. Natl. Acad. Sci. USA vol. 92, pp. 7545-7549, Aug. 1995 Immunology.
Npl5 Schirrmann et al. Human natural killer cell line modified with a chimeric immunoglobulin T-cell receptor gene leads to tumor growth inhibition in vivo; Cancer Gene Theraphy (2002) 9, 390-398.
Npl6 Christoph Uherek et al., Retargeting of natural killer-cell cytolytic activity to ErbB2-expressing cancer cells results in efficient and selective tumor cell destruction; The American Society of Hematology, BLOOD, vol. 100, No. 4 pp. 1265-1275; dated Aug. 15, 2002.
Written Opinion for PCT/EP2016/051344 filed Jan. 22, 2016.
International Preliminary Report for PCT/EP2016/051344 dated Jul. 18, 2019.
Npl1 Uttenthal BJ, Chua 1I, Morris EC, Stauss HJ. Challenges in T cell receptor gene therapy. J Gene Med. Jun. 2012;14(6):386-99.
Npl2 Rosenberg SA, Dudley ME. Cancer regression in patients with metastatic melanoma after the transfer of autologous antitumor lymphocytes. Proc Natl Acad Sci USA. Oct. 5, 2004;101 Suppl 2:14639-45.
Npl3 Morgan RA, Dudley ME, Wunderlich JR, Hughes MS, Yang JC, Sherry RM, et al. Cancer regression in patients after transfer of genetically engineered lymphocytes. Science. Oct. 6, 2006;314(5796):126-9.
Npl4 Cooper LJ, Kalos M, Lewinsohn DA, Riddell SR, Greenberg PD. Transfer of specificity for human mmunodeficiency virus type 1 into primary human T lymphocytes by introduction of T-cell receptor genes. Journal of virology. Sep. 2000;74(17):8207-12.
Npl5 Rubinstein MP, Kadima AN, Salem ML, Nguyen CL, Gillanders WE, Nishimura MI, et al. Transfer of TCR genes nto mature T cells is accompanied by the maintenance of parental T cell avidity. J Immunol. Feb. 1, 2003;170 (3):1209-17.
Npl6 Govers C, Sebestyen Z, Coccoris M, Willemsen RA, Debets R. T cell receptor gene therapy: strategies for optimizing transgenic TCR pairing. Trends in molecular medicine. Feb. 2010;16(2):77-87.
Npl7 Bendle GM, Linnemann C, Hooijkaas AI, Bies L, de Witte MA, Jorritsma A, et al. Lethal graft-versus-host disease in mouse models of T cell receptor gene therapy. Nat Med. May 2010;16(5):565-70.
Npl8 Ferrara J, Reddy P, Paczesny S. Immunotherapy through T-cell receptor gene transfer induces severe graft-ersus-host disease. Immunotherapy. Nov. 2010;2(6):791-4.
Npl9 Cohen CJ, Zhao Y, Zheng Z, Rosenberg SA, Morgan RA. Enhanced antitumor activity of murine-human hybrid T-cell receptor (TCR) in human lymphocytes is associated with improved pairing and TCR/CD3 stability. Cancer Res. Sep. 1, 2006;66(17):8878-86.
Npl10 Stanislawski T, Voss RH, Lotz C, Sadovnikova E, Willemsen RA, Kuball J, et al. Circumventing tolerance to a human MDM2-derived tumor antigen by TCR gene transfer. Nat Immunol. Oct. 2001;2(10):962-70.
Npl11 Davis JL, Theoret MR, Zheng Z, Lamers CH, Rosenberg SA, Morgan RA. Development of human anti-murine T-cell receptor antibodies in both responding and nonresponding patients enrolled in TCR gene therapy trials. Clin Cancer Res. Dec. 1, 2010;16(23):5852-61.

Npl12 Kuball J, Dossett ML, Wolfl M, Ho WY, Voss RH, Fowler C, et al. Facilitating matched pairing and expression of TCR chains introduced into human T cells. Blood. Mar. 15, 2007;109(6):2331-8.
Npl13 Szymczak AL, Workman CJ, Wang Y, Vignali KM, Dilioglou S, Vanin EF, et al. Correction of multi-gene deficiency in vivo using a single 'self-cleaving' 2A peptide-based retroviral vector. Nat Biotechnol. May 2004;22 (5):589-94.
Npl14 Govers C, Sebestyen Z, Roszik J, van Brakel M, Berrevoets C, Szoor A, et al. TCRs genetically linked to CD28 and CD3epsilon do not mispair with endogenous TCR chains and mediate enhanced T cell persistence and antimelanoma activity. J Immunol. Nov. 15, 2014;193(10):5315-26.
Npl16 Tao C, Shao H, Yuan Y, Wang H, Zhang W, Zheng W, et al. Imaging of T-cell receptor fused to CD3zeta reveals enhanced expression and improved pairing in living cells. International journal of molecular medicine. Sep. 2014;34 (3):849-55.
Npl17 Vatakis DN, Arumugam B, Kim SG, Bristol G, Yang O, Zack JA. Introduction of exogenous T-cell receptors into human hematopoietic progenitors results in exclusion of endogenous T-cell receptor expression. Molecular therapy the journal of the American Society of Gene Therapy. May 2013;21(5):1055-63.
Npl18 Shao H, Zhang W, Hu Q, Wu F, Shen H, Huang S. TCR mispairing in genetically modified T cells was detected by fluorescence resonance energy transfer. Molecular biology reports. Dec. 2010;37(8):3951-6.
Npl19 Kieback E, Charo J, Sommermeyer D, Blankenstein T, Uckert W. A safeguard eliminates T cell receptor gene-modified autoreactive T cells after adoptive transfer. Proc Natl Acad Sci USA. Jan. 15, 2008;105(2):623-8.
Npl 20 Okamoto S, Mineno J, Ikeda H, Fujiwara H, Yasukawa M, Shiku H, et al. Improved expression and reactivity of transduced tumor-specific TCRs in human lymphocytes by specific silencing of endogenous TCR. Cancer Res. Dec. 1, 2009;69(23):9003-11.
Npl21 Provasi E, Genovese P, Lombardo A, Magnani Z, Liu PQ, Reik A, et al. Editing T cell specificity towards leukemia by zinc finger nucleases and lentiviral gene transfer. Nat Med. May 2012;18(5):807-15.
Npl22 CI, Sarhan D, Chrobok M, Duru AD, Alici E. Natural Killer Cell-Based Therapies Targeting Cancer: Possible Strategies to Gain and Sustain Anti-Tumor Activity. Frontiers in immunology. 2015;6:605.
Npl23 Pegram HJ, Kershaw MH, Darcy PK. Genetic modification of natural killer cells for adoptive cellular immunotherapy. Immunotherapy. Jul. 2009;1(4):623-30.
Npl24 Uherek C, Tonn T, Uherek B, Becker S, Schniede B, Klingemann HG, et al. Retargeting of natural killer-cell cytolytic activity to ErbB2-expressing cancer cells results in efficient and selective tumor cell destruction. Blood. Aug. 15, 2002;100(4):1265-73.
Npl25 Kruschinski A, Moosmann A, Poschke I, Norell H, Chmielewski M, Seliger B, et al. Engineering antigen-specific primary human NK cells against HER-2 positive carcinomas. Proc Natl Acad Sci USA. Nov. 11, 2008;105(45):17481-6.
Npl26 Lanier LL, Chang C, Spits H, Phillips JH. Expression of cytoplasmic CD3 epsilon proteins in activated human adult natural killer (NK) cells and CD3 gamma, delta, epsilon complexes in fetal NK cells. Implications for the relationship of NK and T lymphocytes. J Immunol. Sep. 15, 1992;146(6):1876-80.
Npl27 Brusko TM, Koya RC, Zhu S, Lee MR, Putnam AL, McClymont SA, et al. Human antigen-specific regulatory T cells generated by T cell receptor gene transfer. PLoS One. 2010;5(7):e11726.
Npl28 Roszkowski JJ, Yu DC, Rubinstein MP, McKee MD, Cole DJ, Nishimura MI. CD8-independent tumor cell recognition is a property of the T cell receptor and not the T cell. J Immunol. Mar. 1, 2003;170(5):2582-9.
Npl29 Alter G, Malenfant JM, Altfeld M. CD107a as a functional marker for the identification of natural killer cell activity. Journal of immunological methods. Nov. 2004;294(1-2):15-22.
Npl30 Stauss HJ, Morris EC, Abken H. Cancer gene therapy with T cell receptors and chimeric antigen receptors. Current opinion in pharmacology. Oct. 2015;24:113-8.

(56) References Cited

OTHER PUBLICATIONS

Npl31 Zhang G, Liu R, Zhu X, Wang L, Ma J, Han H, et al. Retargeting NK-92 for anti-melanoma activity by a TCR-like single-domain antibody. Immunology and cell biology. Nov.-Dec. 2013;91(10):615-24.

Npl32 Ljunggren HG, Karre K. In search of the 'missing self': MHC molecules and NK cell recognition. Immunology today. Jul. 1990;11(7):237-44.

Npl33 Maki G, Klingemann HG, Martinson JA, Tam YK. Factors regulating the cytotoxic activity of the human natural killer cell line, NK-92. Journal of hematotherapy & stem cell research. Jun. 2001;10(3):369-83.

Npl34 Carbone E, Ruggiero G, Terrazzano G, Palomba C, Manzo C, Fontana S, et al. A new mechanism of NK cell cytotoxicity activation: the CD40-CD40 ligand interaction. The Journal of experimental medicine. Jun. 16, 1997;185 (12):2053-60.

Npl35 Ehrlich. Ned Tijdschr Geneeskd. 1908; 5:273-90.

Npl36 M. Burnet et al.; Cancer A Biological Approach; Br Med. J. 1957; 1:779-86.

Npl37 L. Lanier; Natural killer cell receptor signaling; Current Opinion in Immunology 2003,15: 308-314.

\* cited by examiner

FIG. 2A
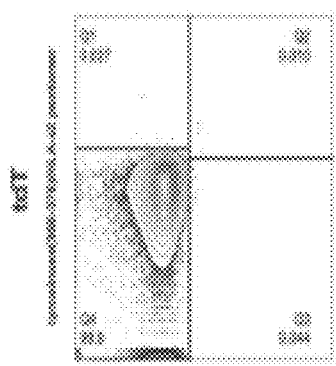
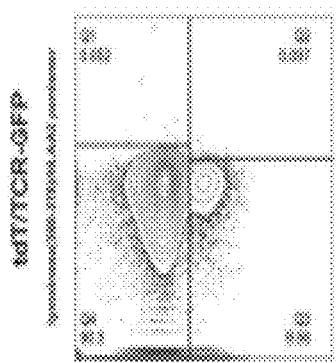
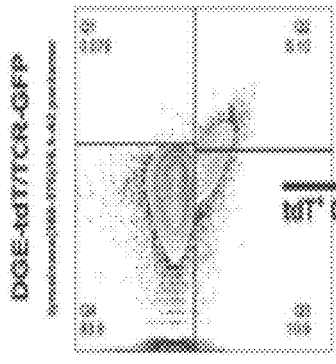
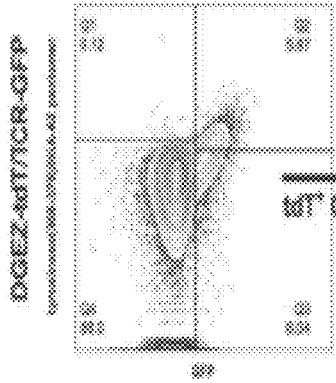
FIG. 2B
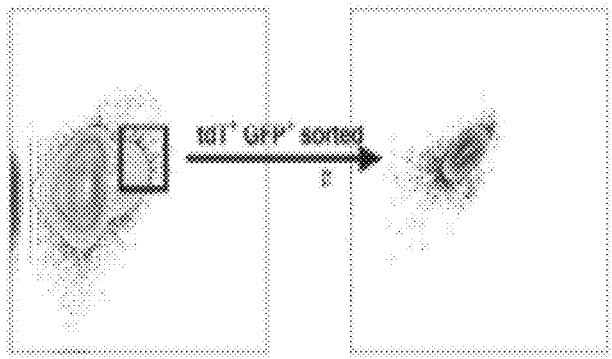
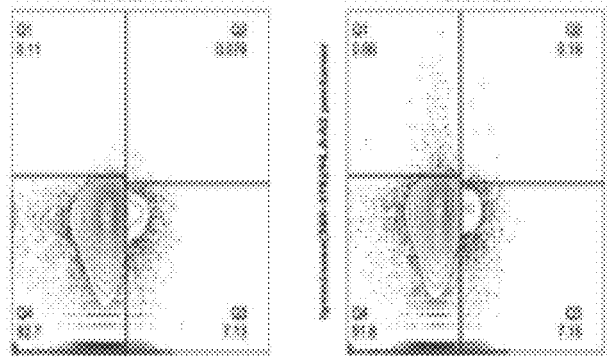
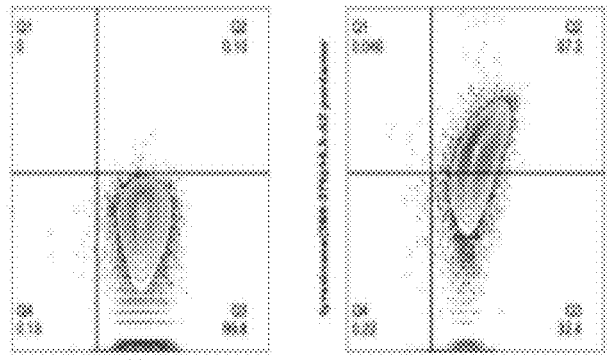
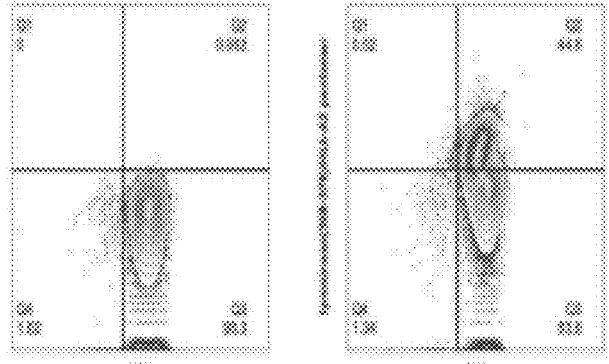
FIG. 2C

FIG. 4A
TyrTCR-IRES-eGFP (TCR)
LeGO-T2puro (tdT)
LeGO-DGE-iT2puro (DGE)
LeGO-DGEZ-iT2puro (DGEZ)
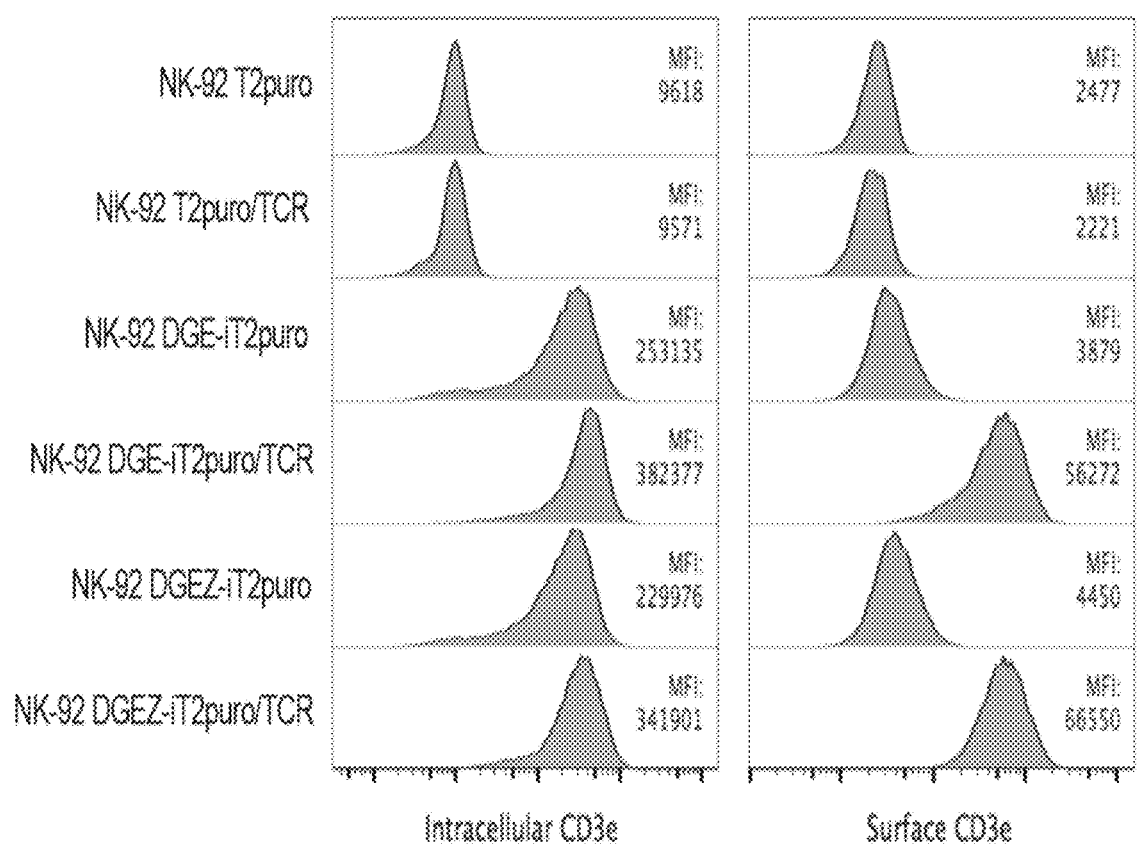
FIG. 4B

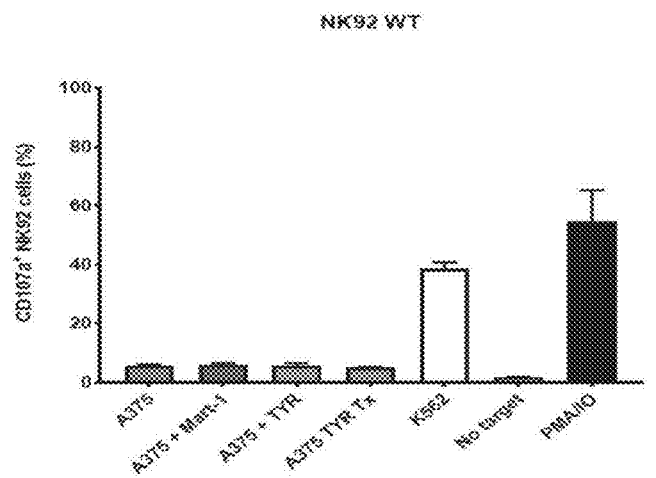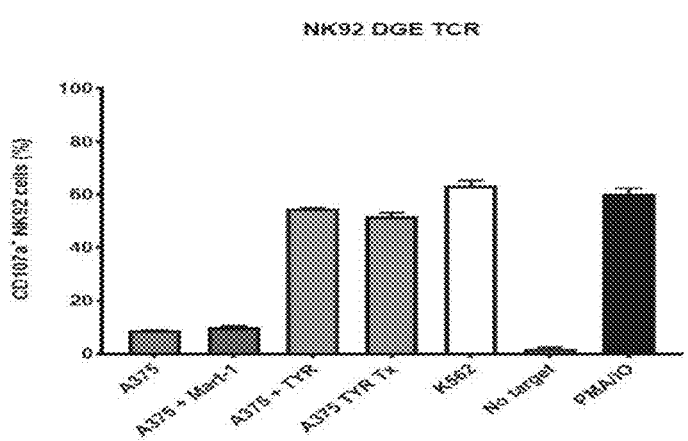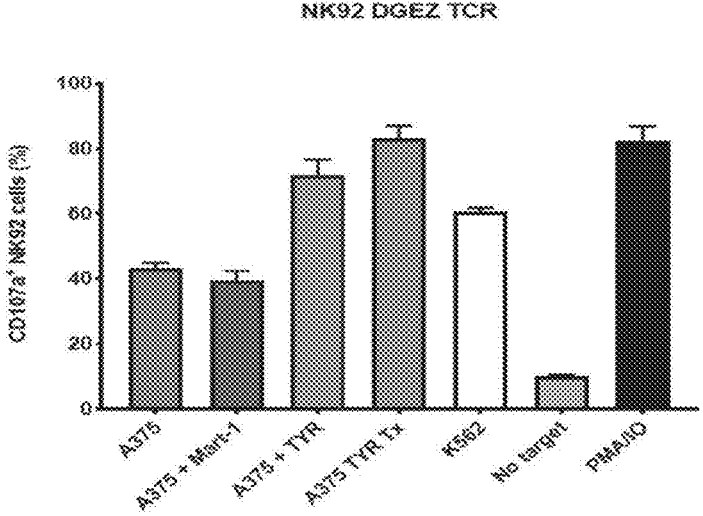

Exp 1
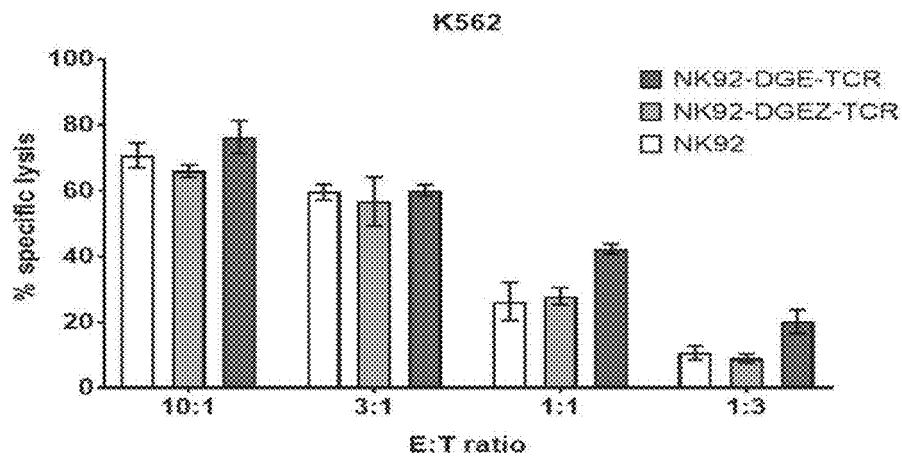
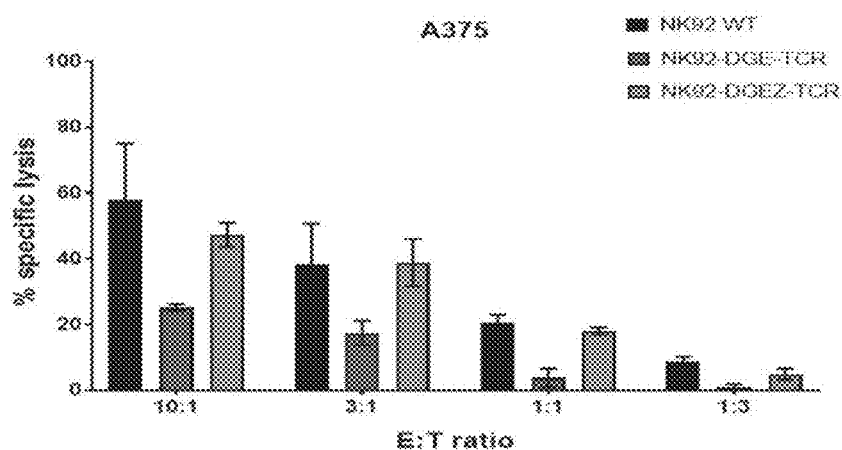
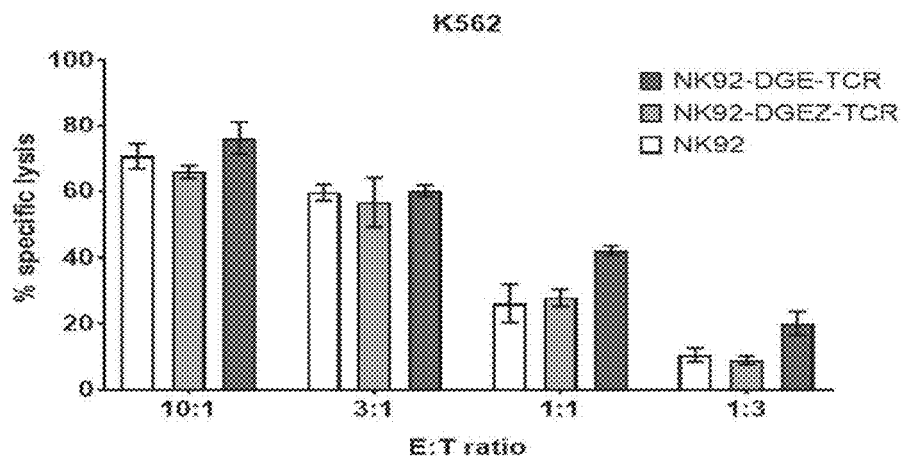
FIG. 11A

DGEZ T2 TCR

FIG. 19C
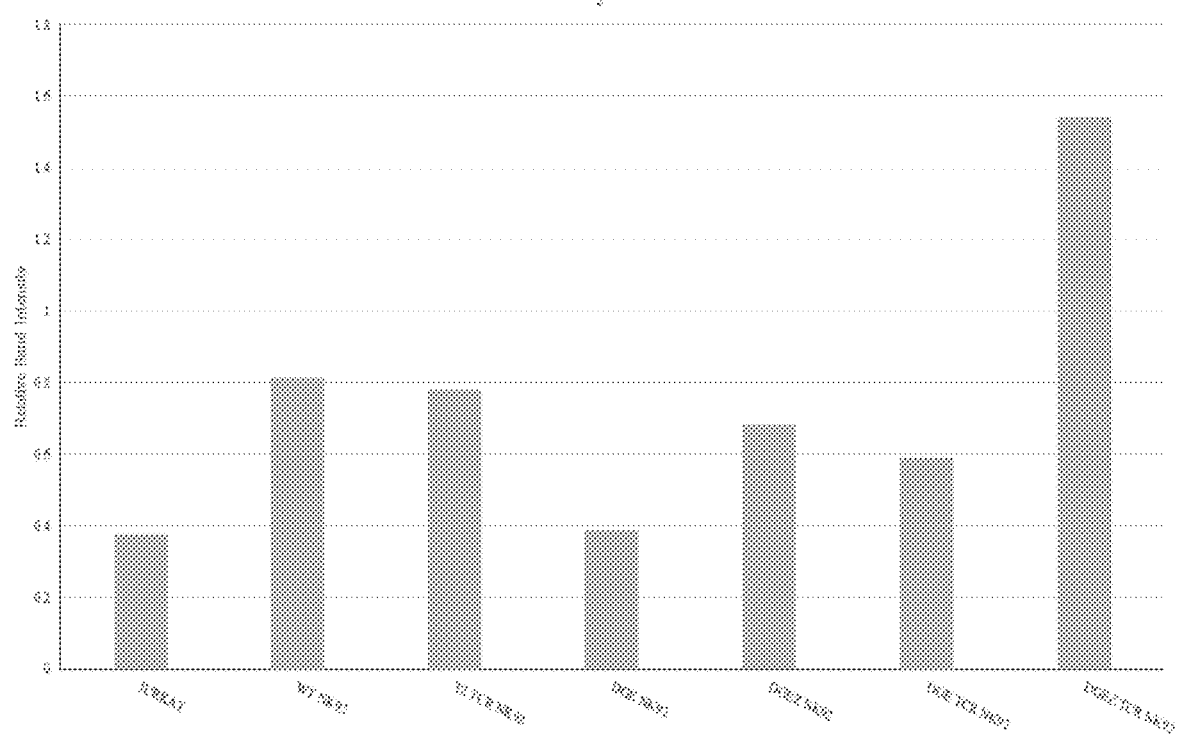
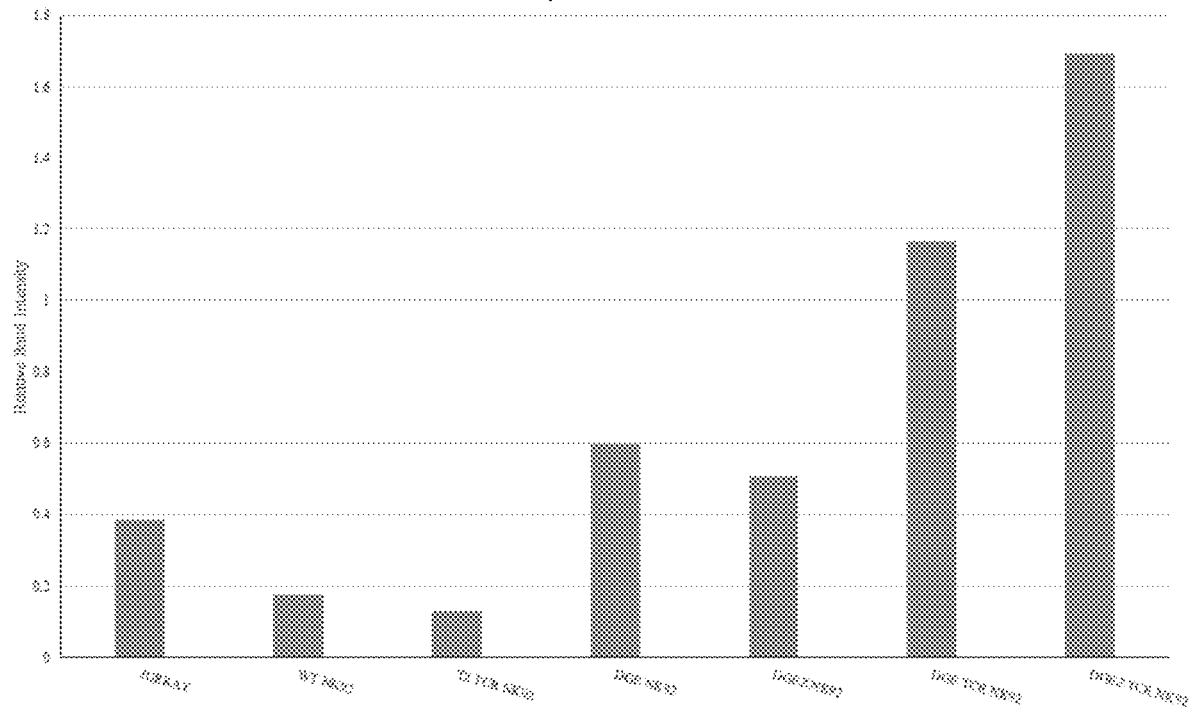
FIG. 19D

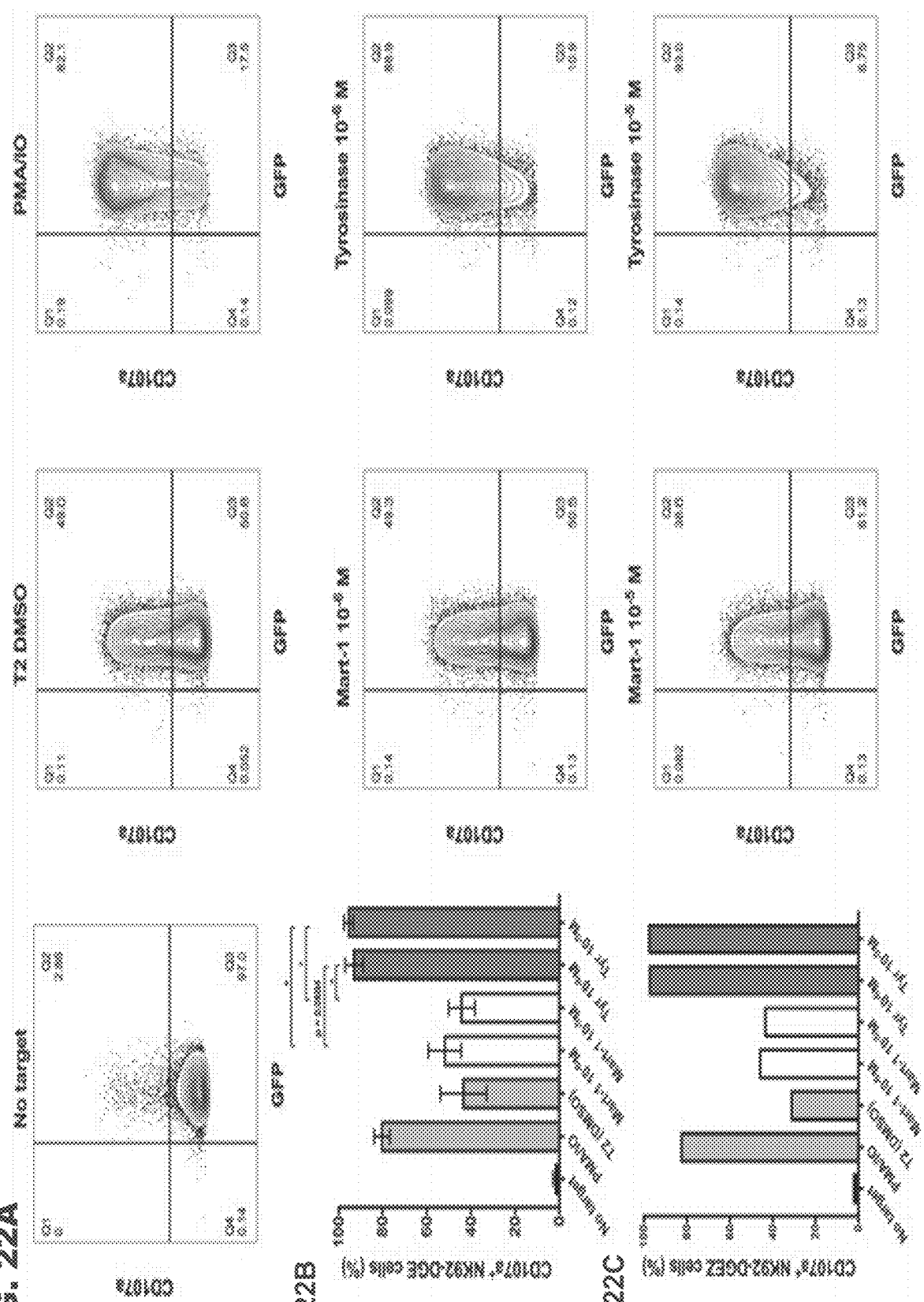

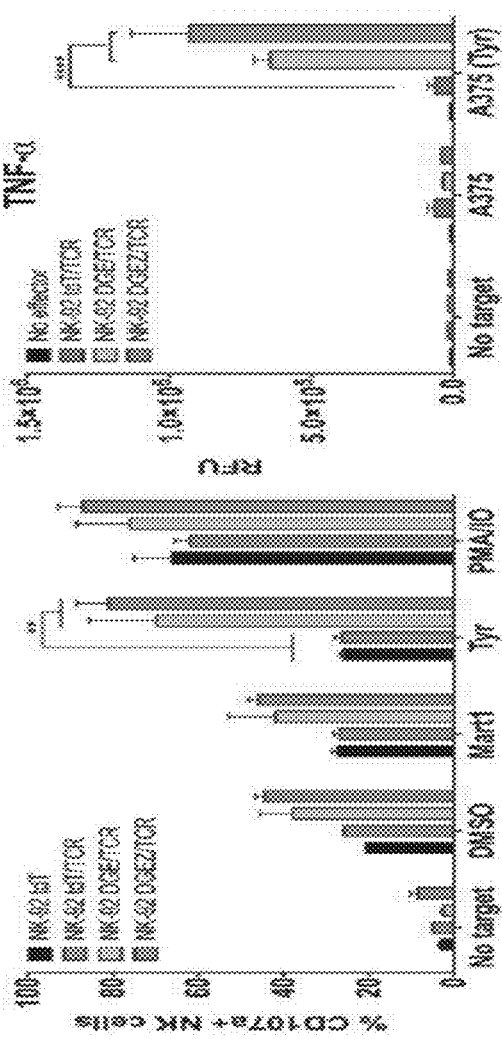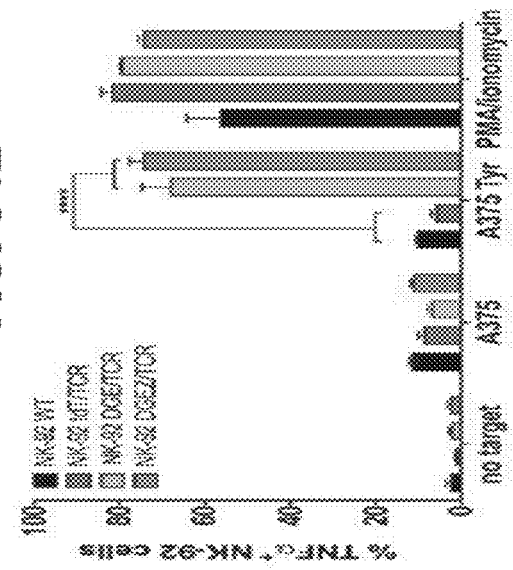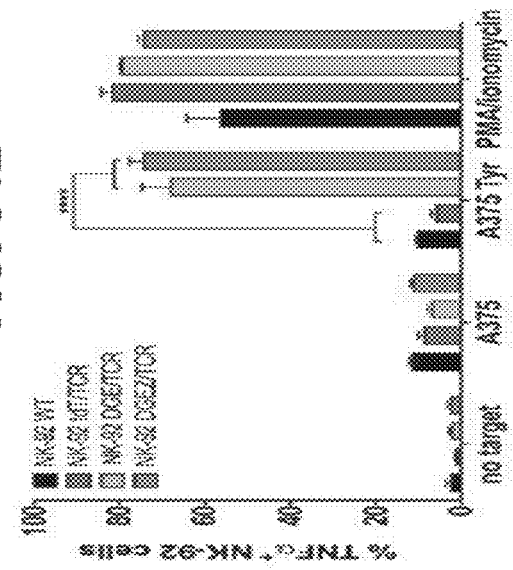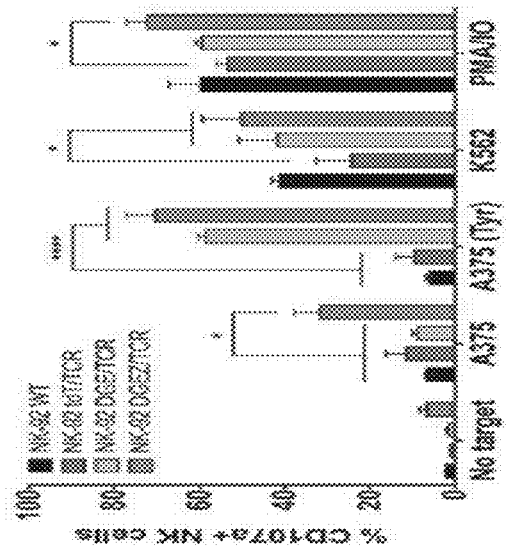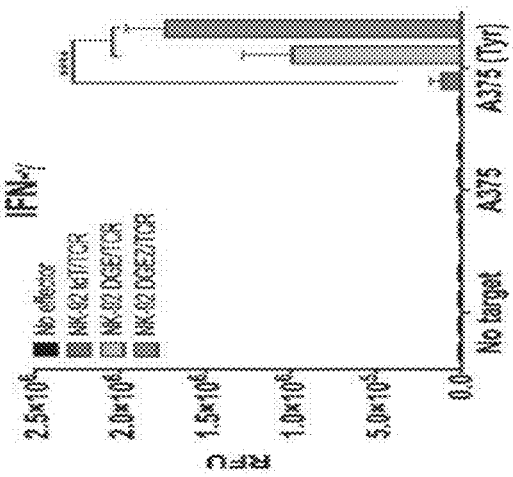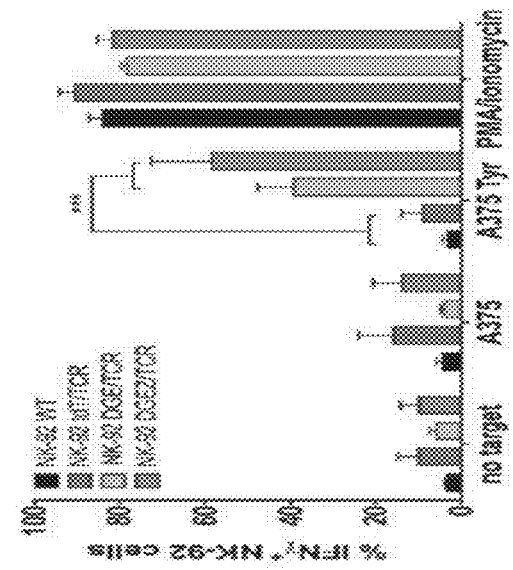

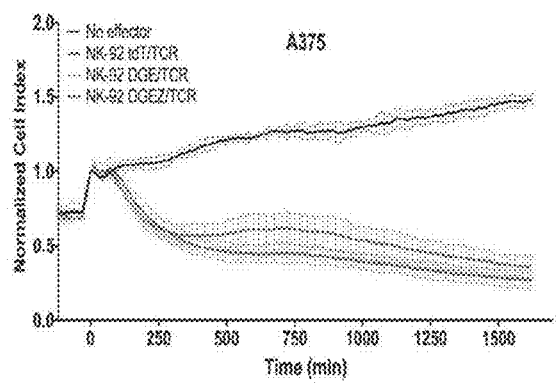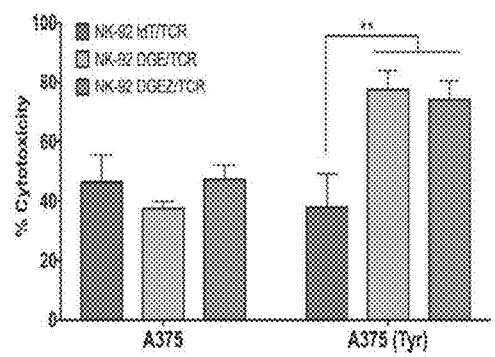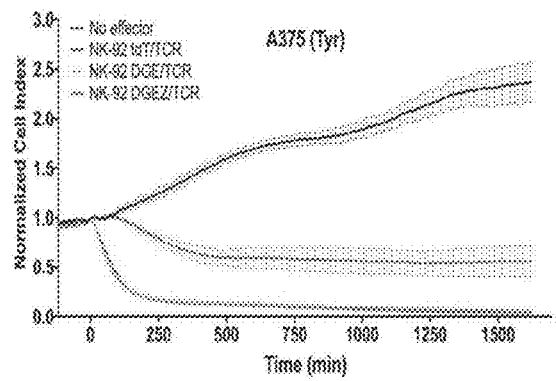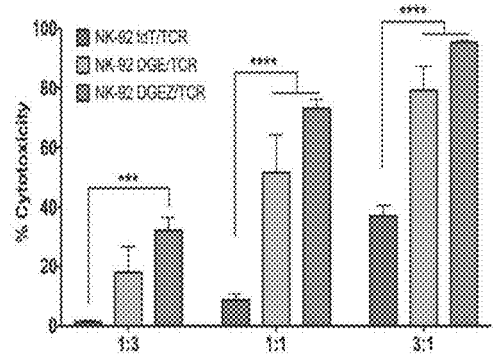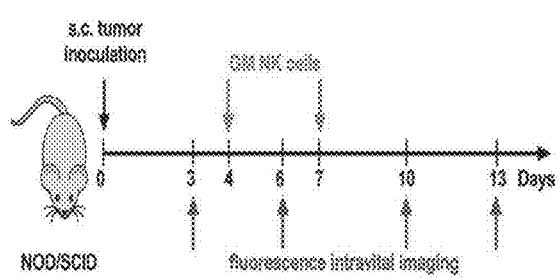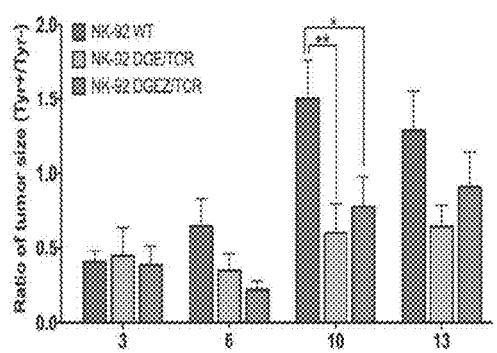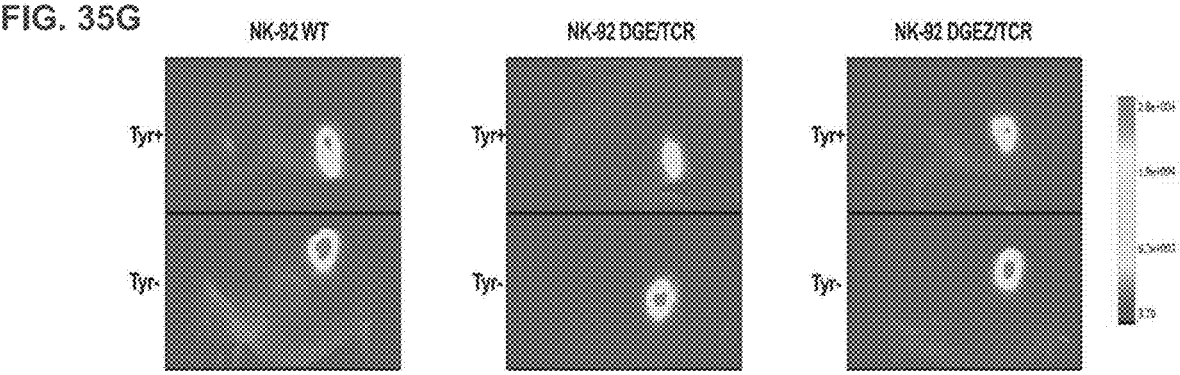

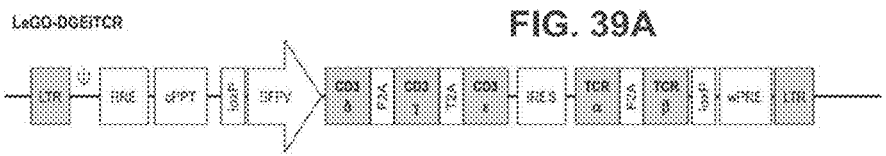
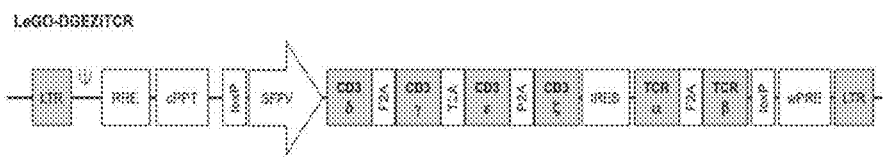
FIG. 39A
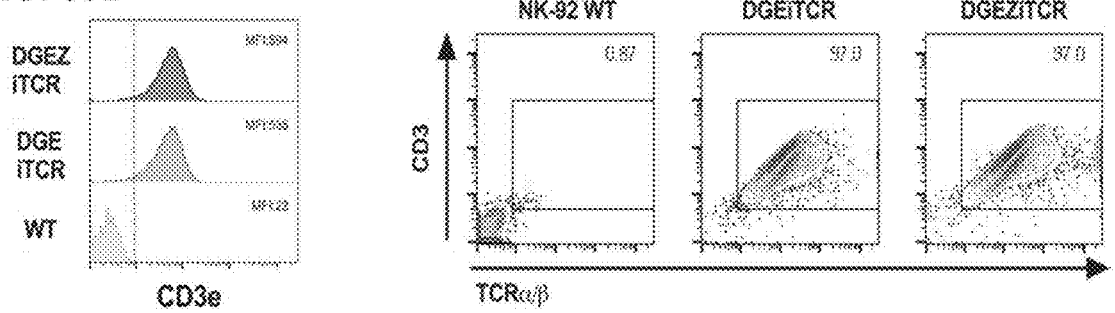
FIG. 39B
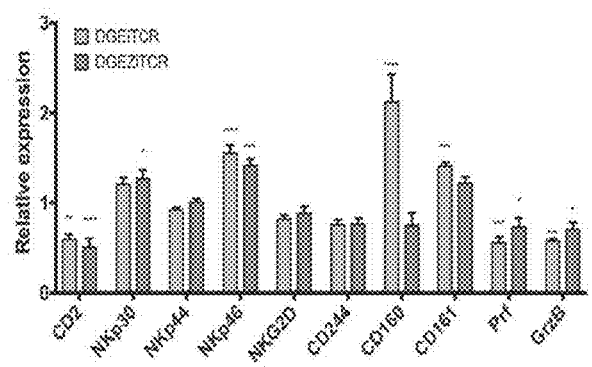
FIG. 39D
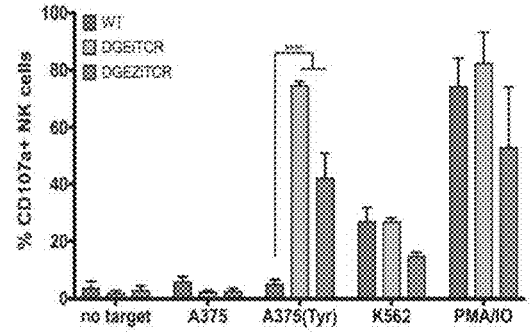
FIG. 39C
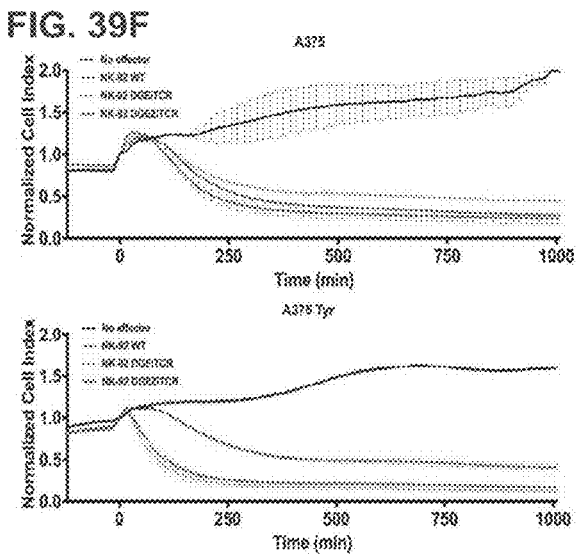
FIG. 39F
FIG. 39G
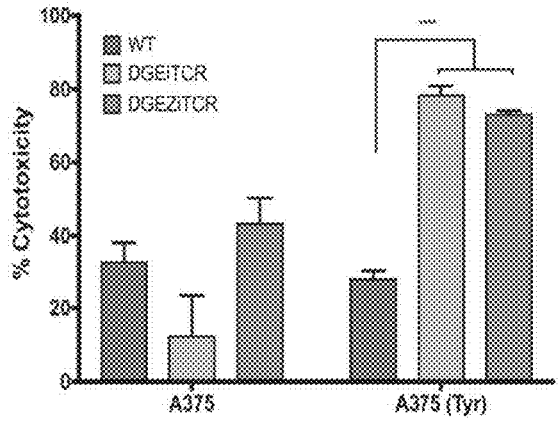
FIG. 39H

NATURAL KILLER (NK) CELLS EXPRESSING AN ANTIGEN-SPECIFIC FUNCTIONAL T CELL RECEPTOR (TCR) COMPLEX, METHODS FOR PRODUCTION THEREOF, AND METHODS FOR THERAPEUTIC USE THEREOF

FIELD OF THE INVENTION

The invention broadly relates to immunotherapy, particularly to T cell receptor (TCR) gene therapy, and most particularly to Natural Killer (NK) cells expressing an antigen-specific functional T cell receptor (TCR) complex. These modified Natural Killer (NK) cells have Major Histocompatibility Complex (MHC)-restricted antigen-specific cytotoxicity and are useful in therapy of cancer, viral infections, autoimmunity, and graft versus host disease (GvHD).

BACKGROUND

Natural Killer (NK) cells were discovered 40 years ago and identified by their ability to recognize and kill tumor cells without the requirement of prior antigen exposure. Since their discovery, NK cells have grown as promising agents for cell-based cancer immunotherapies. In the last decade, several NK cell based anti-cancer products have undergone clinical trials yielding promising results. However, in order to manufacture more NK cell therapy products with increasing efficiency, it is essential to develop novel strategies for increasing safety, efficiency, and specificity with approaches such as retargeting NK cells by expression of chimeric antigen receptors.

In the instant invention, NK cells are used for T cell receptor (TCR) gene therapy. These NK cells are reprogramed to selectively target antigens, such as tumor or viral antigens, in complex with the major histocompatibility complex (MHC).

TCR gene therapy was developed to redirect cytotoxic T cells towards selected epitopes of tumor antigens. However, due to the heterodimeric nature of the TCR molecule, $\alpha$ and $\beta$ chains introduced by gene delivery have a risk of pairing with the endogenously expressed complementary $\beta$ or $\alpha$ chains in the T cell. This phenomenon of "mispairing" gives rise to TCRs of unpredictable specificity having potentially lethal side effects.

Introduction of a functional TCR complex to NK cells that can inherently detect and eliminate virally infected and/or tumor cells enhances the efficiency of identification and killing of these cells as well as circumventing potential risk of TCR mispairing.

Recent decades have witnessed extraordinary improvements in the use of immunotherapy against malignancies and adoptive transfer of genetically-modified lymphocytes stands among promising tools in the fight against cancer. Harnessing the cytotoxic or immunomodulatory capacity of T cells, while maintaining a minimal risk of serious side effects such as the graft-versus-host-disease (GvHD), has been a major goal for cancer immunotherapy (Uttenthal B J, Chua I, Morris E C, Stauss H J. Challenges in T cell receptor gene therapy. J Gene Med. 2012 June;14(6):386-99).

A commonly used approach is the isolation and expansion of tumor associated antigen (TAA)-specific CD8+ T cells for adoptive transfer (Rosenberg S A, Dudley M E. Cancer regression in patients with metastatic melanoma after the transfer of autologous antitumor lymphocytes. Proc Natl Acad Sci USA. 2004 Oct. 5; 101 Suppl 2:14639-45). The techniques of TCR gene therapy have improved this approach by supplying large populations of antigen-specific T cells generated by transduction with the genes for a TCR with high avidity for the target antigen (Morgan R A, Dudley M E, Wunderlich J R, Hughes M S, Yang J C, Sherry R M, et al. Cancer regression in patients after transfer of genetically engineered lymphocytes. Science. 2006 Oct. 6; 314 (5796):126-9; Cooper L J, Kalos M, Lewinsohn D A, Riddell S R, Greenberg P D. Transfer of specificity for human immunodeficiency virus type 1 into primary human T lymphocytes by introduction of T-cell receptor genes. Journal of virology. 2000 September; 74(17):8207-12; and Rubinstein M P, Kadima A N, Salem M L, Nguyen C L, Gillanders W E, Nishimura M I, et al. Transfer of TCR genes into mature T cells is accompanied by the maintenance of parental T cell avidity. J Immunol. 2003 Feb. 1; 170(3): 1209-17).

Assembly and surface expression of the TCR introduced by gene delivery is a complex process, requiring pairing of the introduced $\alpha$ and $\beta$ chains to form a heterodimer that then associates with the four CD3 chains, $\gamma$, $\delta$, $\epsilon$ and $\zeta$. Due to the heterodimeric nature of the TCR molecule, $\alpha$ and $\beta$ chains introduced by gene delivery have a risk of pairing with the complementary $\beta$ or $\alpha$ chains endogenously expressed in the genetically-modified T cell (Govers C, Sebestyen Z, Coccoris M, Willemsen R A, Debets R. T cell receptor gene therapy: strategies for optimizing transgenic TCR pairing. Trends in molecular medicine. 2010 February; 16(2):77-87). This phenomenon, called "mispairing", has the potential to produce TCRs of unpredictable specificity that could be directed to self-antigens, thus potentially generating autoreactive T cells that have not been subjected to central tolerance and may cause a lethal GvHD-like syndrome in vivo (Bendle G M, Linnemann C, Hooijkaas A I, Bies L, de Witte M A, Jorritsma A, et al. Lethal graft-versus-host disease in mouse models of T cell receptor gene therapy. Nat Med. 2010 May; 16(5):565-70 and Ferrara J, Reddy P, Paczesny S. Immunotherapy through T-cell receptor gene transfer induces severe graft-versus-host disease. Immunotherapy. 2010 November; 2(6):791-4). This mispairing of $\beta$ or $\alpha$ chains is one of the most crucial problems to be solved if safe and successful TCR gene therapy is to be achieved.

Despite the promise of TCR gene therapy, the mispairing problem constitutes a bottleneck in the development of effective and safe therapies. Current approaches to minimizing mispairing during TCR gene transfer include modifications on the sequence, such as using constant region sequences from the mouse (Cohen C J, Zhao Y, Zheng Z, Rosenberg S A, Morgan R A. Enhanced antitumor activity of murine-human hybrid T-cell receptor (TCR) in human lymphocytes is associated with improved pairing and TCR/CD3 stability. Cancer Res. 2006 Sep. 1;66(17):8878-86 and Stanislawski T, Voss R H, Lotz C, Sadovnikova E, Willemsen R A, Kuball J, et al. Circumventing tolerance to a human MDM2-derived tumor antigen by TCR gene transfer. Nat Immunol. 2001 October; 2(10):962-70). However, this approach imposes the risk of developing an immune response towards the mouse sequences used (Davis J L, Theoret M R, Zheng Z, Lamers C H, Rosenberg S A, Morgan R A. Development of human anti-murine T-cell receptor antibodies in both responding and nonresponding patients enrolled in TCR gene therapy trials. Clin Cancer Res. 2010 Dec. 1; 16(23):5852-61) and eventual rejection of the genetically-modified cells. Other approaches include minimal structural modifications of the TCR in order to create additional disulphide linkages between the introduced $\alpha$ and $\beta$ chains (Kuball J, Dossett ML, Wolfl M, Ho W Y, Voss R H, Fowler C, et al. Facilitating matched pairing and expression of TCR chains introduced into human T cells. Blood. 2007 Mar. 15; 109(6):2331-8) as well as optimizing equimolar translation of the introduced α and β chains through the use of 2A linkers in gene transfer vectors (Szymczak A L, Workman C J, Wang Y, Vignali K M, Dilioglou S, Vanin E F, et al. Correction of multi-gene deficiency in vivo using a single 'self-cleaving' 2A peptide-based retroviral vector. Nat Biotechnol. 2004 May; 22(5): 589-94) in order to ensure that no excess TCR chain is available for mispairing. A variety of studies have focused on genetically linking TCR chains to signaling chains in the CD3/TCR complex (Govers C, Sebestyen Z, Roszik J, van Brakel M, Berrevoets C, Szoor A, et al. TCRs genetically linked to CD28 and CD3epsilon do not mispair with endogenous TCR chains and mediate enhanced T cell persistence and anti-melanoma activity. J Immunol. 2014 Nov. 15; 193(10):5315-26; Knies D, Klobuch S, Xue S A, Birtel M, Echchannaoui H, Yildiz O, et al. An optimized single chain TCR scaffold relying on the assembly with the native CD3-complex prevents residual mispairing with endogenous TCRs in human T-cells. Oncotarget. 2016 Mar. 25; and Tao C, Shao H, Yuan Y, Wang H, Zhang W, Zheng W, et al. Imaging of T-cell receptor fused to CD3zeta reveals enhanced expression and improved pairing in living cells. International journal of molecular medicine. 2014 September; 34(3):849-55) as well as carrying out the genetic modification process in hematopoietic progenitors rather than mature T cells in order to exclude endogenous TCR expression (Vatakis DN, Arumugam B, Kim S G, Bristol G, Yang O, Zack J A. Introduction of exogenous T-cell receptors into human hematopoietic progenitors results in exclusion of endogenous T-cell receptor expression. Molecular therapy: the journal of the American Society of Gene Therapy. 2013 May; 21(5):1055-63) while other studies have focused on the detection (Shao H, Zhang W, Hu Q, Wu F, Shen H, Huang S. TCR mispairing in genetically modified T cells was detected by fluorescence resonance energy transfer. Molecular biology reports. 2010 December; 37(8): 3951-6) and elimination (Kieback E, Charo J, Sommermeyer D, Blankenstein T, Uckert W. A safeguard eliminates T cell receptor gene-modified autoreactive T cells after adoptive transfer. Proc Natl Acad Sci USA. 2008 Jan. 15; 105(2):623-8) of T cells carrying mispaired TCR molecules after genetic modification. Additionally, approaches based on siRNA technology or genome editing, in order to knock-out endogenous TCR expression (Okamoto S, Mineno J, Ikeda H, Fujiwara H, Yasukawa M, Shiku H, et al. Improved expression and reactivity of transduced tumor-specific TCRs in human lymphocytes by specific silencing of endogenous TCR. Cancer Res. 2009 Dec. 1; 69(23):9003-11 and Provasi E, Genovese P, Lombardo A, Magnani Z, Liu P Q, Reik A, et al. Editing T cell specificity towards leukemia by zinc finger nucleases and lentiviral gene transfer. Nat Med. 2012 May; 18(5):807-15) are being widely investigated. Although successful to an extent, the majority of these procedures still carry a considerable risk of creating mispaired TCRs of unknown specificity.

NK cells have the ability to recognize and kill tumor cells without requiring prior antigen exposure. Such a characteristic highlights the importance of NK cells as promising agents for cell-based cancer therapies. Initial NK cell-based clinical trials suggest that NK cell-infusion is safe and feasible and shows almost no NK cell-related toxicity. A considerable amount of these clinical trials report effectivity. Furthermore, successful adoptive cell therapies, using NK cells from haploidentical killer immunoglobulin-like-receptor-ligand mismatched donors, have been achieved (Dahlberg C I, Sarhan D, Chrobok M, Duru A D, Alici E. Natural Killer Cell-Based Therapies Targeting Cancer: Possible Strategies to Gain and Sustain Anti-Tumor Activity. Frontiers in immunology. 2015; 6:605).

NK cell based cancer immunotherapy products can be prepared through ex vivo expansion and long-term activation as well as through genetic modification of NK cells, which opens up new possibilities for retargeting of these cells. Application of genetic modification can include various approaches, from induction of proliferation/survival via cytokine gene transfer to specific targeting of NK cells to malignant cells. The use of genetically-modified NK cells that have been redirected to tumors via the introduction of either activating receptors or (Pegram H J, Kershaw M H, Darcy P K. Genetic modification of natural killer cells for adoptive cellular immunotherapy. Immunotherapy. 2009 July; 1(4):623-30) chimeric antigen receptors (CARs) presents a hot prospect in clinical studies (Uherek C, Tonn T, Uherek B, Becker S, Schnierle B, Klingemann HG, et al. Retargeting of natural killer-cell cytolytic activity to ErbB2-expressing cancer cells results in efficient and selective tumor cell destruction. Blood. 2002 Aug. 15; 100(4):1265-73). CARs have been successfully delivered to NK cells and were shown to increase antigen specific cytotoxic activity both in vitro and in vivo (Kruschinski A, Moosmann A, Poschke I, Norell H, Chmielewski M, Seliger B, et al. Engineering antigen-specific primary human NK cells against HER-2 positive carcinomas. Proc Natl Acad Sci USA. 2008 Nov. 11; 105(45):17481-6). These improvements have rapidly been translated to experimental models (Lanier L L, Chang C, Spits H, Phillips J H. Expression of cytoplasmic CD3 epsilon proteins in activated human adult natural killer (NK) cells and CD3 gamma, delta, epsilon complexes in fetal NK cells. Implications for the relationship of NK and T lymphocytes. J Immunol. 1992 Sep. 15; 149(6):1876-80) and clinical trials. Taken together; these studies indicate that the adoptive transfer of genetically-engineered NK cells might be an efficient approach in cancer immunotherapy.

Several exemplary studies using wildtype (wt) or genetically-modified NK cell lines or tyrosinase-specific TCR gene therapy (using T cells as effector cells) are listed below.

Natural killer cell lines and methods of use—U.S. Patent Application Publication 2002/0068044 A1 and U.S. Patent Application Publication 2014/0099714 A1; inventor Hans Klingemann. These inventions relate to a natural killer cell line termed NK-92. Additionally, the inventions provide an NK-92 cell modified by transfection with a vector conferring advantageous properties, which is unable to proliferate and which preserves effective cytotoxic activity. The inventions further provide modified NK-92 cells. The cells secrete a cytokine upon being cultured under conditions that promote cytokine secretion, and furthermore secrete the cytokine in vivo upon being introduced into a mammal. In a significant embodiment, the cytokine is interleukin 2 (IL-2). The inventions also provide methods of purging cancer cells from a biological sample, of treating a cancer ex vivo in a mammal, and of treating a cancer in vivo in a mammal employing a natural killer cell, such as NK-92 cell which is unable to proliferate and which preserves effective cytotoxic activity, or natural killer cells transfected with a vector encoding a cytokine.

Genetically modified human natural killer cell lines— U.S. Patent Application Publication 2008/0247970 A1; inventor Kerry S. Campbell. The invention provides a natural killer cell, NK-92, further modified to co-express an associated accessory signaling protein such as FcεRI-γ or TCR-ζ chemokines, or cytokines such as interleukin-2 (IL-2) or interleukin-15 (IL-15). Additional methods are disclosed for various assays, assessments, and therapeutic treatments with the modified NK-92 cells.

Genetically modified yt cell line and use thereof—U.S. Patent Application Publication 2004/0120935 A1; inventor Gabriele Pecher. The invention relates to a YT cell line, modified by genetic engineering, into which the genes of receptors are introduced and which is suitable for treating tumours, tumour metastases, virus infections, and for cleaning (purging) blood stem cell preparations and also for diagnostic purposes. Areas of application include the medical field and the pharmaceutical industry. The aim of the invention is to identify tumour cells and other target cells by means of the gene transfer of specific receptors into the YT cell line. An additional aim is to cause a lysis of the identified tumour cells and other target cells, using the newly created cell line. The inventive cell line contains one or more receptors (consisting of variable regions of tumour-specific or target cell specific antibodies (single chain Pv fragments) and optionally a signal chain, which is derived from the zeta-chain of the human T-cell receptor.

High affinity T cell receptor and use thereof—U.S. Pat. No. 8,697,854 B2; inventors Dolores Schendel et al. The invention is directed to a high affinity T cell receptor (TCR) against a tumor-associated antigen, an isolated nucleic acid molecule encoding same, a T cell expressing the TCR, and a pharmaceutical composition for use in the treatment of diseases involving malignant cells expressing the tumor-associated antigen.

Universal Killer T-Cell—WO 2016/116601 A1; inventors Sébastien Wälchli et al. The invention relates to modified Natural Killer (NK) cells and their use in personalized medicine. The modified NK cells are non-immunogenic and are thus able to be administered to any recipient without being rejected by the host system; i.e. "universal." In one embodiment, the non-immunogenic NK cells are modified to express CD3 to allow a T cell receptor to be expressed. The non-immunogenic NK cells can be further modified to express a CD3 co-receptor together with the T cell receptor. Co-expression of CD3 with a specific T cell receptor results in the modified NK cells showing antigen-specific cytotoxicity towards target cells. These universal NK cells can thus be targeted to specific antigens, and may be used in personalized medicine, particularly in the field of oncology.

Treating viral hemorrhagic fever with NK-92 cells—WO 2016/057345 A1; inventors Tien Lee et al. This invention is directed to treatment of a patient having or suspected of having viral hemorrhagic fever with NK-92 cells.

Protocol and media for storage and transport of NK-92 cell line—International Application Serial No. PCT/US2014/059551; Hans Klingemann inventors et al. This invention is a storage medium for transport of NK-92 cells. This storage medium is sufficient to provide a therapeutic amount of NK-92 cells remaining viable for administration to a patient for up to a period of at least 24 hours after placement into the storage medium. Also disclosed are methods of transporting NK-92 cells using the described storage medium.

Interleukin-secreting natural killer cell lines and methods of use—U.S. Patent Application Publication 2004/0052770 A1; inventor Hans Klingemann. This invention relates to a natural killer cell line termed NK-92 that has been modified by transfection with a vector to confer advantageous properties. The invention provides modified NK-92 cells. In a significant embodiment, the cytokine is interleukin 2 (IL-2). The invention additionally provides a modified NK-92 cell line that is transfected with a vector that expresses a β32 microglobulin.

In the invention described and claimed herein, NK cells are used for TCR gene therapy in order to circumvent any risk of mispairing and provide MHC-restricted antigen specific cytotoxic activity by NK cells. The close developmental link between T and NK cells, the similarity of cellular signaling and cytotoxicity mechanisms between T and NK cells, and the expression of major TCR related genes in NK cells all provide a firm basis for the feasibility of the inventive approach.

TABLE 1

TCR related gene expression in NK cells

| Molecule | Role | Expression in NK cells | Reference |
|---|---|---|---|
| CD4 | Co-receptor | + | Bernstein H B, et al. Journal of immunology. 2006; 177: 3669-76. |
| CD8 | Co-receptor | + | Addison E G, et al. Immunology. 2005; 116: 354-61. |
| CD28 | Co-stimulation | + | Hunter C A, et al. Journal of immunology. 1997; 158: 2285-93. |
| LFA-1 | Adhesion | + | Barber D F, et al. Journal of immunology. 2004; 173: 3653-9. |
| CD3γ | TCR complex | − | Lanier L L, et al. Journal of immunology. 1992; 149: 1876-80. |
| CD3δ | TCR complex | − | Moingeon P, et al. European journal of immunology. 1990; 20: 1741 Lanier L L, et al. Journal of immunology. 1992; 149: 1876-80. |
| CD3ε | TCR complex | + (?) | Lanier L L, et al. Journal of immunology. 1992; 149: 1876-80. |
| CD3ζ | TCR complex | + | Moingeon P, et al. European journal of immunology. 1990 ; 20: 1741 |
| Lck | TCR signaling | + | Biondi A, et al. European journal of immunology. 1991; 21: 843-6. Pignata C, et al. Cellular immunology. 1995; 165: 211-6. |
| Fyn | TCR signaling | + | Rabinowich H, et al. Journal of immunology. 1996; 157: 3860-8. |
| ZAP70 | TCR signaling | + | Rabinowich H, et al. Journal of immunology. 1996; 157: 3860-8. |
| LAT | TCR signaling | + | Jevremovic D, et al. Journal of immunology. 1999; 162: 2453-6. |
| ERK | TCR signaling | + | Yu T K, et al. Journal of immunology. 2000; 164: 6244-51. |
| JNK | TCR signaling | + | Kumar D, et al. Journal of immunology. 2009; 182: 1011-20. |
| NFAT | TCR signaling | + | Fric J, et al. Blood. 2012; 120: 1380-9. |
| SLP-76 | TCR signaling | + | Peterson E J, et al. European journal of immunology. 1999; 29: 2223. |
| Vav-1 | TCR signaling | + | Chan G, et al. European journal of immunology. 2001; 31: 2403-10. |
| PLC-γ-1 | TCR signaling | + | Upshaw J L, et al. Journal of immunology. 2005; 175: 213-8. |

The inventive NK cells and methods described herein not only open up a whole new chapter in the field of cancer immunotherapy but also provide a final and definitive solution for the mispairing problem observed in TCR gene therapy.

SUMMARY OF THE INVENTION

The inventive concept primarily focuses on the use of T cell receptor (TCR) genes for the genetic modification and retargeting of natural killer (NK) cells towards tumor-associated antigens (TAA), in an effort to develop a new approach in TCR gene therapy that circumvents the problems associated with mispairing of TCR chains. The invention accomplished the following:

Aim 1. Identification of the minimum requirements for the expression of functional TCRs on the NK cell surface.

Aim 2. Targeting NK cell-mediated cellular cytotoxicity towards a certain TAA via the expression of TCRs on the NK cell surface.

Aim 3. Comparative evaluation of the cytotoxicity and specificity of TCR modified NK cells and T cells.

In 1909, Paul Erlich was the first to propose in theory that the immune system had the potential to fight against tumors (Erlich *Ned Tijdschr Geneeskd.* 5:273-290 1905). Half a century later, Thomas and Burnet put forward the "cancer immunosurveillance" theory (Burnet *Br Med Journal* 1:779-786 1957). While this theory was seriously challenged in its first years, it has stood the test of time and it is now evident that the development of any malignancy is under close surveillance by members of the immune system. Today, successful applications of cancer immunotherapy cover a broad base from the use of monoclonal antibodies or recombinant cytokines to adoptive transfer of genetically modified lymphocytes in order to trigger a graft-versus-tumor effect. Traditionally, the focus has been on T cells, but more and more other players of the immune system such as NK cells are stepping on the scene. T and NK cells need to communicate with other cells in the body in order to coordinate the identification of self, non-self or altered self. Direct communication between a T cell and the target cell is achieved through the interactions of major histocompatibility complex (MHC) TCRs and use a battery of activating and inhibitory receptors. NK cell cytotoxicity is the result of a complex interaction between the inhibitory and activating signals coming from these receptors (Lanier *Curr Opin Immunol.* 15:308-314 2003). Interestingly, MHC, which is an essential molecule for T cell based immune defense, also plays a pivotal role in the modulation of NK cell biology. However, unlike T cells, NK cells don't express a unique, antigen specific receptor. Harnessing the cytotoxic or immunomodulatory capacity of T cells without risking serious side effects such as the graft-versus-host-disease (GvHD) has been a major goal for the cellular immunotherapy of cancer (Uttenthal et al. *The Journal of Gene Medicine* 14:386-399 2012).

The instant invention represents a new paradigm in cellular immunology and can be used in the treatment of a variety of diseases such as cancers, viral infections, autoimmune diseases, and graft versus host disease (GvHD).

In a general aspect, the invention provides an immunotherapeutic method using T cell receptor (TCR) gene transfer.

In one aspect, the invention provides a modified cell, preferably, but not limited to, a Natural Killer (NK) cell, expressing an antigen-specific functional T cell receptor (TCR) complex. By "modified" it is meant that the cell has been altered from its natural state. The modifications are contemplated as being genetic, epigenetic, and/or non-genetic.

The invention is contemplated as applicable to any cell that can be modified to express an antigen-specific functional T cell receptor (TCR) complex; non-limiting examples include stem cells, cells of hematopoietic lineage, and an HEK-293 cell.

The invention particularly encompasses any Natural Killer (NK) cell. Preferred, non-limiting examples are an NK-92 cell, a YTS cell, and a primary human NK cell.

Further, the invention can be directed against an antigen or a combination of antigens of any type or from any source. Additionally, the antigens can be located on a cellular surface or can be intracellular. Preferred, non-limiting examples are tumor antigens, tumor-associated antigens, viral antigens, and virus-associated antigens. A specific, non-limiting example, exemplified herein is tyrosinase, a melanoma-associated antigen.

The described modified cells and NK cells are contemplated for use with various therapies, such as, but not limited to, immunotherapy, cell therapy, adoptive cell therapy, and T cell receptor (TCR) gene therapy.

In another aspect, the invention provides a modified cell, preferably, but not limited to, a Natural Killer (NK) cell, having Major Histocompatibility Complex (MHC)-restricted antigen-specific cytotoxicity. The MHC can be any of MHC-class I, MHC-class II, and MHC-like molecules. A non-limiting example of an MHC-like molecule is HLA-E.

In a further aspect, the invention provides a method for producing a modified cell, preferably, but not limited to a Natural Killer (NK) cell, expressing an antigen-specific functional T cell receptor (TCR) complex. The method includes providing a cell/Natural Killer (NK) cell and modifying the cell to express the antigen-specific functional T cell receptor (TCR) complex. The modified cell can be any cell. Preferred, non-limiting examples are an NK-92 cell, a YTS cell, and a primary human NK cell.

Modification of the cells/NK cells includes transfer of gene sequences encoding proteins of the TCR complex. For example, transferring sequences encoding a T cell receptor (TCR) α chain, a T cell receptor (TCR) β chain, and CD3 chains to the cell using one or more viral vectors. One, several, or all of the CD3 chain sequences, CD3 γ chain, a CD3 δ chain, a CD3 ε chain, and a CD3 ζ chain, can be transferred.

Any viral vector effective to transfer the sequences can be used such as lentiviral vectors or retroviral vectors.

In another aspect, the invention provides a therapeutic composition including modified cells, preferably, but not limited to Natural Killer (NK) cells, expressing an antigen-specific functional T cell receptor (TCR) complex and at least one pharmaceutically-acceptable carrier for administration of living cells.

The phrase "pharmaceutically-acceptable carrier" refers to an inactive and non-toxic substance used in association with an active substance, i.e. in this invention the modified NK cell, especially for aiding in the application/delivery of the active substance. Any art-acceptable medium or carrier is contemplated for use in administrating the living cells. Other, non-limiting, examples of pharmaceutically-acceptable excipients are diluents, binders, disintegrants, superdisintegrants, flavorings, fillers, and lubricants.

In a further aspect, the invention encompasses a method of treatment of a disease. The method includes providing a composition including a modified cell/Natural Killer (NK) cell expressing an antigen-specific functional T cell receptor (TCR) complex and at least one pharmaceutically-acceptable carrier for administration of living cells; and administering the composition to the subject. This method is contemplated as being therapeutically effective for treatment of many diseases and conditions. Preferred, but non-limiting examples include cancer, viral infections (i.e. HIV), autoimmune diseases, and graft versus host (GvHD).

The phrase "effective amount" refers to the amount of a composition necessary to achieve the composition's intended function.

The phase "therapeutically-effective amount" refers to the amount of a composition required to achieve the desired function, i.e. cytotoxicity towards infected or malignant cells.

In a further aspect, the invention provides a method for inducing antigen-specific pro-inflammatory cytokine production and secretion in a subject, human or animal, in need thereof. The method includes providing a composition including a modified cell/Natural Killer (NK) cell expressing an antigen-specific functional T cell receptor (TCR) complex and at least one pharmaceutically-acceptable carrier for administration of living cells; and administering the composition to the subject.

In another aspect, any of the above-disclosed NK cells can be used in the manufacture of any of the above-disclosed compositions and therapeutic compositions.

There are multiple advantages and uses of the technology described herein. Non-limiting examples include:

1) Induction of antigen-specific pro-inflammatory cytokine production and secretion upon engagement of TCR complex to its cognate pMHC complex. This is important since NK-TCR cells does not only kill the target cells, it can also recruit other immune cells for a more diverse targeting of the tumor and tumor microenvironment. These cytokines can also change the phenotype of the tumor and the tumor microenvironment potentially resulting in less favorable environment for tumor growth.

2) NK-TCR cells respond very fast upon getting in contact with the target cells, faster than the unmodified NK cells. Unlike T cells, they do not require prior sensitization for exerting their effector functions. The described experiments show rapid responses within minutes when it comes to degranulation and target cell lysis.

3) Targeting of intracellular antigens. The genetic modification enables NK cells to recognize and respond to intracellular antigens presented by MHC molecules. While NK cells can distinguish some of the MHC presented antigens through its pattern recognition receptors such as KIRs, NKG2A and NKG2C receptors, it has never been as specific as TCR mediated targeting of intracellular antigens.

4) Demonstration of in vivo activity of NK-TCR cells. NK-TCR cells can selectively target and respond to antigen positive tumors in vivo. This is a major step towards using these cells in different immunotherapy approaches.

5) Initial experimentation is based on two-step introduction of CD3 subunits and TCR. Study 3 shows induction of the same effector functions using a single vector encoding both CD3 subunits and the TCR subunits.

6) Wide Range use of NK-TCR cells. In addition to targeting tumor cells and viral infection, this technology can also be applied to target autoimmune diseases by using TCRs specific to antigens exclusive to activated auto-reactive lymphocytes such as T cells and B cells.

7) Targeting of immunosuppressive components of the tumor microenvironment such as tumor associated macrophages and dendritic cells, myeloid-derived suppressor cells.

8) Targeting of any disease associated MHC positive cells or cell populations that has exclusive antigen repertoire.

9) Targeting of antigens presented by classical MHC molecules such as MHC-I and MHC-II and also targeting of other MHCs and MHC-like molecules, for example, HLA-E.

10) Further programing these NK cells towards a non-killer phenotype and induce anti-inflammatory cytokine secretion for antigen specific suppression of inflammation such as autoimmune diseases.

11) Expanding of the cell types that can be genetically-modified, for example, cell surface expression of TCR when introduced together with CD3s on HEK293 cells. It is possible to introduce, especially using the single vector system, not only to NK cells but other cells types such as hematopoietic stem cells and its downstream lineages. The CD3/TCR can potentially be expressed on multiple cell line types with a very diverse effector functions.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

FIG. 1A shows lentiviral vector constructs designed and used to genetically modify NK cells.

FIG. 1B shows flow cytometry based cell surface and intracellular CD3e expression analysis in NK cells transduced with LeGO-DGEiG2puro, and LeGO-DGEZ-iG2—puro lentiviral vectors.

FIG. 1C shows flow cytometry based cell surface CD3e expression analysis on NK-92-LeGO-T2puro cells, NK-92-DGE-iT2 cells, and NK-92DGEZ-iT2 cells transduced with vector carrying TCR (tyrTCR-IRES-eGFP).

FIGS. 2A-C show that simultaneous expression of TCR and CD3 complex on NK cells enables TCR to bind cognate peptide MHC complex.

FIG. 2A shows flow cytometry based analysis of tyrosinase (368-376)/HLA-A2 pentamer staining on tdT-NK-92 cells, tdT/TCR-GFP NK-92 cells, DGE-tdT/TCRGFP NK-92 cells, and tdT/TCR-GFP NK-92 cells.

FIG. 2B shows enrichment of tdT+ and GFP+ cells by flow cytometry based cell sorting on DGE-tdT/TCR-GFP NK-92 cells and tdT/TCR-GFP NK-92 cells. Representative plot demonstrates purity of tdT+GFP+ before and after cell sorting.

FIG. 2C shows flow cytometry based analysis of tyrosinase (368-376)/HLA-A2 pentamer staining on tdT+GFP+ enriched DGE-tdT/TCR-GFP NK-92 cells and tdT/TCR-GFP NK-92 cells.

FIG. 3A shows representative flow cytometry graphs of CD107a degranulation on tyrTCR expressing NK-92 DGE cells. Background CD107a degranulation (no target), maximal CD107a degranulation (PMA/IO) and degranulation against DMSO, Mart-1 and Tyrosinase peptide loaded T2 cells.

FIG. 3B shows CD107a degranulation on tyrTCR expressing NK-92 DGE cells (independent experiments). Statistical analysis is done by one-way ANOVA test followed by Turkey multicomparison test, *p<0.05.

FIG. 3C shows CD107a degranulation on tyrTCR expressing NK-92 DGEZ cells (single experiment).

FIGS. 4A-E show that simultaneous expression of TCR and CD3 complex on NK cells enables TCR to bind cognate peptide MEW complex.

FIG. 4A shows lentiviral vector constructs designed and used to genetically modified NK cells: TyrTCR-IRES-eGFP (TCR); LeGO-iT2puro (tdT); LeGO-DGE-iT2puro (DGE); and LeGO-DGEZ-iT2puro (DGEZ).

FIG. 4B shows flow cytometry based cell surface and intracellular CD3e expression analysis in NK cells transduced lentiviral vectors.

FIG. 4C shows Western blot analysis of CD3δ, CD3γ, and CD3ζ in WT (wildtype) and genetically modified NK-92 cells.

FIG. 4D shows a flow cytometry based analysis of anti-TCR staining on genetically modified NK-92 cells.

FIG. 4E shows a flow cytometry based analysis of tyrosinase$_{(368-376)}$/HLA-A2 pentamer staining on genetically modified NK-92 cells.

FIGS. 6A-B show that A375 cells or A375(Tyr) cells were seeded into E-16 plate. 16 hours later, transgenic NK-92 cells or YTS cells were added onto the target cells at an E:T ratio of 1:1. Real time measurements were performed by recording the Cell index (CI) every 15 min, for 40 h using Xcelligence RTCA platform.

FIG. 6C shows that target cell killing is assessed by Cr$^{51}$ release assay. Cr51 labelled A375 or A375 (TYR) cells were co-incubated with transgenic NK-92 cells at indicated ratios for 4 hours. Target cell killing is calculated through measuring radioactivity in the co-culture supernatant.

FIG. 6D shows that transgenic NK-92 cells were mixed with A375 or A375 (TYR) cells at 1:2.5 ratios and images were captured for 2 hours every 15 seconds. Representative images at the start of co-incuboation (upper panel) and at the end of the experiment (lower panel).

FIGS. 7A-C show CD107a degranulation of NK-TCR against A375 and A375(Tyr).

FIG. 7A shows NK92 (WT).
FIG. 7B shows NK92 DGE TCR.
FIG. 7C shows NK92 DGEZ TCR.

FIG. 8A shows DGE TCR.
FIG. 8B shows DGEZ TCR.

FIG. 9A shows EXP2 and 3 combined 1H A375s.
FIG. 9B shows EXP2 and 3 combined 1H T2.
FIG. 9C shows EXP2 and 3 combined 1H K562.
FIG. 9D shows EXP2 and 3 combined 4H A375s.
FIG. 9E shows EXP2 and 3 combined 4H T2.
FIG. 9F shows EXP2 and 3 combined 4H K562.

FIG. 10A shows EXP1 NK-TCR A375.
FIG. 10B shows EXP2 NK-TCR A375.
FIG. 10C shows cytotoxicity time A375 vs. A375(Tyr).
FIG. 10D shows EXP1 NK-TCR A375(Tyr).
FIG. 10E shows EXP2 NK-TCR A375(Tyr).
FIG. 10F shows combined cytotoxicity time K562.

FIGS. 11A-C shows E:T ratio dynamics (bar graphs) of cytotoxic activity of NK-TCR cells against A375 and A375 (Tyr) cells.
FIG. 11A shows data obtained from Study 1.
FIG. 11B shows data obtained from Study 2.
FIG. 11C shows combined data from Studies 1 and 2.

FIG. 18A shows LegoT2puroTCR.
FIG. 18B shows DGE T2 TCR.
FIG. 18C shows DGEZ T2 TCR.

FIGS. 19A-D show results from Western Blotting experiments.
FIG. 19A is a photograph of the blots.
FIG. 19B shows the relative intensity of bands for CD3δ.
FIG. 19C shows the relative intensity of bands for CD3ζ.
FIG. 19D shows the relative intensity of bands for CD3γ.

FIGS. 22A-C shows results from cytotoxicity experiments.

FIG. 23A is photograph of the cells at low density.
FIG. 23B is photograph of the cells at high density.

FIG. 24A shows LegoiT2puro selected cells.
FIG. 24B shows DGE TCR YTS cells.
FIG. 24C shows DGEZ TCR YTS cells.

*FIGS. 32 and 33-Relative expression is calculated by the mean fluorescence intensity ratio of GM cells to wild type (WT) cells after normalization with isotype controls. (**$p<0.005$, 2-way ANOVA with Fisher's LSD test).

FIGS. 34A-F are bar graphs showing cell surface expression levels of CD107a on NK cells (indicative of degranulation) measured upon target cell exposure for 5 hours at a 1:1 ratio.

FIG. 34A shows degranulation of NK-92 cells against T2 cells loaded with indicated peptides or DMSO (control).

FIGS. 34B-D shows degranulation of NK-92 cells against target cell lines including A375, A375(Tyr) and K562 (FIG. 34B); TNF-α secretion (FIG. 34C) and IFN-γ secretion as assessed by Pathscan Th1/Th2/Th17 Cytokine Antibody Array after co-culture of NK cells with A375 or A375(Tyr) targets (FIG. 34D).

FIG. 34E shows percentage of TNF-α$^+$ cells as assessed by flow cytometry after co-culture with A375 or A375(Tyr) targets.

FIG. 34F shows percentage of IFN-γ$^+$ NK cells as assessed by flow cytometry after co-culture with A375 or A375(Tyr) targets.

*FIGS. 34A-F—Mean and SEM are shown from at least two independent experiments (*$p<0.05$; $p<0.005$; *$p<0.0005$; ****$p<0.0001$, 2-way ANOVA with Fisher's LSD test) (RFU: Relative Fluorescence Unit).

FIGS. 35A-G present data showing in vitro cytotoxic activity and in vivo efficacy of TCR expressing NK cells. For measurement of cytotoxic activity by RTCA, A375 or A375(Tyr) cells were seeded into E-16 plates. 14-16 hours later, NK cells were added onto the target cells at an E:T ratio of 1:1. Real-time measurements were performed by recording the Cell Index (CI) every 15 min, for 40 h using the Xcelligence RTCA platform.

FIG. 35A shows representative CI plots of A375 cells upon co-culture with NK-92 cells.

FIG. 35B shows representative CI plots of A375(Tyr) cells upon co-culture with NK-92 cells showing antigen-specific killing activity.

FIG. 35C is a bar graph showing % Cytotoxic activity calculated using CI values at the 4-hour time point during RTCA.

FIG. 35D is a bar graph showing target cell killing by GM NK cells at various E:T ratios calculated using CI values at the 4-hour time point during RTCA.

*FIGS. 35A-D—Mean and SEM are shown from at least two independent experiments.

FIG. 35E illustrates the experimental setup used to assess the in vivo activity of GM NK cells against A375 and A375(Tyr) tumors in NOD/SCID mice. NOD/SCID mice were s.c. injected with 100.000 A375 cells (left flank) and 100.000 A375(Tyr) cells (right flank) followed by intratumoral injection of effector cells or with PBS at 4 days and 7 days after tumor transplantation. Tumor growth was followed by fluorescent intensity at the indicated days. Intravital imaging using the Bruker Xtreme II system was performed on days 3, 6, 10 and 13 post tumor inoculation under isoflurane anesthesia. Fluorescence intensities recorded from A375(Tyr) tumors on the right flanks of each mice were normalized by the fluorescence intensity recorded from the A375 tumor on the left flank of the same mouse as an internal control.

FIG. 35F is a bar graph showing relative tumor sizes in NOD/SCID mice transplanted with A375 and A375(Tyr) tumors after GM NK cell treatment (n=5 per group).

FIG. 35G shows representative images of fluorescence intensity from the three treatment groups on day 10 of tumor growth (*$p<0.05$; $p<0.005$; *$p<0.0005$; ****$p<0.0001$, 2-way ANOVA with Fisher's LSD test).

FIG. 36A shows NK-92 DGE/TCR cells.

FIG. 36B shows NK-92 DGEZ/TCR cells.

FIG. 37A shows degranulation of YTS cells against T2 cells loaded with indicated peptides or DMSO.

FIG. 37B shows degranulation of YTS cells against target cell lines including A375, A375(Tyr) and K562.

FIG. 37C shows representative CI plots of A375 (upper panel) and A375(Tyr) (lower panel) cells upon co-culture with NK-92 cells.

FIG. 37D is a bar graph showing % Cytotoxic activity calculated using CI values at the 4-hour time point during RTCA. Mean and SEM are shown from at least two independent experiments are shown (*$p<0.05$; $p<0.005$; **$p<0.0001$, 2-way ANOVA with Fisher's LSD test).

FIGS. 39A-H illustrate genetic modification of NK cells for TCR expression using a single vector.

FIG. 39A shows lentiviral vector constructs used to genetically modify NK cells for TCR expression in a single-step procedure.

FIG. 39B shows flow cytometry-based cell surface and intracellular CD3ε expression analysis in WT and GM NK-92 cells.

FIG. 39C shows flow cytometry-based analysis of TCR α/β staining on WT and GM NK-92 cells.

FIG. 39D shows flow cytometry-based phenoyping of NK cell surface receptors, intracellular Prf and GrzB levels on GM NK-92 cells. Relative expression is calculated by the mean fluorescence intensity ratio of GM cells relative to WT cells after normalization with isotype controls. Phenotypic comparison of GM NK-92 cells and WT NK-92 cells demonstrated reduced levels of CD2, while NK-92 expressing single DGEiTCR vector had reduced levels of Prf and GrzB, and increased expression of CD160 and CD16. Cell surface expression of and NKp46 was significantly increased for both GM NK-92 cell lines.

FIG. 39E shows degranulation of GM NK-92 cells against target cell lines including A375, A375(Tyr) and K562.

FIG. 39F shows representative CI plots of A375 cells upon co-culture with NK-92 cells.

FIG. 39G shows representative CI plots of A375(Tyr) cells upon co-culture with NK-92 cells showing antigen-specific killing activity.

FIG. 39H is a bar graph showing % Cytotoxic activity calculated using CI values at the 4-hour time point during RTCA. Mean and SEM are shown from at least two independent experiments are shown (*p<0.05; p<0.005; **p<0.0001, 2-way ANOVA with Fisher's LSD test).

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described Natural Killer (NK) cells, the described methods for producing/preparing the NK cells, the described therapeutic compositions containing the NK cells, and the described therapeutics use of the NK cells and any further application of the principles of the invention as described herein, are contemplated as would normally occur to one skilled in the art to which the invention relates.

The inventive NK cells and methods described herein not only open up a whole new chapter in the field of cancer immunotherapy but also provide a final and definitive solution for the mispairing problem observed in TCR gene therapy.

Study 1:
Cell Surface Expression of TCR Complex on NK Cells

TCR complex is composed of six different chains: CD3 molecules (CD3γ, CD3δ, CD3ε, CD3ζ) assembled with the TCRα/β heterodimer. As summarized in Table 1 above, various studies have identified that NK cells have almost all molecules necessary for TCR assembly and signalling readily available, with the exception of CD3γ and CD3δ. Lanier et al. (Lanier L L, Chang C, Spits H, Phillips J H. Expression of cytoplasmic CD3 epsilon proteins in activated human adult natural killer (NK) cells and CD3 gamma, delta, epsilon complexes in fetal NK cells. Implications for the relationship of NK and T lymphocytes. J Immunol. 1992 Sep. 15; 149(6):1876-80) have also demonstrated that human fetal liver NK cells express all CD3 chains and have cytoplasmic CD3γ/δ/ε complexes that cannot be transported to the cell surface. With this data in mind, TCR α/β expressing vectors were delivered into NK cells, along with lentiviral vector-based expression of CD3δ, CD3γ, and CD3ε in the presence and absence of CD3ζ(which is readily expressed in NK cells) to observe TCR assembly on the NK cell surface.

For detailed analysis of factors effecting TCR assembly on the NK cell surface and optimization of TCR expression, the NK cell line NK92 was used as a model system.

Figure 1A:
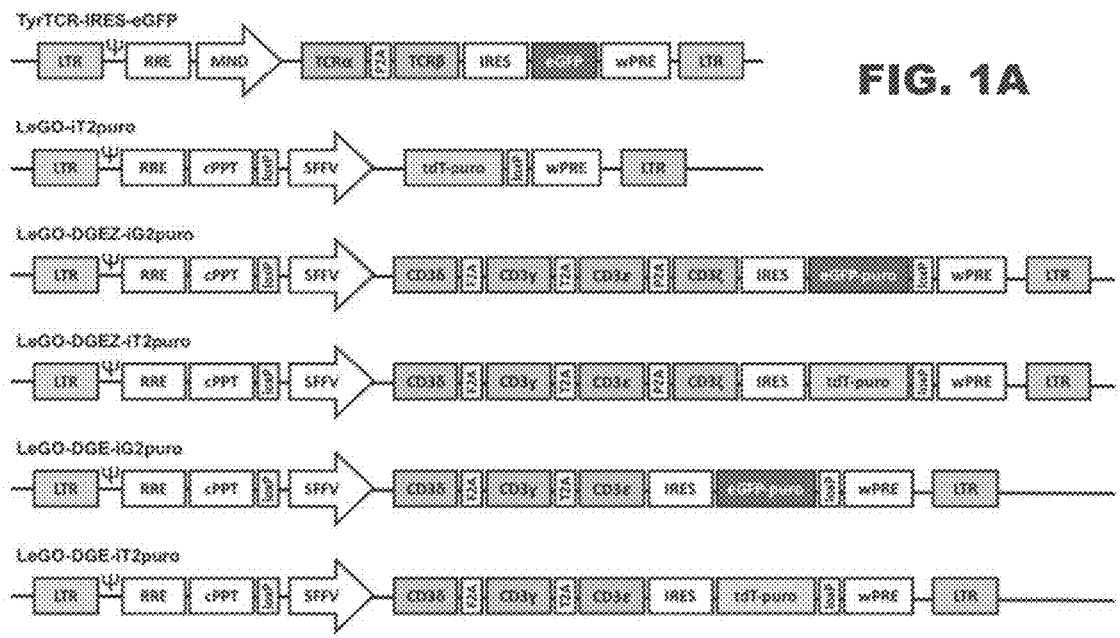
FIGS. 1A-C show that TCR introduction mediates surface CD3e expression on NK cells.

For the expression of TCR on the NK92 cell surface, two sets of lentiviral constructs were used (FIG. 1A).

For the expression of TCR sequences, the lentiviral TyrTCR-IRES-eGFP (TyrTCR) vector developed by Brusko et al. (27, 28) was used that codes for a co-receptor independent TCR against the melanoma antigen "tyrosinase" presented in the context of HLA-A*0201. For expression of CD3 chains, codon optimized sequences linked with 2A sequences were synthesized by Genscript (NJ, USA). These genes were cloned into LeGO backbone with eGFP or tdTomato fluorescent markers fused to puromycin resistance gene.

Figure 1B:
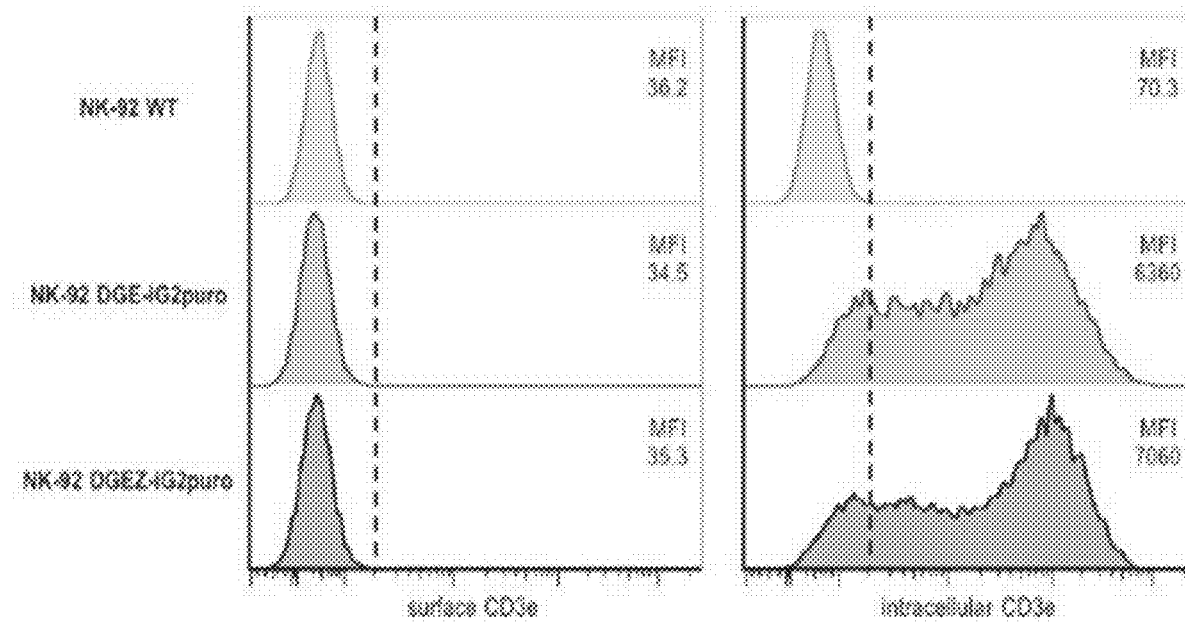

Initially, the expression levels of CD3ε on NK92 cells were determined by flow cytometry. NK92 cells do not express CD3ε molecule on the cell surface however in line with Lanier et al., there is trace amounts of intracellular CD3ε expression on NK92 cells. When NK92 cells are transduced with DGE or DGEZ vectors (NK92-DGE-iG2puro and NK92-DGEZ-iG2puro, respectively) surface expression of CD3ε was still absent as analyzed by flow cytometry. However, intracellular staining showed a high level of CD3ε expression in transduced cells compared to WT NK92 cells (FIG. 1B). This suggests that despite high levels of vector-driven expression, CD3 chains of the TCR complex (or at least CD3ε) -similar to the case during T cell development cannot be stably expressed on the surface of NK92 cells in the absence of the TCR α/β chains.

Figure 1C:
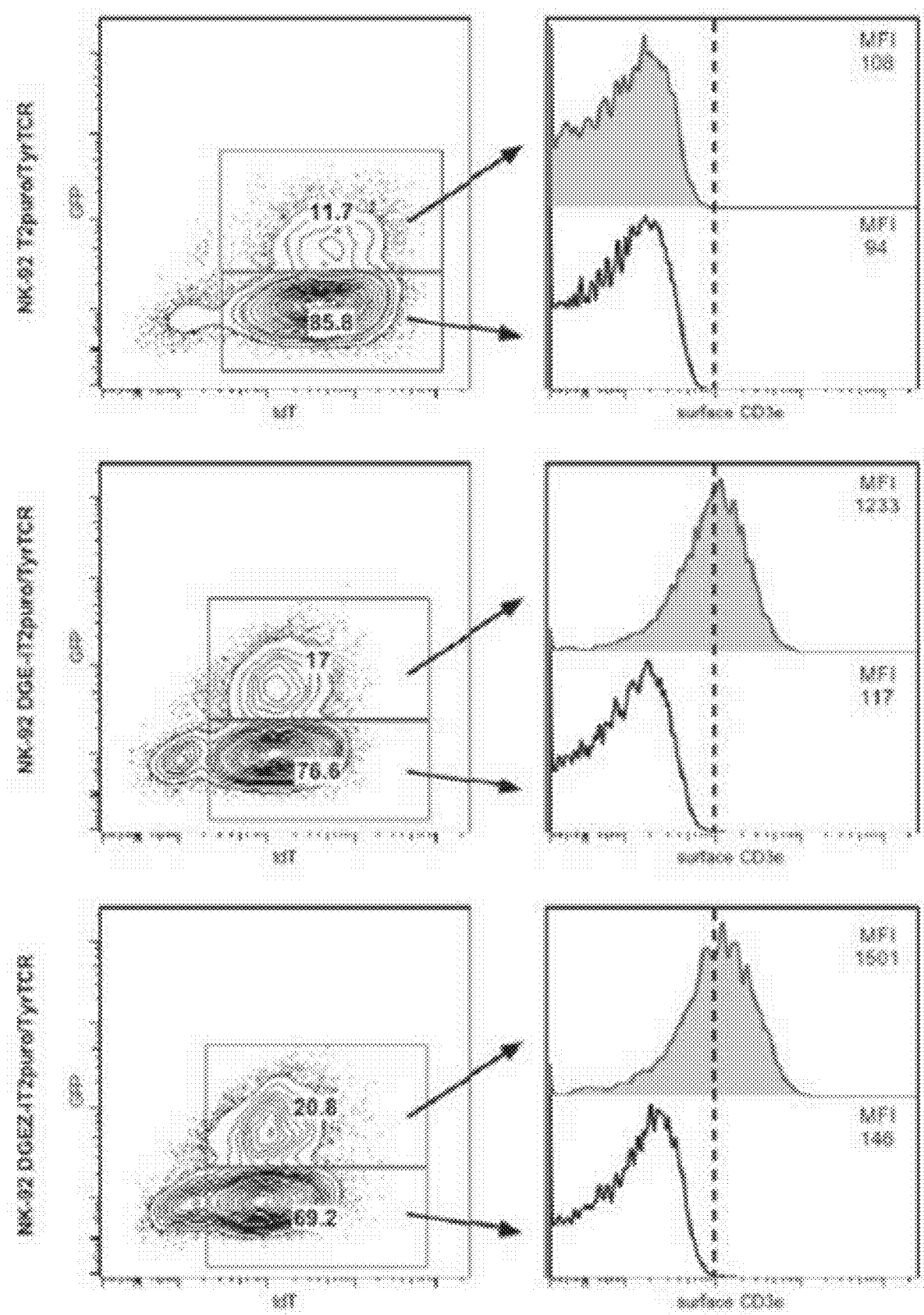

Furthermore, tyrosinase specific TCR was introduced to NK92 cells by a second lentiviral transduction with the TyrTCR vector. For this purpose, NK92 cells were first transduced with the LeGO-DGE-iT2puro or LeGO-DGEZ-iT2puro constructs as well as the empty LeGO-T2puro vector as a control and enriched with puromycin selection to <90% purity. Following puromycin selection, each cell line (NK92-T2puro, NK92-DGE-iT2puro, NK92-DGEZ-iT2puro) underwent a second transduction with the TyrTCR-IRES-GFP vector. In all cell lines, approximately 10-20% GFP positive cells 72 hours post-transduction were observed. Surface staining of these cells with anti-CD3ε antibody along with side-by-side analysis of the GFP+ and GFP- populations have revealed that surface CD3ε expression is only detectable where the CD3 chains are being ectopically expressed sideby-side with TCR α/β chains (FIG. 1C). In the absence of TCR α/β expression (GFPcells) no surface expression of CD3ε was observed despite the cells being tdT+. The inclusion of ectopic CD3ζ expression appears to minimally increase cell surface upregulation of CD3ε. This suggests that owing to the native CD3ζ expression in NK cells, the inclusion of CD3ζ ectopic expression is not crucial but an abundance of CD3ζ can increase the efficiency of TCR complex assembly at the cell surface. These results suggest that expression of at least CD3δ, CD3γ, CD3ε and TCR α/β heterodimer is necessary for establishment of TCR complex on the cell surface of NK92 cells.

Antigen Specificity of TCR Expressed on NK Cell Surface

As mentioned above TyrTCR is specific to tyrosinase protein derived peptide (368-379) YMDGTMSQV (Tyr368-379) (SEQ ID NO:1) in complex with HLA-A2. In order to determine cell surface expression of TyrTCR on NK92 cells and investigate whether or not TyrTCR retains its functionality and antigen specificity, NK92 cells were stained with Tyr368-379/HLA-A2 pentamers (FIGS. 2A-B). Tyr368-379/HLA-A2 pentamer staining on puromycin selected (tdT+) NK92 cells that are transduced with LeGO-T2puro, LeGO-T2puro/TyrTCR, LeGO-DGE-iT2puro/TyrTCR and LeGO-DGEZ-iT2puro/TyrTCR vectors revealed that only NK92 cells expressing TCR α/β together with the CD3 chains could be efficiently stained with the pentamer. Moreover, as the NK92-DGE-iT2puro/TyrTCR and NK92-DGEZ-iT2puro/TyrTCR cells express tdT and GFP fluorescent proteins, double positive cells were enriched (tdT+ GFP+) by fluorescence-activated cell sorting (FACS) (FIG. 2B). tdT+GFP+ enriched cells could be efficiently stained by tyrosinase pentamers (FIG. 2C).

In parallel with CD3ε cell surface expression patterns, only NK92-DGEiT2puro/TyrTCR and NK92-DGEZ-iT2puro/TyrTCR cells could be detected by the cognate Tyr368-379/HLA-A2 pentamer suggesting that expression and MHC binding of TyrTCR on the NK cell surface is dependent on the presence of the CD3 complex. Introduction of CD3 complex enables TCR trafficking to the cell surface and stable cell surface expression of TCR complex that results in antigen recognition.

NK cells Expressing TCR can Efficiently Degranulate against Target Cells Presenting Cognate Peptide MHC Complex.

Figure 3A:
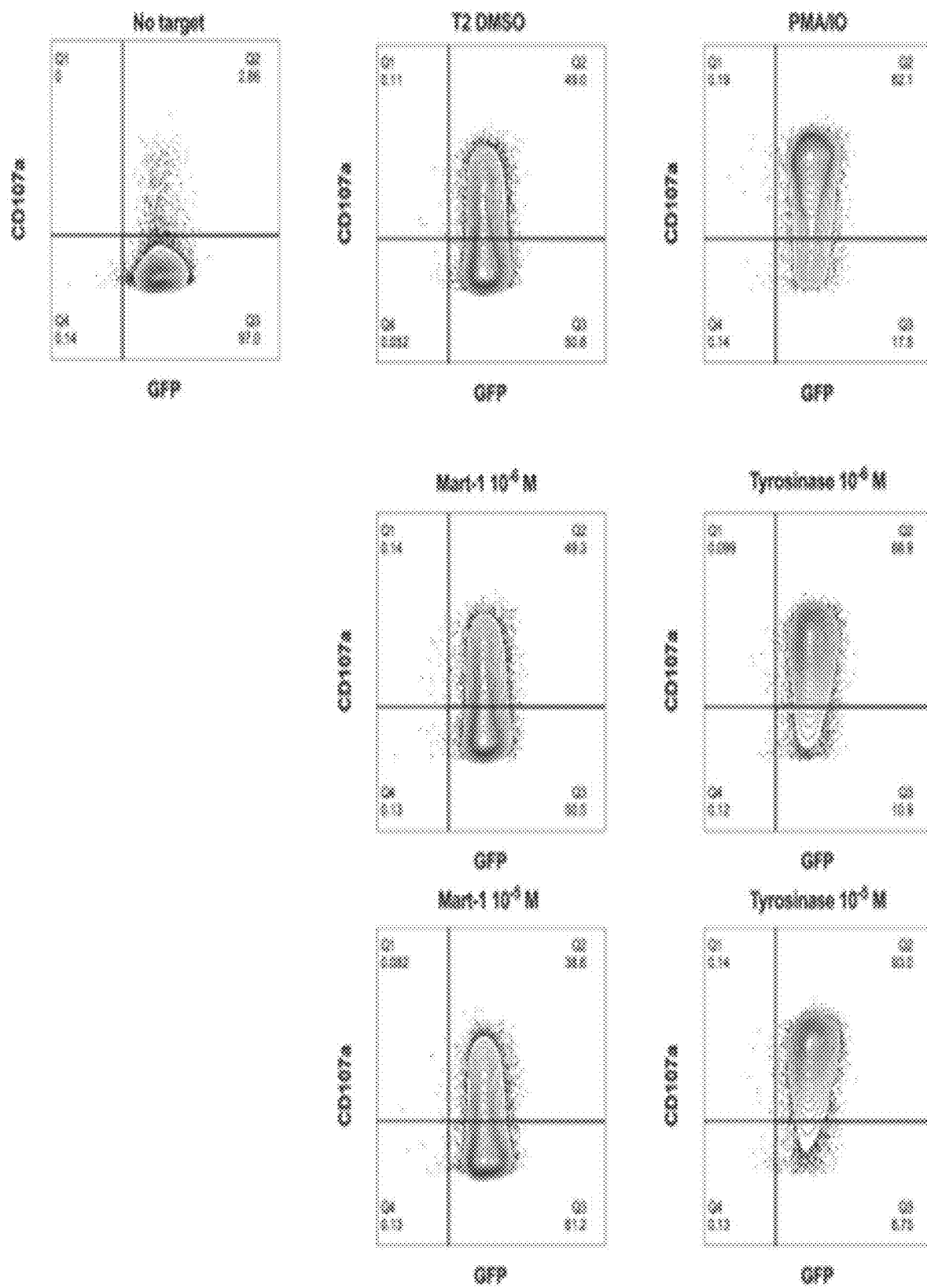
FIGS. 3A-C show that TCR complex expression on NK cells enhances antigen specific tumor responses.
Figure 3B:
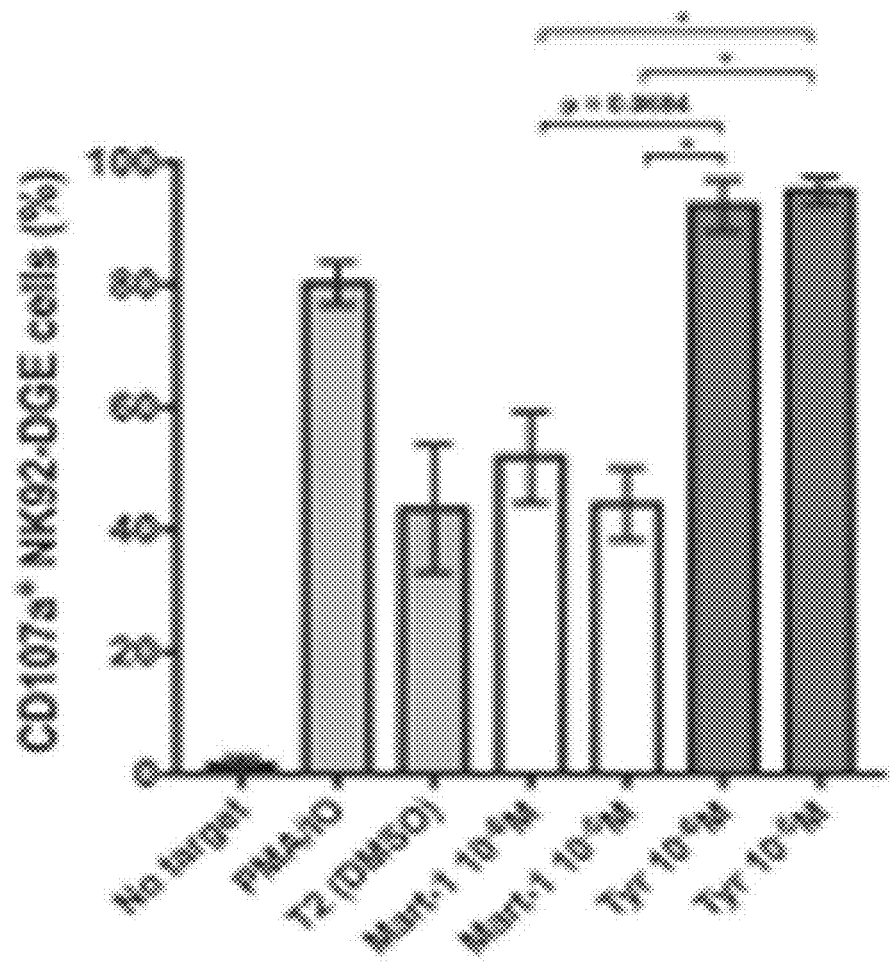
Figure 3C:
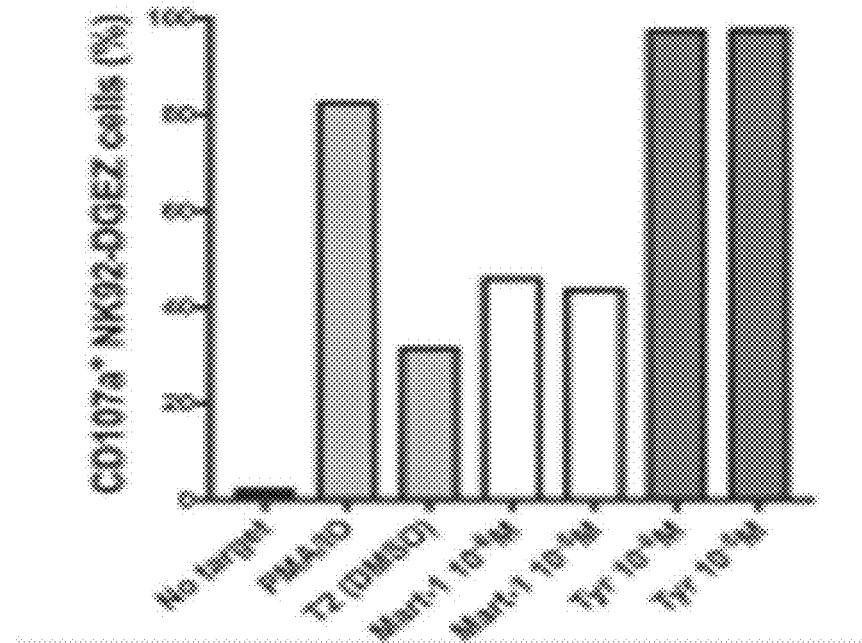

T cells scan the MHC/peptide (pMHC) population displayed on the cell surface of APCs through their extremely diverse TCRs that form a multi-subunit complex together with the signal transducing CD3 complex. Triggering of the TCR complex leads to the activation of various signaling and gene expression pathways resulting in T cell activation and the initiation of effector functions such as cytokine secretion, proliferation or the release of cytotoxic granules carrying perforin and granzyme resulting in target cell cytolysis. Similar to T cells, NK cells also deliver their cytotoxic molecules such as perforin and granzyme through releasing their pre-packed granules to the target cell. Degranulation of T and NK cells upon triggering can be detected through the transfer of Lamp-1 molecule (CD107a) to the cell surface during this process and it is also correlated with target cell cytolysis (Alter G, Malenfant J M, Altfeld M. CD107a as a functional marker for the identification of natural killer cell activity. Journal of immunological methods. 2004 November; 294(1-2):15-22). As natural killer cells already express a battery of T cell signaling molecules and share common cellular cytotoxicity mechanisms, it is essential to determine whether or not the introduction of CD3 complex together with TCR chains can result in efficient recognition of cognate pMHC ligand in the context of an encounter with target cells and if this recognition will trigger MHC-restricted antigen specific cellular cytotoxicity by NK cells. Therefore, degranulation capacity of TCR expressing NK cells was assessed against the HLA-A2 positive T2 cell line. As the T2 cell line is TAP-deficient, cell surface expression of HLA-A2 is very low and cell surface HLA-A2 levels can be upregulated by providing exogenous peptides, which sets a platform to study peptide specific T cell responses. Thus, degranulation of tdT+GFP+NK92-DGEiT2puro/TyrTCR and NK92-DGEZ-iT2puro/TyrTCR cell lines against T2 cells alone or loaded with Tyr368-379 as well as with an HLA-A2 restricted tumor associated antigen(Mart-1) derived epitope that cannot be recognized by TyrTCR was investigated (FIGS. 3A-C). Both NK cell lines degranulated against non-loaded (DMSO) T2 cells and Mart-1 loaded T2 cells similarly, on the other hand, T2 cells loaded with Tyr368-379 peptide triggered degranulation of both NK cell lines significantly higher than Mart-1 loaded T2 cells (FIGS. 3A-C). Most interestingly, in all independent experiments the amount of degranulation by the TCR expressing NK cells against Tyr368-379 loaded T2 cells were higher than PMA/Ionomycin triggered degranulation which is used as a positive control. Under these conditions, no difference in the capacity of degranulation between the two cell lines was observed which suggests that native levels of CD3ζ expression in NK92 cells is sufficient for the functionality of the introduced TCR.

Taken together, NK cells expressing CD3γ, CD3δ, CD3ε and TCR on their cell surface could detect an antigenic peptide presented by MHC-I and most importantly these cells could specifically detect cells presenting its cognate antigen as well as selectively degranulate against these cells. Expressing functional TCR on NK cells stands out as a unique discovery combining robust and effective cytotoxic capacity of NK cells with exclusive antigen specificity of T cells as a novel approach to develop cell-based immunotherapy of cancer and potentially viral infections such as HIV.

In this study, it was shown, for the first time, that the functional expression of a TCR on NK cells circumvents risks related to TCR mispairing and supplies a new source of effector cells for TCR gene therapy applications. The results show that lentiviral vector mediated ectopic expression of the CD3 γ, δ and ε chains along with TCR α/β gene delivery is sufficient for functional expression of a TCR directed against tyrosinase derived peptide Tyr368-379 presented in the context of HLA-A2. It was observed that neither the TCR α/β heterodimer, nor the CD3 subunits have the capacity to transport to the cell surface alone but can only form a stable complex when all components are present. TCR expressing NK92 cells robustly degranulated against T2 cells loaded with Tyr368-379 while no induction of degranulation was triggered in control Mart-1 peptide loaded T2 cells when compared to no peptide loading. These results provide a firm proof that TyrTCR expressed on the NK92 cell surface has the capacity to specifically recognize its cognate ligand on target cells and trigger cytotoxic response of NK92 cells. The two most common strategies for genetically targeting cytotoxic lymphocytes to specific antigens are the transfer of gene encoding TCR α/β heterodimers or CARs. The transfer of CAR genes into NK cells and their use in adoptive immunotherapy has been primarily tested in animal models and more recently in various clinical trials with promising results (Dahlberg C I, Sarhan D, Chrobok M, Duru A D, Alici E. Natural Killer Cell-Based Therapies Targeting Cancer: Possible Strategies to Gain and Sustain Anti-Tumor Activity. Frontiers in immunology. 2015; 6:605). Zhang et al. has recently reported the redirecting of NK92 cytotoxicity by genetic modification with a CAR derived from a TCR-like antibody against gp100/HLA-A2 complex (Zhang G, Liu R, Zhu X, Wang L, Ma J, Han H, et al. Retargeting NK-92 for anti-melanoma activity by a TCR-like single-domain antibody. Immunology and cell biology. 2013 November-December; 91(10):615-24). While Zhang also claims to confer TCR-like specificity to NK cells, in essence the approach used is a CAR design where the antibody sequence is fused to CD3ζ intracellular domain to turn the antibody into a receptor and signaling is mediated through CD3ζ alone in a classical 1st generation CAR design.

The inventive approach described herein provides a proof-of-principle for functional TCR expression on NK cells by making use of a TCR α/β heterodimer that functions independently of the co-receptors CD4 and CD8. While it remains unknown if co-receptor dependent TCRs will work in the same manner by using endogenous CD4 or CD8 expression in NK cells, it is also possible to include CD4 or CD8 in the design of the genetic modification process should that be necessary. Another parameter to optimize in the case of TCR expression on NK cells is whether there will be mutual interference of this modification with the mechanisms of missing self recognition (Ljunggren H G, Karre K. In search of the 'missing self': MHC molecules and NK cell recognition. Immunology today. 1990 July; 11(7):237-44) in NK cells. In the current experimental setting where T2 cells have almost no surface MHC expression due to TAP deficiency and NK92 cells have no KIR expression except for low levels of KIR2DL4 (Maki G, Klingemann H G, Martinson J A, Tam Y K. Factors regulating the cytotoxic activity of the human natural killer cell line, NK-92. Journal of hematotherapy & stem cell research. 2001 June; 10(3):369-83), it is not possible to make any statements about missing-self recognition. Regardless, a high rate of degranulation when WT NK92 cells are incubated with DMSO control T2 cells was observed, potentially due to CD40-CD40L interaction (Maki G, Klingemann H G, Martinson J A, Tam Y K. Factors regulating the cytotoxic activity of the human natural killer cell line, NK-92. Journal of hematotherapy & stem cell research. 2001 June; 10(3):369-83 and Carbone E, Ruggiero G, Terrazzano G, Palomba C, Manzo C, Fontana S, et al. A new mechanism of NK cell cytotoxicity activation: the CD40-CD40 ligand interaction. The Journal of experimental medicine. 1997 Jun. 16; 185(12):2053-60). Despite this high background, TCR expression on NK92 cells is still able to mount an impressive degranulation response against peptide-loaded T2 cells at a rate that exceeds experimental positive controls.

Protocols: (Methods and Materials)

Cell Lines

293FT cells were maintained in Dulbecco's Modified Eagle Medium (DMEM) (GIBCO, Life Technologies, Grand Island, N.Y., USA) supplemented with 10% Fetal Bovine Serum (FBS) (GIBCO), 0.1 mM non-essential amino acids (Sigma-Aldrich, St. Louis, Mo., USA), 6 mM L-glutamine (Sigma-Aldrich), 1 mM sodium pyruvate (Sigma-Aldrich) and 20 mM HEPES (Sigma-Aldrich). NK92 cells were maintained in CellGro SCGM (Cellgenix) medium supplemented with 20% FBS and 1000 U/ml rhIL-2 (Proleukin, Novartis). T2 cells were maintained in RPMI-1640 medium (GIBCO) supplemented with 10% FBS.

Production of Lentiviral Vectors

For production of VSV-G pseudotyped lentiviral vectors, 14×10⁶ 293FT cells were plated into a poly-D-lysine coated 150 mm dish (BD Biosciences, San Jose, Calif., USA). Next day cells were transfected with 30 µg of vector plasmid (LeGO vectors courtesy of Prof. Boris Fehse, University Medical Center Hamburg-Eppendorf, Hamburg, Germany), 15 µg of pMDLg/pRRE (Addgene, Cambridge, Mass., USA), 10 µg of pRSV-REV (Addgene) and 5 µg of phCMV-VSV-G (Addgene) using calcium phosphate transfection kit (Sigma-Aldrich) in the presence of 25 µM Chloroquine (Sigma-Aldrich). 10 hours after transfection, the medium was changed and thereafter virus containing supernatant was collected every 24 hours for 2 days and stored in −80° C. until further use. A small aliquot from each production was used to determine viral titers by transduction of 293FT cells with serially diluted amounts of virus supernatant.

Lentiviral Transduction of NK92 Cells

For each lentiviral transduction, 0.25×10⁶ NK92 cells per well were seeded in a 24-well plate (BD Biosciences) and mixed with an appropriate amount of virus supernatant in the presence of 8 µg/ml of protamine sulfate and 3 µM BX795 (Sigma-Aldrich) in a final volume of no more than 1 ml. The plates were incubated at 37° C., 5% CO2 for 6 hours. At the end of the incubation, cells were spinned down at 300×g for 10 minutes at room temperature after which the supernatants were removed from the wells and 1 ml of fresh NK cell growth medium (CellGro SCGM supplemented with 10% Human AB Serum) per well was added. The cells were maintained in this medium with daily addition cytokines IL-2 for at least 3 days before acquisition of gene expression was carried out.

Flow Cytometry

All antibody stainings for flow cytometry were done according to the following protocol: For surface stainings, the cells were washed once with PBS and incubated with appropriate amounts of antibody at 4° C. for 30 min. The labeled cells were then washed with PBS and data acquisition was done on a FACSCanto (BD Biosciences) flow cytometer with standard filters. The antibodies used for NK cells were CD56 (NCAM16.2) and CD3ε (SK7) from BD Biosciences. For intracellular staining, cells were fixed and permeabilized for 15 minutes in a solution containing 2% PFA in 1× Permeabilization Wash Buffer (BioLegend), washed two times with Permeabilization Wash Buffer and incubated with appropriate amounts of antibody at 4° C. for 30 min. The labeled cells were then washed with Permeabilization Wash Buffer and data acquisition was carried out. Data were analysed with the FlowJo software (TreeStar Inc.).

Peptides and HLA A2 Pentamers

Tyrosinase(368-379) and Melan-A/Mart-1(27-35) peptides (SEQ ID NOS. 1 and 2) as well as APC conjugated Tyrosinase(368-379)/HLA-A2 pentamers were purchased from ProImmune Ltd (Oxford, UK). 0.5×10⁶ NK-92 cells were washed once with PBS and incubated with 10 ul of Tyrosinase(368-379)/HLA-A2 pentamers at 4° C. for 30 min. The labeled cells were then washed PBS twice and data acquisition was carried out. Data were analysed with the FlowJo software (TreeStar Inc.).

Analysis of NK Cell Degranulation

TAP-deficient T2 cells were pulsed with different concentrations of indicated peptides in serum free RPMI medium at 26oC overnight in 5% CO2. Cells were subsequently washed and incubated in RPMI medium at 37° C. for 60 min. Then, NK92 cells were co-incubated with T2 target cells at a ratio of 1:1 in a final volume of 200 µl in round-bottomed 96-well plates at 37° C. and 5% CO2 for 6 h. Fluorochrome-conjugated anti-CD107a mAb was added at the initiation of the assay. After 1 h of coincubation, Monensin (BioLegend) was added at a 1:100 dilution. The cells were then washed, resuspended in ice-cold PBS and immediately analyzed by flow cytometry.

Statistical Analysis

For preparation of graphs and statistical analysis, GraphPad Prism (GraphPad Software Inc. La Jolla, Calif., USA) was used.

Study 2:

For further analysis of TCR assembly on the NK cell surface and optimization of TCR expression, NK cell lines NK-92 and YTS were used as model systems. TCR α/β expressing vectors were delivered into NK cells, along with lentiviral vector-based expression of CD3δ, CD3γ, and CD3ε in the presence and absence of CD3ζ (which is readily expressed in NK cells) to observe TCR assembly on the NK cell surface (FIGS. 4A-E).

For the expression of CD3 chains in NK cells two different lentiviral constructs were used, one with and the other without the CD3ζ chain (FIG. 4A). Codon optimized CD3 chains linked with 2A sequences were synthesized and were cloned into LeGO backbone with tdTomato fluorescent marker fused to puromycin resistance gene. The expression of TCR α/β sequences was done with the lentiviral TyrTCR-IRES-eGFP (TyrTCR) vector developed by Brusko et al.

(Brusko T M, Koya R C, Zhu S, Lee M R, Putnam A L, McClymont S A, et al. Human antigen-specific regulatory T cells generated by T cell receptor gene transfer. PLoS One. 2010; 5(7):e11726 and Roszkowski J J, Yu D C, Rubinstein M P, McKee M D, Cole D J, Nishimura M I. CD8-independent tumor cell recognition is a property of the T cell receptor and not the T cell. J Immunol. 2003 Mar. 1; 170(5):2582-9) that codes for a co-receptor independent TCR against the melanoma antigen tyrosinase derived peptide (368-379) YMDGTMSQV (Tyr$_{368}$-379) (SEQ ID NO:1) in complex with HLA-A*0201.

Initially, the presence of surface CD3ε on NK-92 cells was analyzed by flow cytometry (FIG. 4B, left panel). When NK-92 cells are transduced with DGE-iT2puro or DGEZ-iT2puro vectors, surface expression of CD3ε was absent as analyzed by flow cytometry. However, intracellular staining showed a high level of CD3ε expression in transduced cells compared to control NK-92 T2puro cells (FIG. 4B, right panel). This suggests that despite high levels of vector-driven expression, CD3 chains of the TCR complex—similar to the case during T cell development—cannot be stably expressed on the surface of NK-92 cells in the absence of the TCR α/β chains.

Figure 4C:
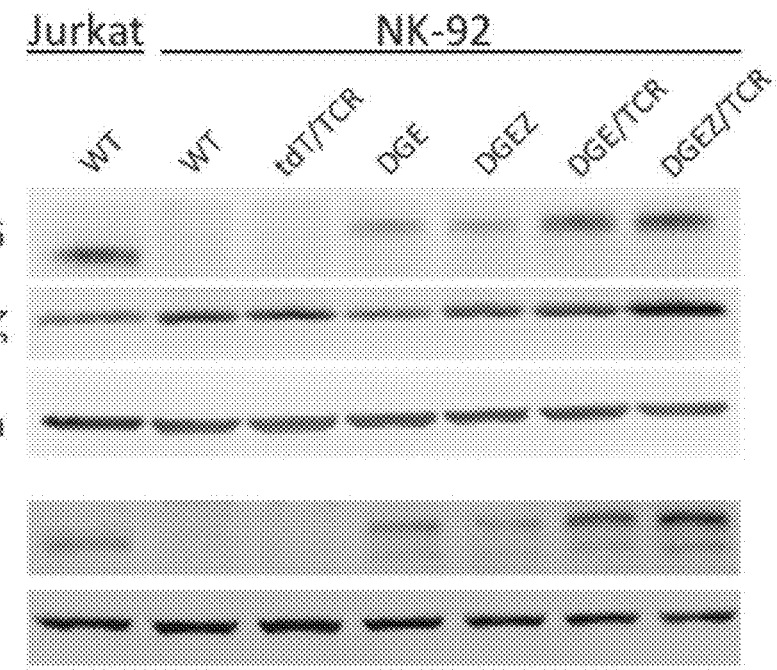
Figure 4D:
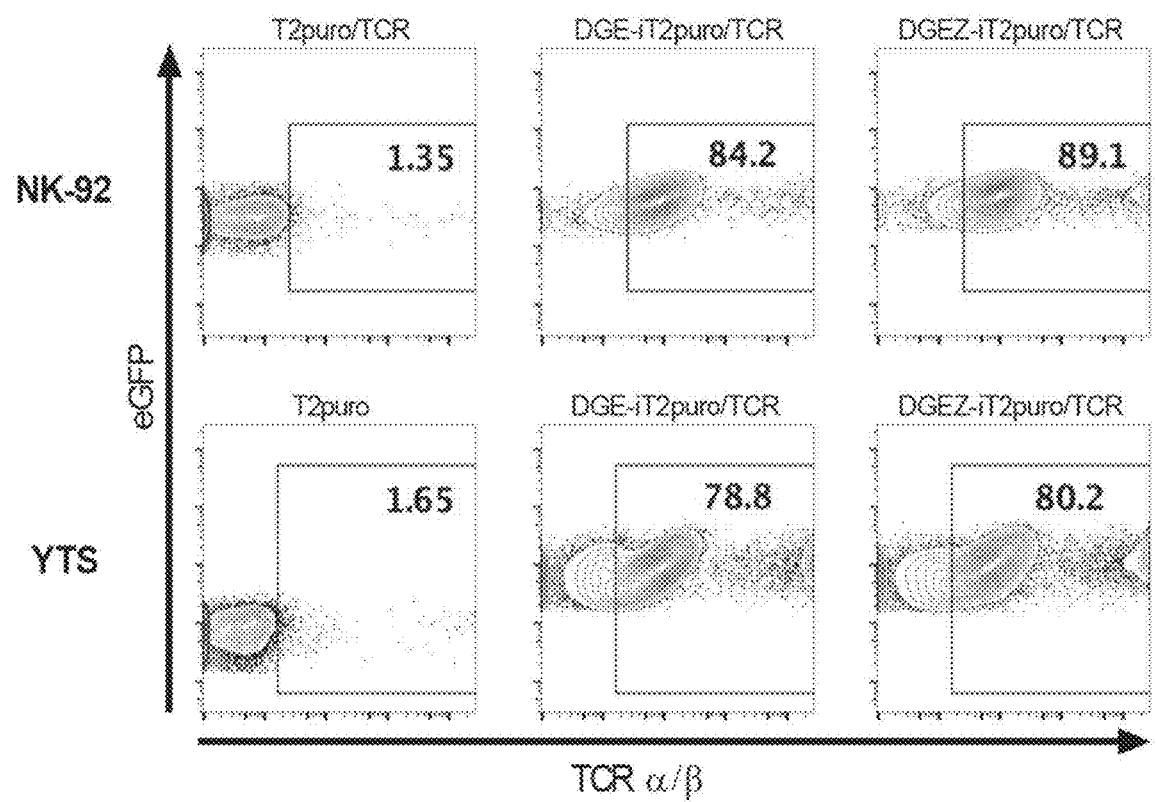
Figure 30:
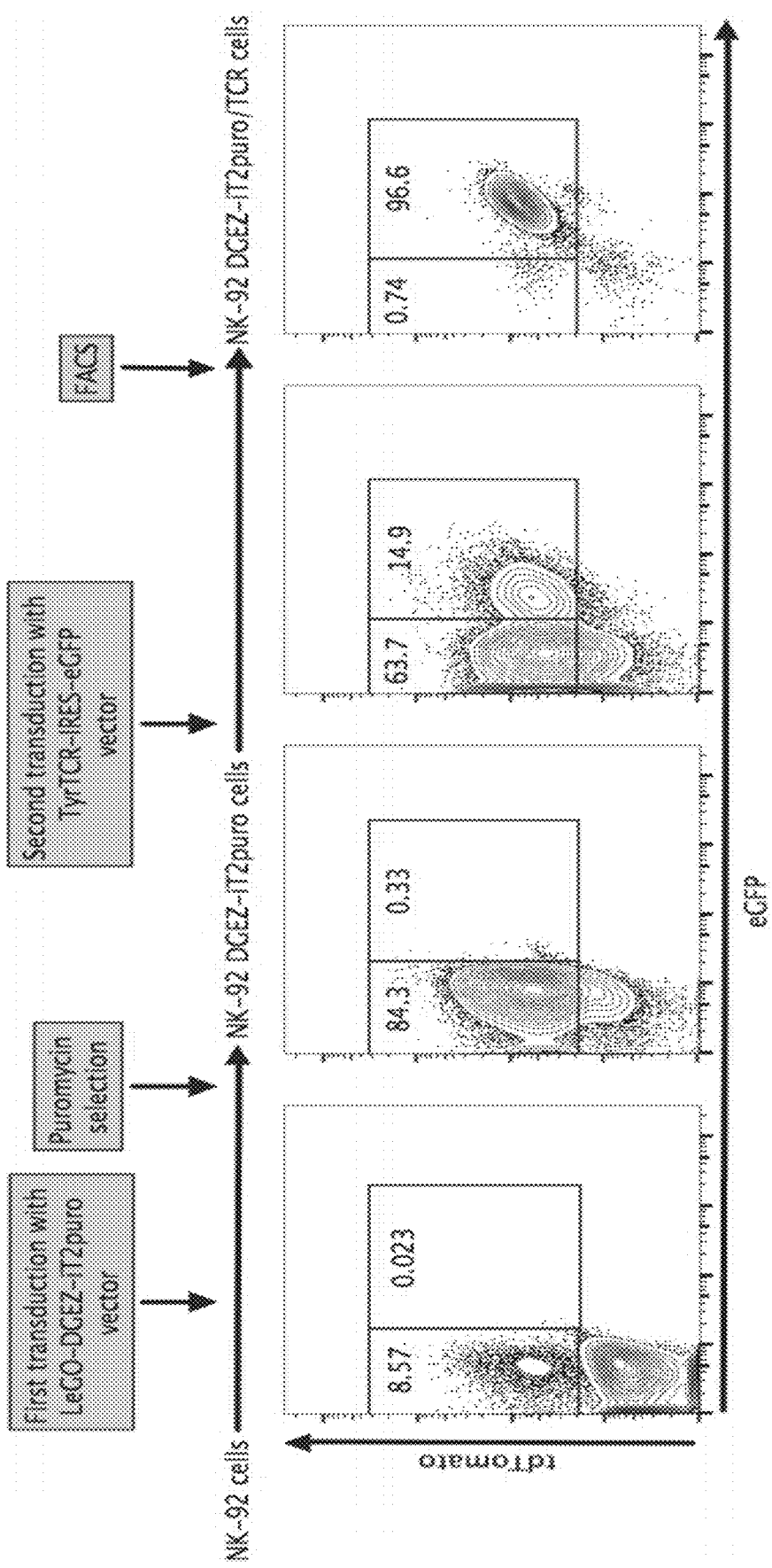
FIG. 30 is a schematic illustration of the procedure for the genetic modification of the NK cells and YTS cells.

Furthermore, tyrosinase specific TCR was introduced to NK-92 cells by a second lentiviral transduction with the TyrTCR vector. For this purpose, NK-92 cells were first transduced with the LeGO-DGE-iT2puro or LeGO-DGEZ-iT2puro constructs as well as the empty LeGO-T2puro vector as a control and enriched with puromycin selection to <90% purity. Then, each cell line (NK-92 T2puro, NK-92 DGE-iT2puro, NK-92 DGEZ-iT2puro) underwent a second transduction with the TyrTCR-IRES-GFP vector. In all cell lines, approximately 10-20% GFP positive cells were observed 72 hours post-transduction, which were then subjected to fluorescence-activated cell sorting (FACS) for purification. Surface staining of these cells with anti-CD3ε antibody revealed that surface CD3ε expression is only detectable where the CD3 chains are being ectopically expressed side-by-side with TCR α/β chains (FIG. 4B). In the absence of TCR α/β expression no surface expression of CD3ε is observed despite the cells expressing tdTomato from the CD3 constructs. The inclusion of ectopic CD3ζ expression appears to minimally increase cell surface expression of CD3ε. This suggests that owing to the native CD3ζ expression in NK cells, the inclusion of CD3ζ ectopic expression is not crucial but an abundance of CD3ζ can increase the efficiency of TCR complex assembly at the cell surface. The expression of CD3δ, CD3γ, and CD3ζ in the WT (wildtype) and genetically-modified cells were also characterized with western blot analysis (FIG. 4C). The procedures for modification of the cells is illustrated in FIG. 30.

Figure 4E:
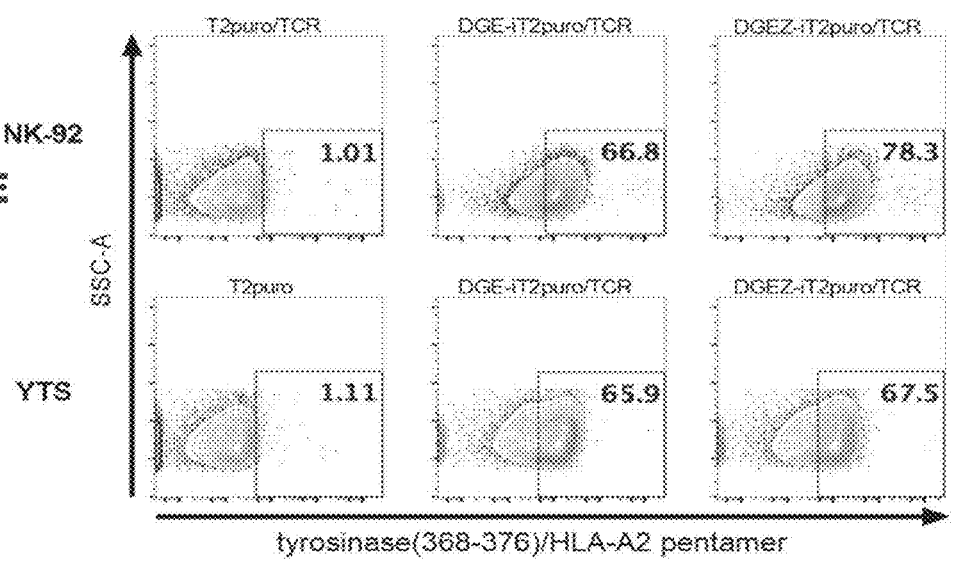

In order to further determine cell surface expression of TyrTCR on NK cells, genetically modified NK-92 and YTS cells were stained with anti-TCR α/β antibody (FIG. 4D) as well as Tyr$_{368-379}$/HLA-A2 pentamers (FIG. 4E). These results also confirmed that only NK cells expressing TCR α/β together with the CD3 chains could be efficiently stained with anti-TCR α/β antibody or Tyr$_{368-379}$/HLA-A2 pentamer.

These results suggest that the ectopic expression of CD3δ, CD3γ, CD3ε and TCR α/β heterodimer but not CD3ζ is necessary for establishment of TCR complex on the surface of NK-92 and YTS cells.

To test for antigen-specific triggering, degranulation capacity of TCR expressing NK cells against the HLA-A2$^+$ T2 cell line was assessed (FIGS. 5A-F, FIG. 20, and FIG. 21). A T2 peptide binding assay was used. The T2 is a T cell leukemia cell line having expression of HLA-A2. Although T2 cell lines are deficient in TAP, the cells still express low amounts of MHC-class I on the surface. The T2 binding assay is based upon the ability of peptides to stabilize the MHC-class I complex on the surface of the T2 cells. Further, since the T2 cell line is TAP-deficient, cell surface expression of HLA-A2 is very low and cell surface HLA-A2 levels can be upregulated by providing exogenous peptides, which sets a platform to study peptide specific T cell responses. Thus, degranulation was investigated against T2 cells alone or loaded with Tyr$_{368-379}$ as well as with an HLA-A2 restricted tumor associated antigen (Mart-1) derived epitope that should not be recognized by TyrTCR.

Figure 5A:
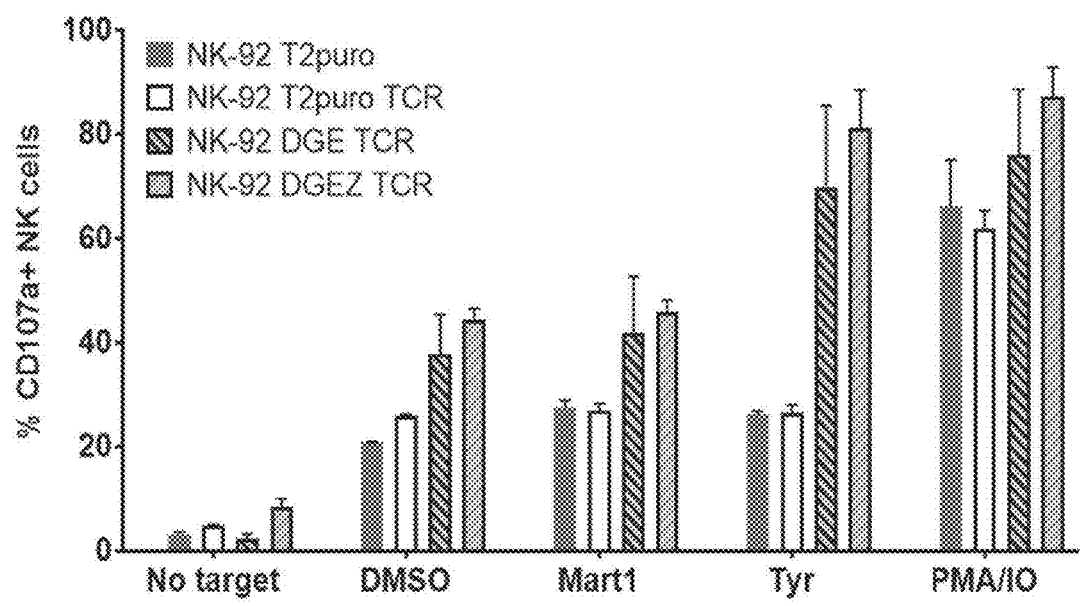
FIGS. 5A-F show that TCR complex expression on NK cells enables antigen specific triggering. To assess NK cell degaranulation capacity, cell surface expression levels of CD107a on NK cells is measured upon target cell exposure. T2 cells loaded with indicated peptides or DMSO (empty) is mixed with transgenic NK-92 cells (FIG. 5A) or YTS cells (FIG. 5B) at 1:1 ratio for 5 hours. After 1 hour of co-incubation Golgi stop was added. T2 cells loaded with indicated peptides or DMSO (empty) are mixed with NK-92 DGE-iT2/TCR cells (FIG. 5C) or NK-92 DGEZ-iT2/TCR cells (FIG. 5D) at 1:1 ratio. Cell surface expression of CD107a is measured at indicated time points with flow cytometry. Target cells including A375, A375 (TYR) and K562 cells were coincubated with transgenic NK-92 cells (FIG. 5E) or YTS cells (FIG. 5F) at 1:1 ratio for 5 hours. Degranulation capacity of cells were assessed by flow cytometry.

In the case of NK-92 cells, both DGE-iT2puro/TCR and DGEZ-iT2puro/TCR expressing cells degranulated against non-loaded (DMSO) and Mart-1 loaded T2 cells similarly and at a slightly higher level than control cells expressing only T2puro or T2puro/TCR. On the other hand, T2 cells loaded with Tyr368-379 peptide triggered degranulation of both NK cell lines at a significantly higher level (FIG. 5A).

Figure 5B:
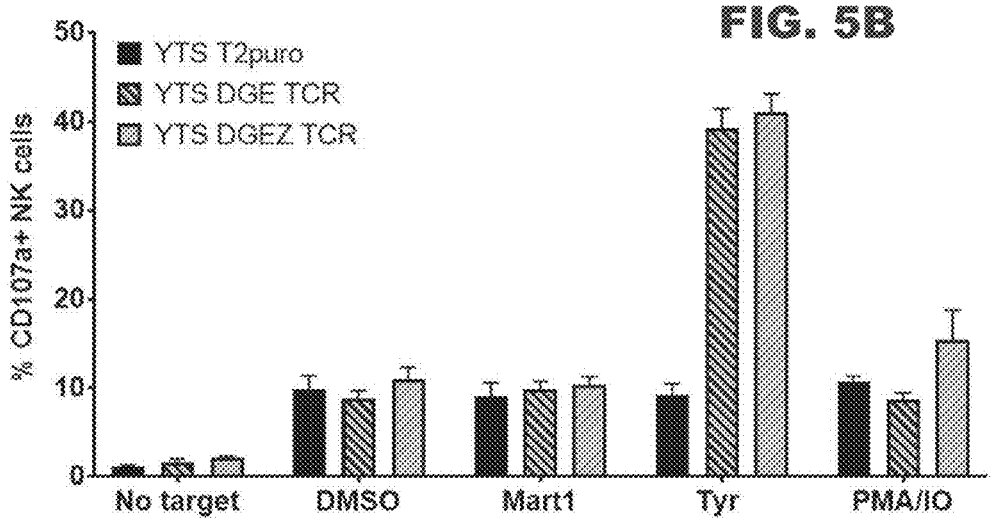

With YTS cells, a response to PMA/Ionomycin was not observed, but a similar trend was seen against T2 targets where only background levels of degranulation were present against DMSO controls or Mart-1 peptide loaded cells while a high response to Tyr peptide loaded T2 cells were recorded in both DGE-iT2puro/TCR and DGEZ-iT2puro/TCR expressing cells (FIG. 5B).

Figure 5C:
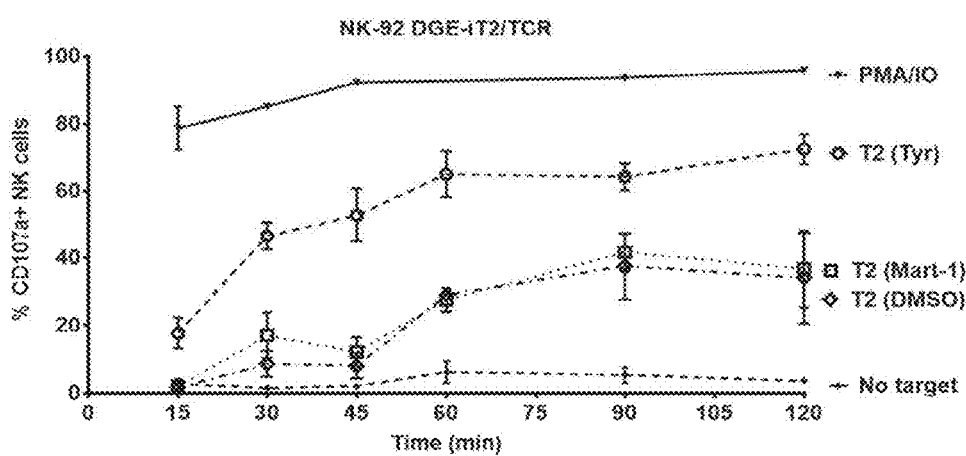
Figure 5D:
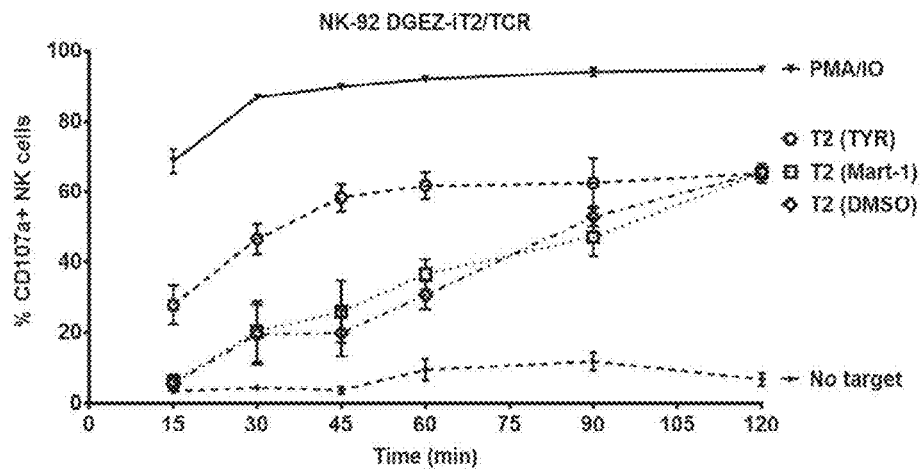

Analysis of the dynamics of degranulation during the first two hours of contact with peptide loaded T2 target cells has shown that the TCR-triggered response of NK-92 cells is extremely fast with significant antigen-specific responses seen as early as 15 minutes (FIGS. 5C-D).

It was noticed that the triggering of DGEZ-expressing cells seems to have lost a certain degree of specificity against Tyr peptide loaded cells and shows higher activity against non-specific targets. It was hypothesized that this could be due to the overexpression of CD3ζ chain effecting expression of NK cell activating receptors natively coupled with this signaling adaptor.

Figure 5E:
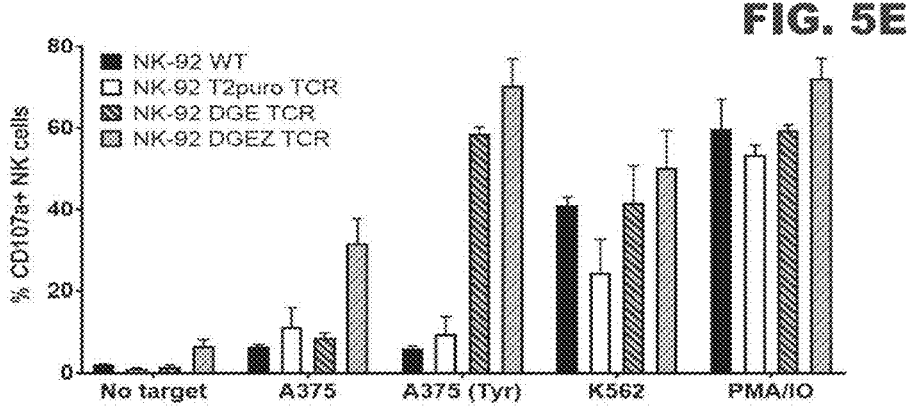
Figure 5F:
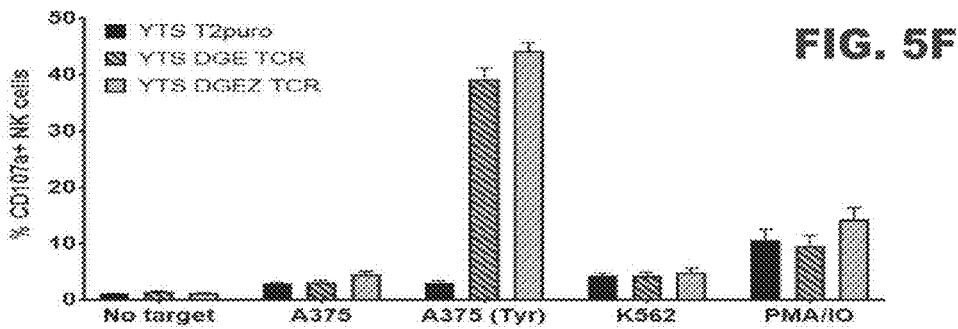

Besides investigating the triggering by peptide loaded cells, whether the TyrTCR introduced by genetic modification has the capacity to recognize endogenously processed peptides in complex with HLA-A2 also was investigated (FIGS. 5E-F). For this purpose, the HLA-A2$^+$ melanoma cell line A375 was used and a version of the same cell line that overexpresses the tyrosinase protein A375(Tyr) was used. Degranulation against A375(Tyr) targets in both NK-92 and YTS cells were quite efficient and proved that the introduced TCR can recognize endogenously processed epitopes. On the other hand, the background degranulation of DGEZ-iT2PURO/TCR expressing cells against A375 targets that do not express the tyrosinase protein were elevated, correlating with results from degranulation against peptide loaded T2 cells and hinting at a loss of specificity when CD3zeta chain is overexpressed.

When comparing the degranulation of DGE and DGEZ expressing cells under these conditions, no difference against Tyr peptide-loaded T2 cells or A375(Tyr) cells was observed which suggests that native levels of CD3ζ expression in NK cells is sufficient for the functionality of the introduced TCR.

Taken together, these data suggest that NK cells expressing CD3δ, CD3γ, CD3ε and TCRα/β on their cell surface could detect an antigenic peptide presented by MHC-1 and selectively degranulate against these cells. The inclusion of CD3δ in vector design does not seem to help increase antigen-specific triggering but on the contrary, might increase background activity against non-specific targets.

Figure 6A:
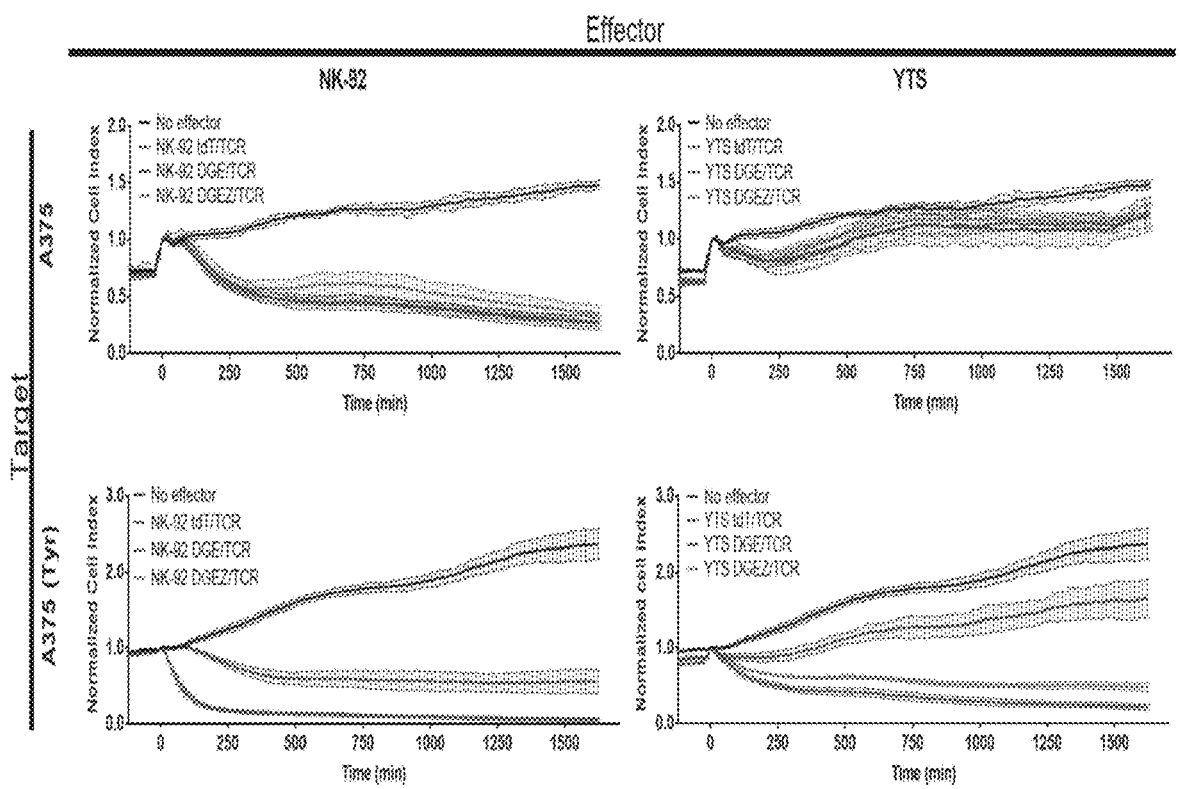
FIGS. 6A-D show cytotoxic activity of TCR gene modified NK cells against the A375 cell line.
Figure 6B:
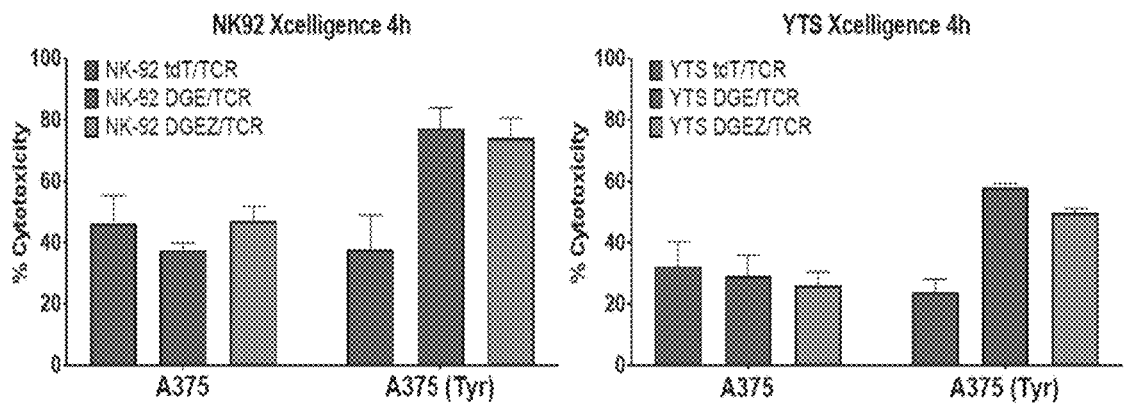
Figure 6C:
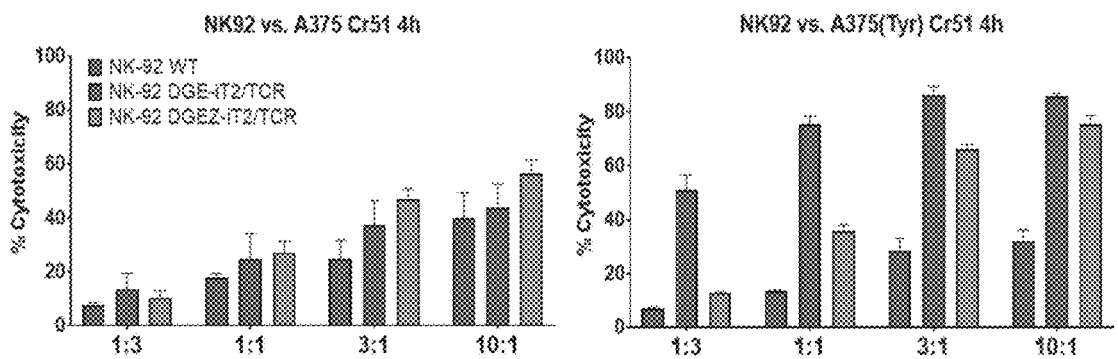
Figure 12:
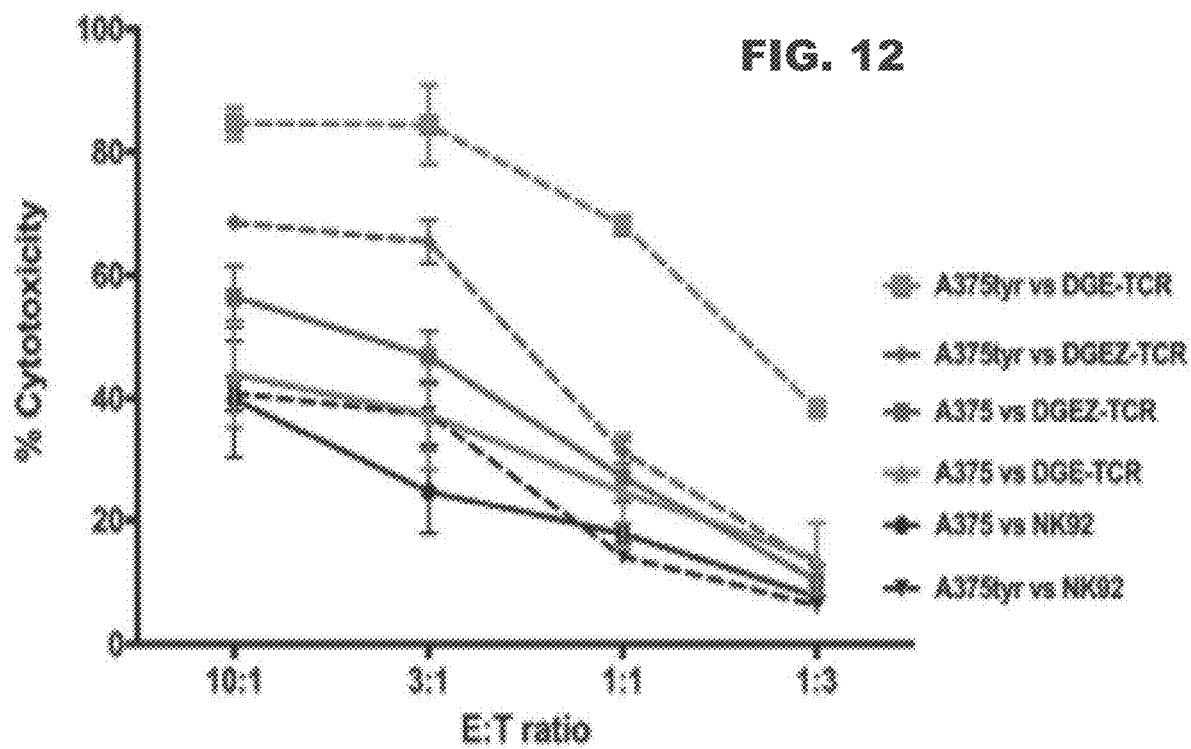
FIG. 12 shows E:T ratio dynamics of cytotoxic activity of NK-TCR cells against A375 and A375(Tyr) cells.

As the definite demonstration of antigen-specific triggering, cytotoxic activity of genetically modified NK-92 and YTS cells against A375 and A375(Tyr) targets was analyzed (FIG. 12). Electrical impedance-based analysis of A375 and A375(Tyr) cell growth using the XCelligence® RTCA instrument in the presence/absence of effector cells has revealed that both NK-92 and YTS cells efficiently kill tyrosinase expressing targets (FIGS. 6A, 28A-B, and 29A-B) upon specific TCR expression. Quantification of cytotoxic activity as measured by XCelligence® RTCA at the 4 h timepoint (FIG. 6B) shows high cytotoxic activity against A375(Tyr). Standart 4 h $^{51}$Cr-based cytotoxicity with NK-92 cells against A375 and A375(Tyr) also confirms these observations (FIG. 6C). 6cDGE-iT2puro/TCR cells show higher antigen-specific cytotoxic activity than DGEZ-iT2puro/TCR cells despite their slightly lower degranulation rate while DGEZ-iT2puro/TCR cells show signs of elevated activity against the background A375 cells without Tyr expression. These effects also seem to be reproducible in the case of YTS cells where the overexpression of CD3ζ negatively affects antigen-specificity of responses.

Figure 6D:
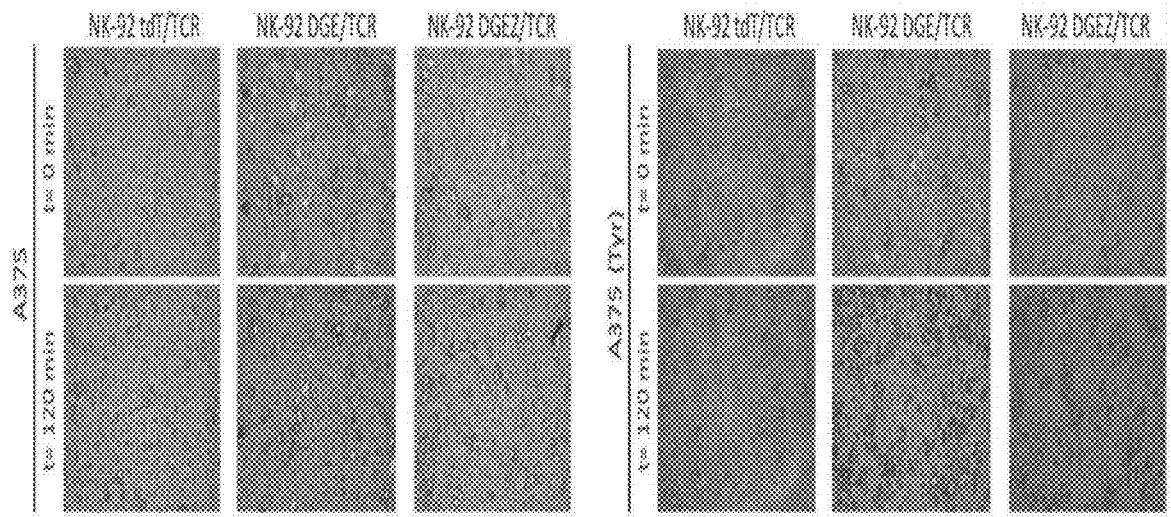
Figure 8A:
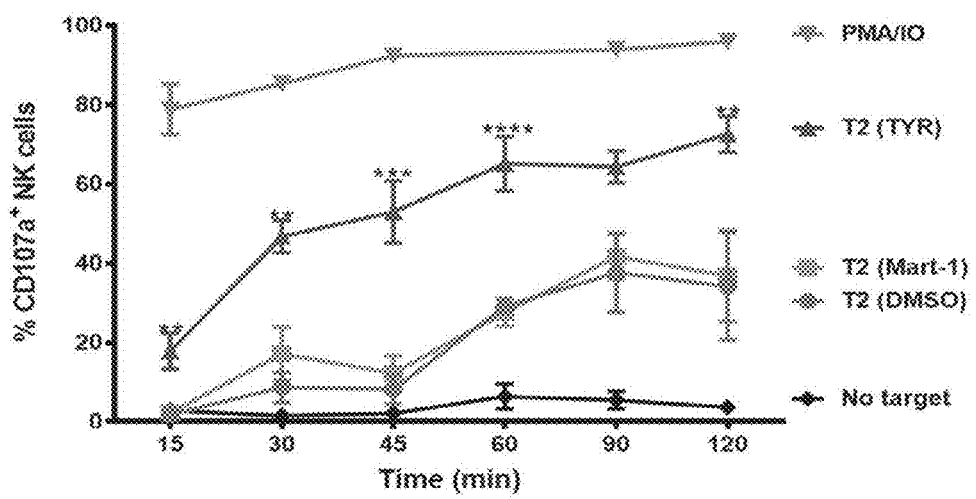
FIGS. 8A-B show the dynamics of CD107a degranulation of Nk-TCR cells against T2 cells.
Figure 8B:
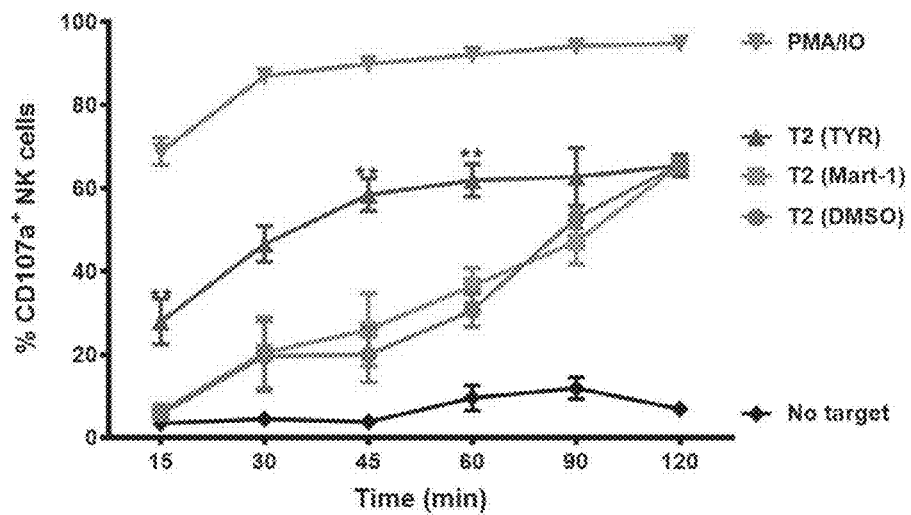
Figure 9A:
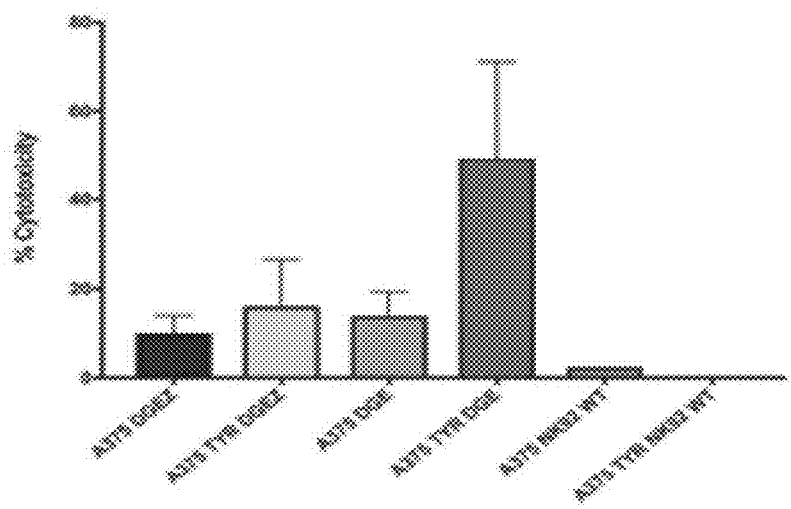
FIGS. 9A-F show cytotoxic activity of NK-TCR cells against A375, A375(Tyr), T2, and K562 cells.
Figure 9D:
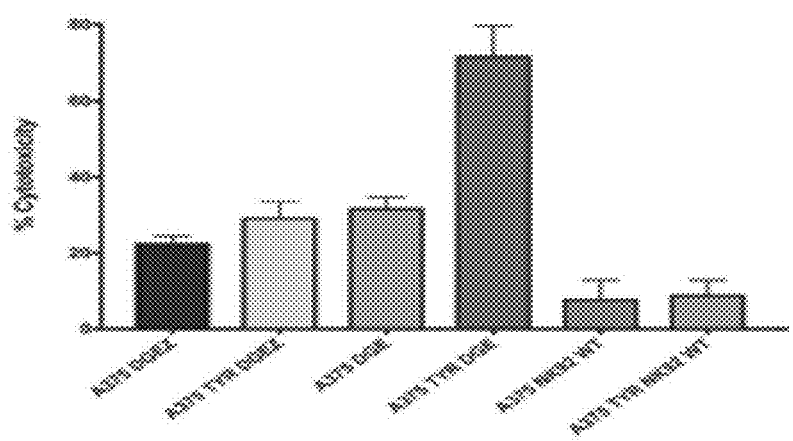
Figure 9B:
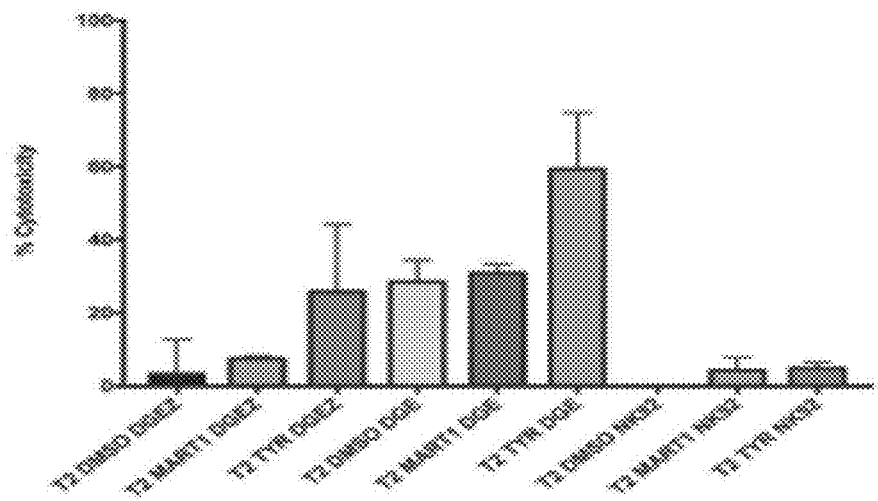
Figure 9E:
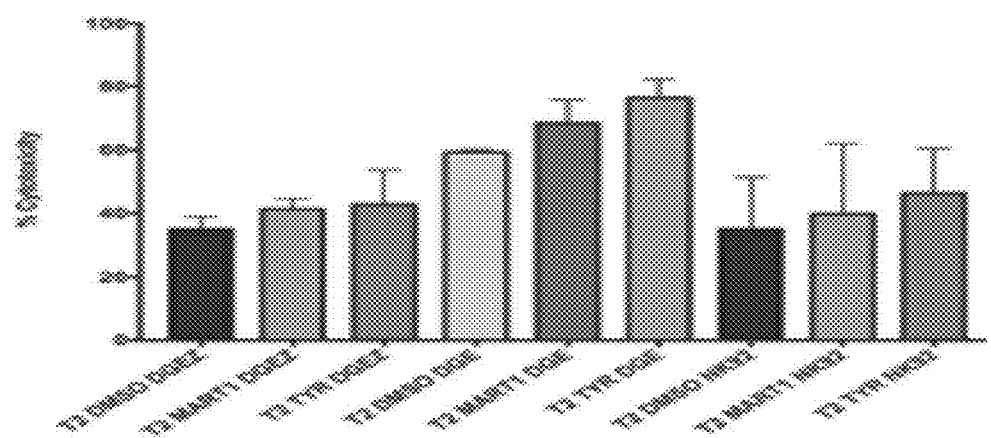
Figure 9C:
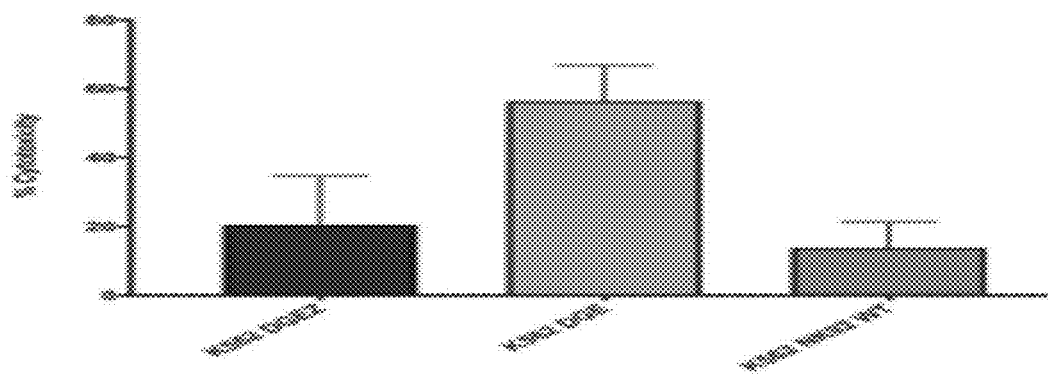
Figure 9F:
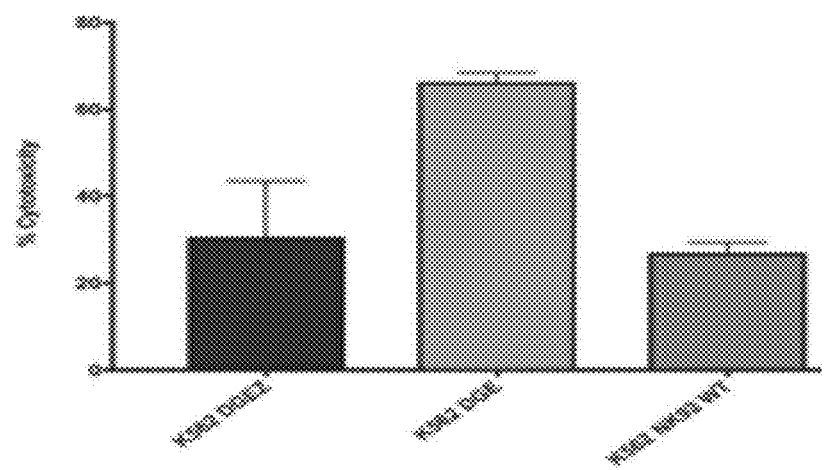
Figure 10A:
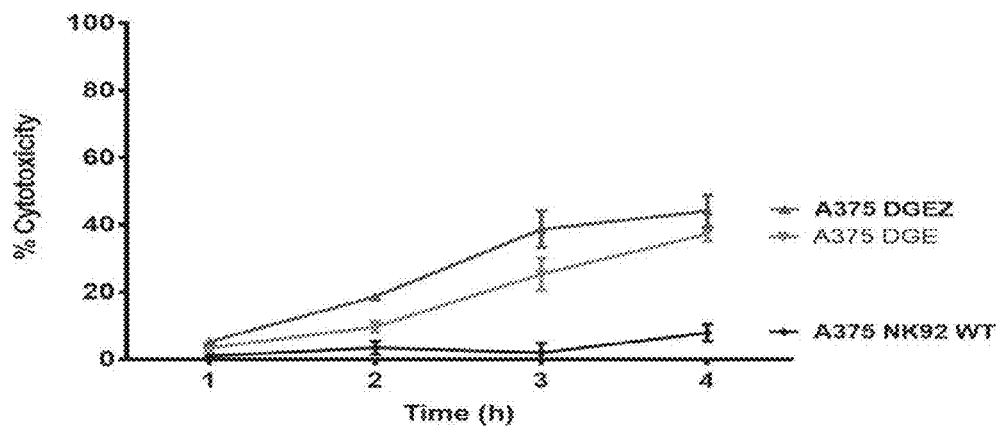
FIGS. 10A-F show kinetics of cytotoxic activity of NK-TCR cells against A375 and A375(Tyr) cells.
Figure 10B:
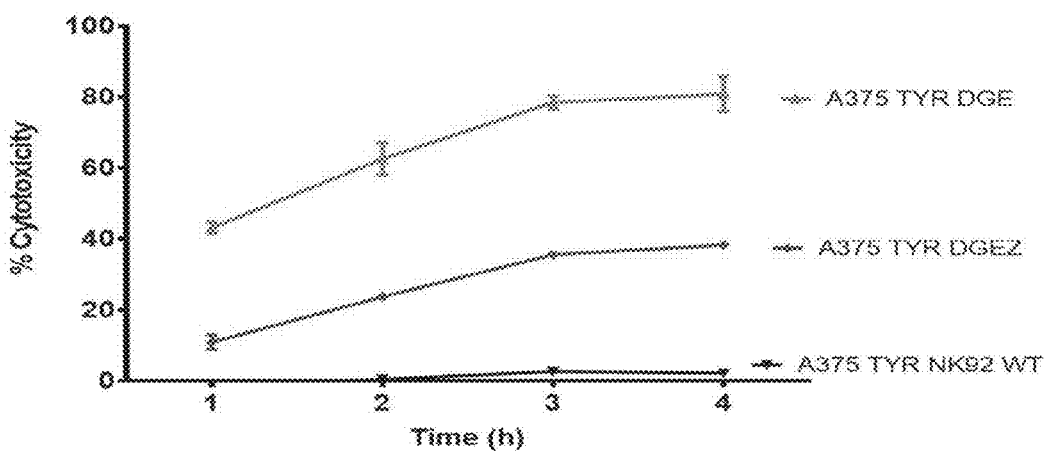
Figure 10C:
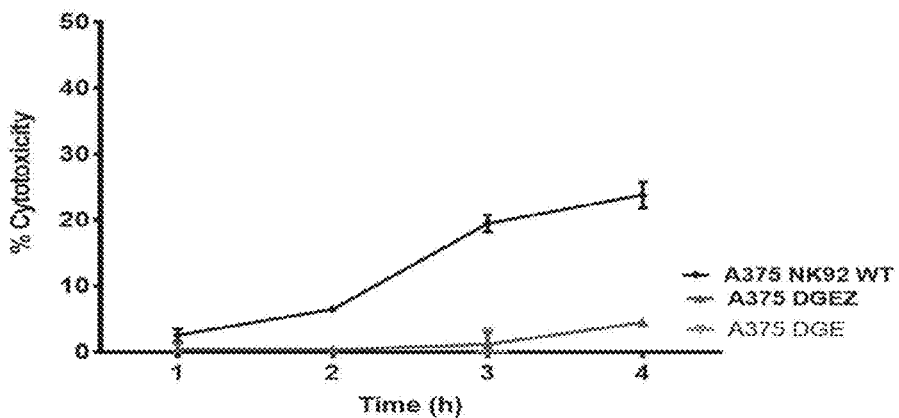
Figure 10D:
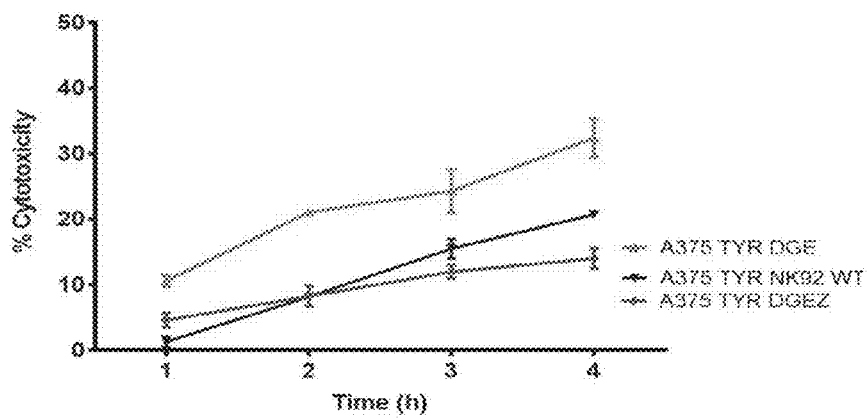
Figure 10E:
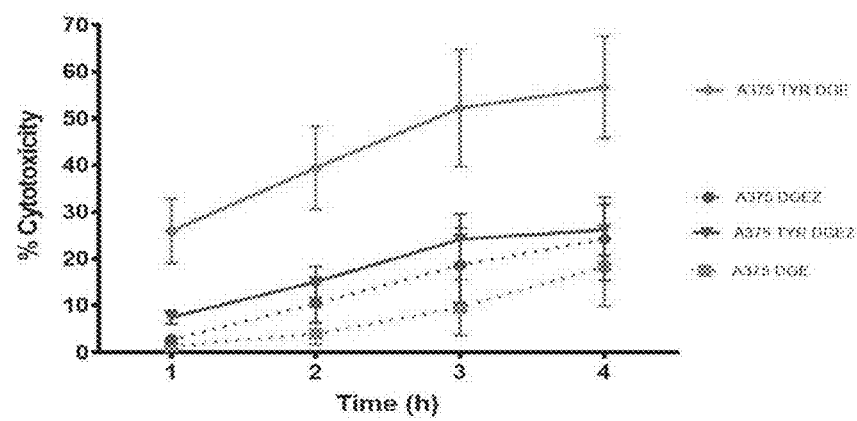
Figure 10F:
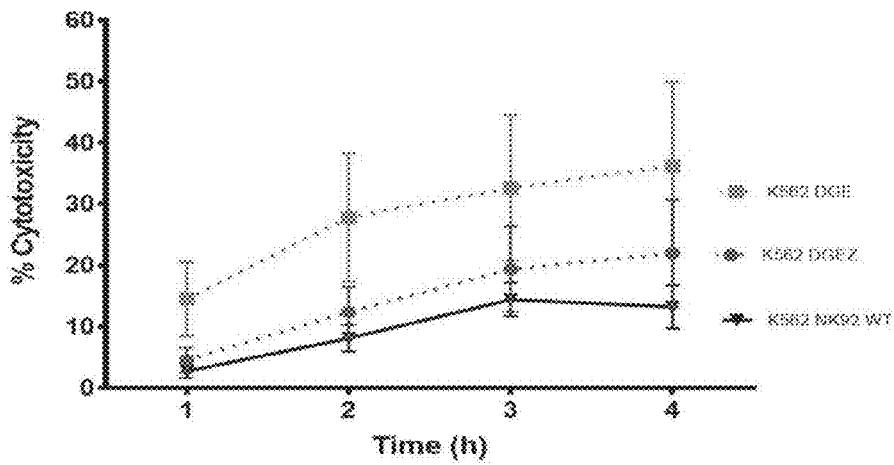
Figure 11B:
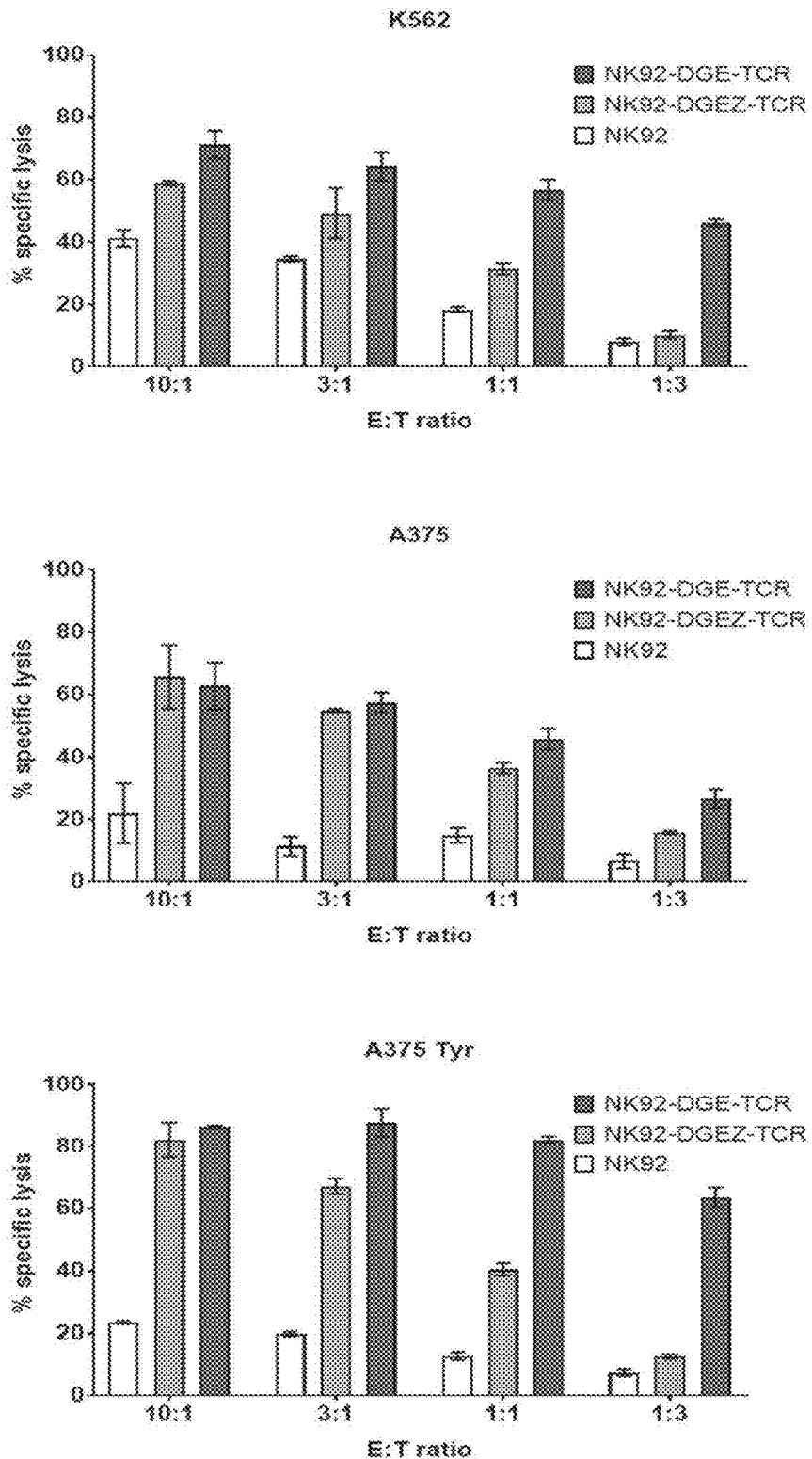
Figure 11C:
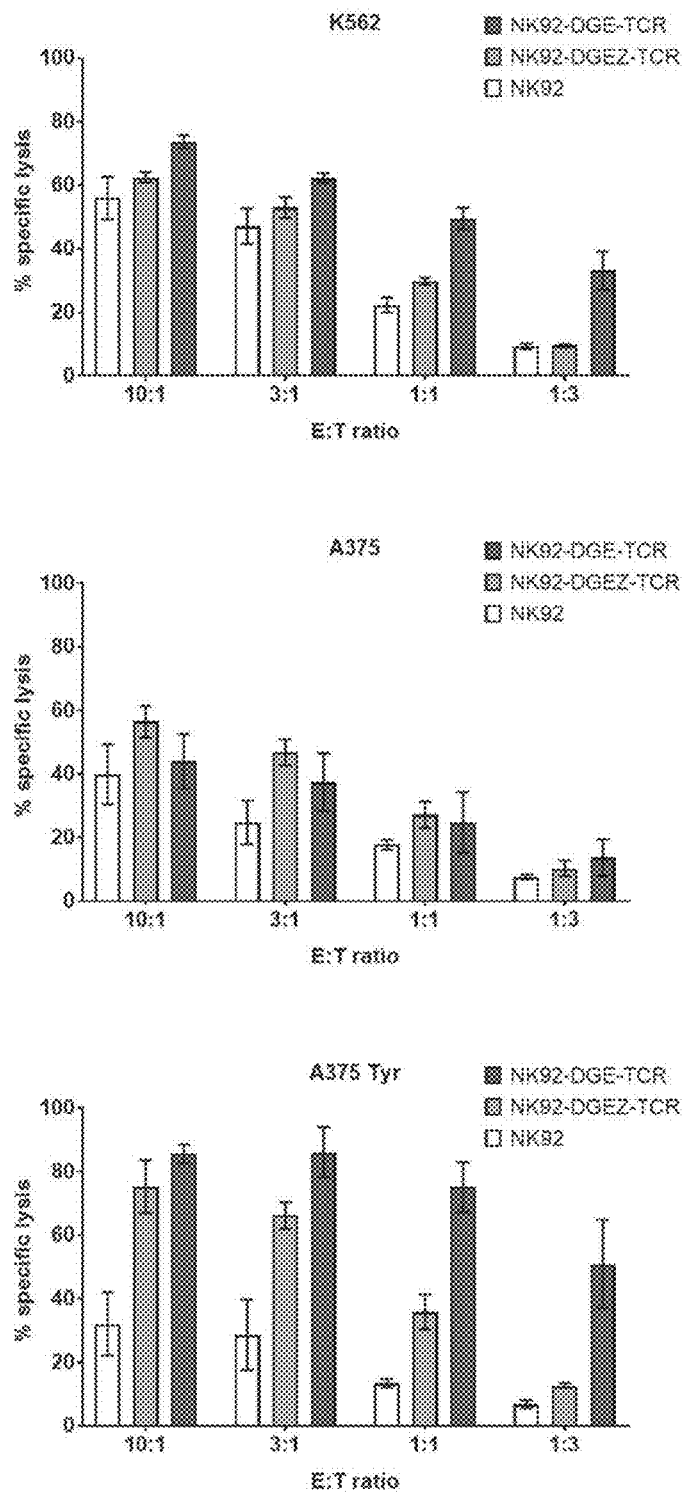

Live cell imaging experiments were run to record the antigen-specific cytotoxic activity of TCR gene modified NK-92 cells. In a two-hour imaging experiment, rapid antigen-specific killing of A375(Tyr) cells by TCR expressing NK-92 cells was observed while activity against the non tyrosinase expression A375 cells was at a minimum. Images from the beginning and the end of the two-hour experiment with different targets and effectors are presented in FIG. 6D.

Figure 13:
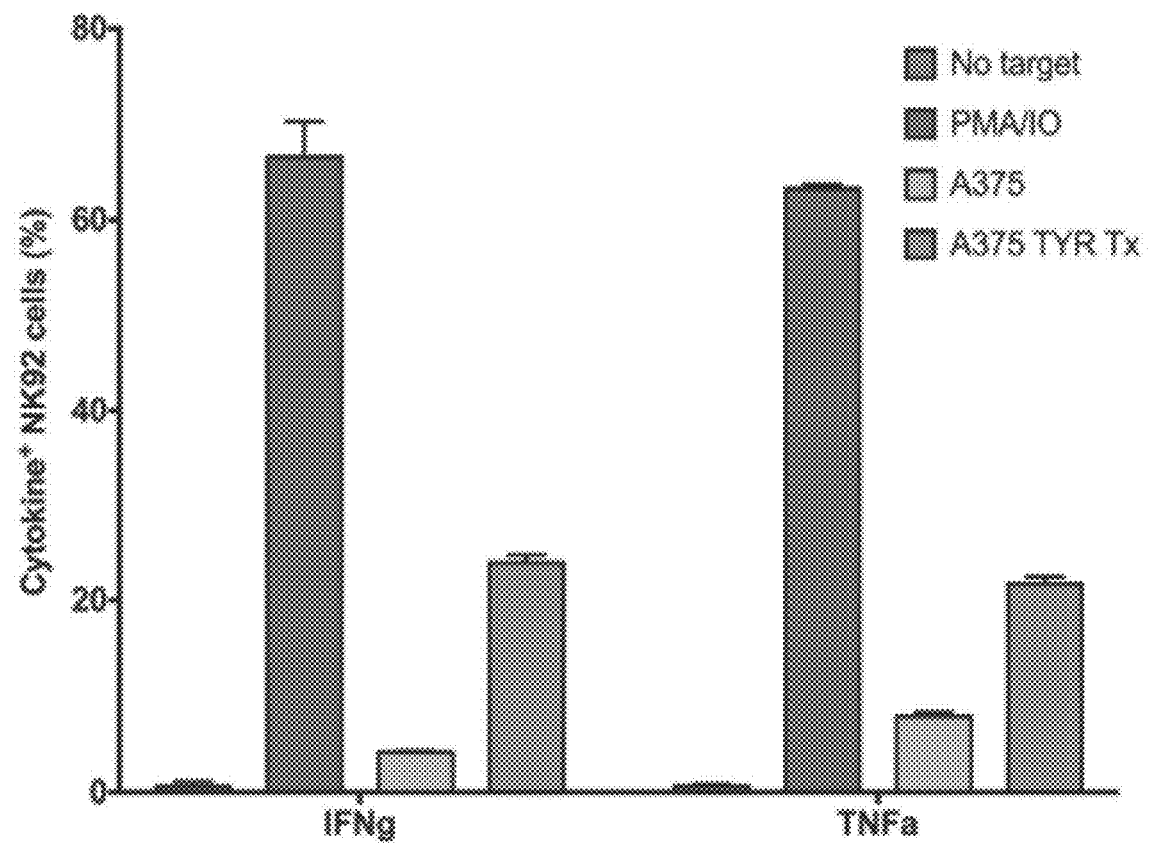
FIG. 13 is a bar graph showing cytokine secretion of DGE-TCR cells against A375, A375(Tyr), T2, and K562 cells.
Figure 14:
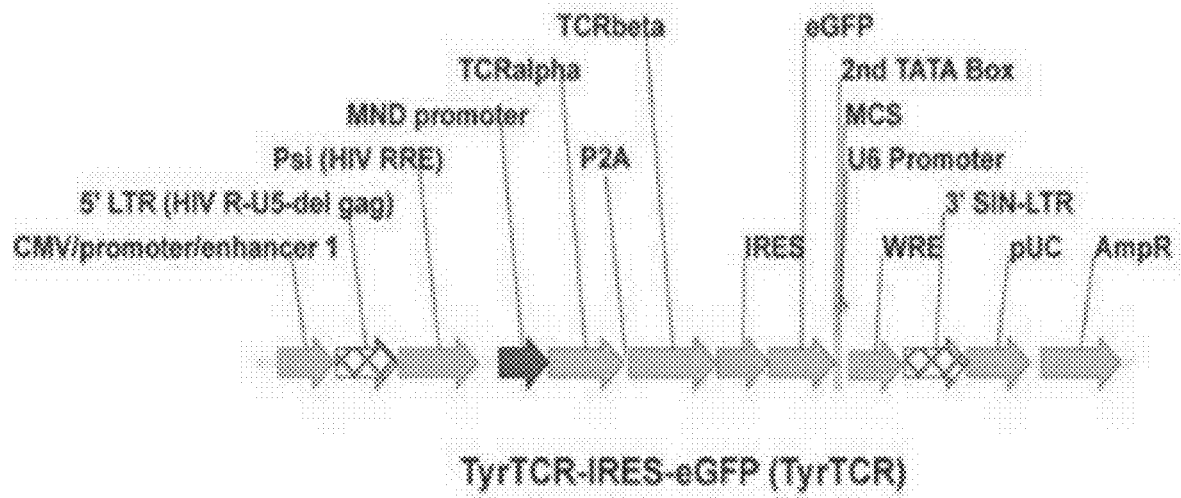
FIG. 14 is a schematic illustration of the lentiviral vector TyrTCR-IRES-eGFP (TyrTCR).

Cytokine secretion of DGE-TCR cells against A375, A375(Tyr), T2, and K562 cells is shown in the bar graph of FIG. 13. DGE/TCR cells are potent producers of INFg and TNFa upon PMA/Ionomycin treatment. Both INFg and TNFa are secreted upon TCR triggering by A375(Tyr) cells but not against A375 alone.

Expressing functional TCRs on NK cells stands out as a unique discovery combining robust and effective cytotoxic capacity of NK cells with exclusive antigen specificity of T cells as a novel approach to develop cell-based immunotherapy of cancer and potentially viral infections such as HIV. This study shows, for the first time, the functional expression of a TCR on NK cells in an attempt to circumvent risks related to TCR mispairing and supply a new source of effector cells for TCR gene therapy applications.

The two most common strategies for genetically targeting cytotoxic lymphocytes to specific antigens are the transfer of genes encoding TCR α/β heterodimers or CARs. The transfer of CAR genes into NK cells and their use in adoptive immunotherapy has been primarily tested in animal models and more recently in various clinical trials with promising results (Dahlberg C I, Sarhan D, Chrobok M, Duru A D, Alici E. Natural Killer Cell-Based Therapies Targeting Cancer: Possible Strategies to Gain and Sustain Anti-Tumor Activity. Frontiers in immunology. 2015; 6:605). Zhang et al. has recently reported the redirecting of NK-92 cytotoxicity by genetic modification with a CAR derived from a TCR-like antibody against gp100/HLA-A2 complex (Zhang G, Liu R, Zhu X, Wang L, Ma J, Han H, et al. Retargeting NK-92 for anti-melanoma activity by a TCR-like single-domain antibody. Immunology and cell biology. 2013 November-December; 91(10):615-24). While Zhang also claims to confer TCR-like specificity to NK cells, in essence the approach used is a CAR design where the antibody sequence is fused to CD3ζ intracellular domain to turn the antibody into a receptor and signaling is mediated through CD3ζ alone in a classical 1$^{st}$ generation CAR design.

The inventive approach described herein provides a proof-of-principle for functional TCR expression on NK cells by making use of a TCR α/β heterodimer that functions independently of the co-receptors CD4 and CD8. While it remains unknown whether co-receptor dependent TCRs will work in the same manner by using endogenous CD4 or CD8 expression in NK cells, it is also possible to include CD4 or CD8 in the design of the genetic modification process.

Another parameter to optimize in the case of TCR expression on NK cells is whether there will be mutual interference of this modification with the mechanisms of missing-self recognition (Ljunggren H G, Karre K. In search of the 'missing self': MHC molecules and NK cell recognition. Immunology today. 1990 July; 11(7):237-44) in NK cells. In the experimental setting described herein T2 cells have almost no surface MHC expression due to TAP deficiency and NK-92 cells have no KIR expression except for low levels of KIR2DL4 (Maki G, Klingemann H G, Martinson J A, Tam Y K. Factors regulating the cytotoxic activity of the human natural killer cell line, NK-92. Journal of hematotherapy & stem cell research. 2001 June; 10(3):369-83), it is not possible to make any statements about missing-self recognition. Regardless, a high rate of degranulation was seen when WT NK-92 cells are incubated with DMSO control T2 cells, potentially due to CD40-CD40L interaction (Maki G, Klingemann H G, Martinson J A, Tam Y K. Factors regulating the cytotoxic activity of the human natural killer cell line, NK-92. Journal of hematotherapy & stem cell research. 2001 June; 10(3):369-83 and Carbone E, Ruggiero G, Terrazzano G, Palomba C, Manzo C, Fontana S, et al. A new mechanism of NK cell cytotoxicity activation: the CD40-CD40 ligand interaction. The Journal of experimental medicine. 1997 Jun. 16; 185(12):2053-60). Despite this high background, TCR expression on NK-92 cells is still able to mount an impressive degranulation response against peptide-loaded T2 cells.

Protocols: (Methods and Materials)
Cell Lines

293FT cells were maintained in Dulbecco's Modified Eagle Medium (DMEM) (GIBCO, Life Technologies, Grand Island, N.Y., USA) supplemented with 10% Fetal Bovine Serum (FBS) (GIBCO), 0.1 mM non-essential amino acids (Sigma-Aldrich, St. Louis, Mo., USA), 6 mM L-glutamine (Sigma-Aldrich), 1 mM sodium pyruvate (Sigma-Aldrich) and 20 mM HEPES (Sigma-Aldrich). NK-92 cells were maintained in CellGro SCGM (Cellgenix) medium supplemented with 20% FBS and 1000 U/ml rhIL-2 (Proleukin, Novartis). T2 and YTS cells were maintained in RPMI-1640 medium (GIBCO) supplemented with 10% FBS.

Production of Lentiviral Vectors

For production of VSV-G pseudotyped lentiviral vectors, 14×10$^6$ 293FT cells were plated into a poly-D-lysine coated 150 mm dish (BD Biosciences, San Jose, Calif., USA). Next day cells were transfected with 30 μg of vector plasmid (LeGO vectors courtesy of Prof. Boris Fehse, University Medical Center Hamburg-Eppendorf, Hamburg, Germany), 15 μg of pMDLg/pRRE (Addgene, Cambridge, Mass., USA), 10 μg of pRSV-REV (Addgene) and 5 μg of phCMV-VSV-G (Addgene) using calcium phosphate transfection kit (Sigma-Aldrich) in the presence of 25 μM Chloroquine (Sigma-Aldrich). 10 hours after transfection, the medium was changed and thereafter virus containing supernatant was collected every 24 hours for 2 days and stored in −80° C. until further use. A small aliquot from each production was used to determine viral titers by transduction of 293FT cells with serially diluted amounts of virus supernatant.

Lentiviral Transduction of NK Cells

For each lentiviral transduction, $0.25 \times 10^6$ NK-92 or YTS cells per well were seeded in a 24-well plate (BD Biosciences) and mixed with an appropriate amount of virus supernatant in the presence of 8 µg/ml of protamine sulfate and 3 µM BX795 (Sigma-Aldrich) in a final volume of no more than 1 ml. The plates were incubated at 37° C., 5% $CO_2$ for 6 hours. At the end of the incubation, cells were spinned down at 300×g for 10 minutes at room temperature after which the supernatants were removed from the wells and 1 ml of fresh growth medium per well was added. The cells were maintained in this medium for at least 3 days before acquisition of gene expression was carried out.

Flow Cytometry

All antibody stainings for flow cytometry were done according to the following protocol: For surface stainings, the cells were washed once with PBS and incubated with appropriate amounts of antibody at 4° C. for 30 min. The labeled cells were then washed with PBS and data acquisition was done. The antibodies used for NK cells were CD56 (NCAM16.2) and CD3e (UCHT1) from BD Biosciences. For intracellular staining, cells were fixed and permeabilized for 15 minutes in a solution containing 2% PFA in 1× Permeabilization Wash Buffer (BioLegend), washed two times with Permeabilization Wash Buffer and incubated with appropriate amounts of antibody at 4° C. for 30 min. The labeled cells were then washed with Permeabilization Wash Buffer and data acquisition was carried out. For data acquisition, FACSCanto (BD Biosciences), LSR Fortessa (BD Biosciences) or NovoCyte 3000 (ACEA Biosciences) instruments were used depending on availability. Data were analysed with the FlowJo software (TreeStar Inc.).

Western Blot Analysis

Cells were lysed in lysis buffer (1% Triton X-100, 0.15M NaCl, 0.002M EDTA (pH 8.0) and 0.05 M Trizma [pH 7.4]) and protease inhibitors (11836153001, Sigma Aldrich). Protein content was measured by Bradford assay (B6916, Sigma Aldrich), and analyzed under reducing conditions with 12% SDS-PAGE, followed by electroblotting on PVDF transfer membranes (88518, Thermo Scientific). The membranes were blocked with 5% skim milk (70166, Sigma Aldrich). Membranes were incubated overnight at 4° C. with the indicated primary antibodies. The dilutions of antibodies were prepared as follows: mouse anti-CD 247 (51-6527GR; BD Pharmingen, 1:500), rabbit pAb CD3δ (ab103573, Abcam, 1:300), goat pAb CD3γ (ab200563, Abcam, 1:300), rabit anti β-actin pAb HRP conjugate (5125S, Cell Signaling Technology, 1:2000). After washing, membranes were treated with horseradish peroxidase-conjugated secondary antibodies, donkey Anti-goat IgG-HRP(sc-2033, Santa Cruz Biotechnology, 1:2500) incubated overnight at 4° C., rabbit Anti-Mouse IgG-HRP(A9044, Sigma Aldrich, 1:80000) and goat Anti-Rabbit IgG-HRP (7074P2, Cell Signaling Technology, 1:20000) incubated 1 hour at room temperature. Then the bands were visualized using ECL (0.45 mM Luminol, 0.625 mM Comaric Acid, 0.07M Trizma [pH 8.8]) in Luminescent Image Analyzer (Image Qant LAS 4000 mini, GE Healthcare Life Sciences). Images were quantified using ImageJ.

Peptides and HLA A2 Pentamers

Tyrosinase$_{(368-379)}$ (SEQ ID NO:1) and Melan-A/Mart-1$_{(27-35)}$ (SEQ ID NO:2) peptides as well as APC conjugated Tyrosinase$_{(368-379)}$/HLA-A2 pentamers were purchased from ProImmune Ltd (Oxford, UK). $0.5 \times 10^6$ NK-92 cells were washed once with PBS and incubated with 10 ul of Tyrosinase$_{(368-379)}$/HLA-A2 pentamers at 4° C. for 30 min. The labeled cells were then washed PBS twice and data acquisition was carried out. Data were analysed with the FlowJo software (TreeStar Inc.).

Analysis of NK Cell Degranulation

TAP-deficient T2 cells were pulsed with different concentrations of indicated peptides in serum free RPMI medium at 26° C. overnight in 5% $CO_2$. Cells were subsequently washed and incubated in RPMI medium at 37° C. for 60 min. Then, NK-92 or YTS cells were co-incubated with T2 or A375 target cells at a ratio of 1:1 in a final volume of 200 µl in round-bottomed 96-well plates at 37° C. and 5% $CO_2$ for 6 h. Fluorochrome-conjugated anti-CD107a mAb was added at the initiation of the assay. After 1 h of coincubation, Monensin (BioLegend) was added at a 1:100 dilution. The cells were then washed, resuspended in ice-cold PBS and immediately analyzed by flow cytometry.

Analysis of NK cCell Cytotoxicity by Xcelligence RTCA

Real time cell viability experiments were performed by using xCELLigence RTCA DP device (ACEA Biosciences Inc., San Diego, Calif., USA) placed in a humidified incubator at 37° C. and 5% $CO_2$. The E-16 plates were incubated with 100 µl of cell-free growth medium (10% FBS) at room temperature for 15 min. After incubation background impedance signal was measured to control all the connections. The target cells were seeded into E-16 plate as indicated concentrations which are $1 \times 10^4$ in 100 µl for A375 Tyr cells and $1.5 \times 10^4$ in 100 µl for A375 cells. The plates are mounted to device and incubated for 30 min before starting the experiment. The target cells were allowed to grow for about 16 h before adding effector cells. The following day, the effector cells were added onto the target cells at an E:T ratio of 1:1. Real time measurements were performed by recording the Cell index (CI) every 15 min, for 40 h. Data analysis was carried out with the RTCA software (version 1.2, Roche Diagnostics).

Analysis of NK Cell Cytotoxicity by $^{51}$Cr Release Assay

NK-cell cytotoxicity was measured in a $^{51}$Cr-release assay against K562, T2 and A375 cells. Briefly, cells were labeled with 100 uCi $^{51}$Cr (PerkinElmer, Waltham, Mass.) for 1 hour at 37° C., NK cells were mixed with the labeled cells at different effector:target ratios and incubated for 4 hours. Supernatants (70 µl) were transferred into 4 ml sample tubes and counted using a Packard Cobra Auto-Gamma 5000 Series Counting System (GMI, Ramsey, MN)[11].

Live Cell Imaging

For live cell imaging $0.25 \times 10^6$ A375 or A375(Tyr) cells were seeded in 6-well plates with glass coverslips (0.17 mm thickness, 25 mm diameter) at the bottom and left to grow overnight. The next day, coverslips were removed from the plates, rinsed once with PBS and mounted into an Attofluor Cell Chamber (Invitrogen) and 900 µl fresh growth medium was added into the chamber. Thereafter, the chamber was put in the microscope and $0.1 \times 10^6$ effector cells in resuspended in 100 µl medium were added. After letting the effector cells settle at the bottom of the chamber for 5 minutes, images were recorded with 15 sec intervals for a total of 2 hours. For incubation and analysis, a ZEISS Observer Z1 fluorescent microscope equipped with a XLmulti 51 Incubator unit was used. Image analysis and video exporting was done using the ZenPRO software.

Statistical Analysis

For preparation of graphs and statistical analysis, GraphPad Prism (GraphPad Software Inc. La Jolla, Calif., USA) was used.

Study 3:
Engineering Antigen-Specific Natural Killer Cells Against the Melanoma-Associated Antigen Tyrosinase via TCR Gene Transfer T cell receptors (TCRs) and chimeric antigen receptors (CARs) are both used for antigen-specific targeting of cytotoxic lymphocytes for tumor cell elimination, but an essential difference remains between them. CARs can target any cell surface antigen and are used efficiently to direct T and natural killer (NK) cell mediated cytotoxicity (Fournier, C. et al. Trial Watch: Adoptively transferred cells for anticancer immunotherapy. *Oncoimmunology* 6, e1363139 (2017)), while they remain blind to intracellular antigens. TCR gene transfer holds the key to recognizing intracellular antigens via epitopes presented on MEW but this has been restricted to T cells (Morgan, R. A. et al. Cancer regression in patients after transfer of genetically engineered lymphocytes. *Science* 314, 126-129 (2006); Cooper, L. J., Kalos, M., Lewinsohn, D. A., Riddell, S. R. & Greenberg, P. D. Transfer of specificity for human immunodeficiency virus type 1 into primary human T lymphocytes by introduction of T-cell receptor genes. *Journal of virology* 74, 8207-8212 (2000); and Rubinstein, M. P. et al. Transfer of TCR genes into mature T cells is accompanied by the maintenance of parental T cell avidity. *Journal of immunology* 170, 1209-1217 (2003)), leaving intracellular antigens as off-range targets for NK cells. Moreover, due to the heterodimeric structure of the TCR molecule, α and β chains introduced into T cells during TCR gene therapy have a risk of mispairing with the endogenously expressed complementary β or α chains (Govers, C., Sebestyen, Z., Coccoris, M., Willemsen, R. A. & Debets, R. T cell receptor gene therapy: strategies for optimizing transgenic TCR pairing. *Trends in molecular medicine* 16, 77-87 (2010)), giving rise to TCRs of unpredictable specificity that may cause iatrogenic autoimmunity (Ferrara, J., Reddy, P. & Paczesny, S. Immunotherapy through T-cell receptor gene transfer induces severe graft-versus-host disease. *Immunotherapy* 2, 791-794 (2010)).

The instant invention describes the use of NK cells for TCR gene therapy in order to overcome this mispairing obstacle and open the realm of intracellular antigens to targeting by NK cells.

The use of TCR or CAR genes for redirecting T cell-mediated immunity against tumor-associated antigens (TAAs) are among the approaches that have found their way into clinical trials (Spear, T. T., Nagato, K. & Nishimura, M. I. Strategies to genetically engineer T cells for cancer immunotherapy. *Cancer Immunol Immunother* 65, 631-649 (2016)) and more recently transformed into approved clinical practice in the case of CAR-T cells (Jain, M. D. & Davila, M. L. Concise Review: Emerging Principles from the Clinical Application of Chimeric Antigen Receptor T Cell Therapies for B Cell Malignancies. *Stem Cells* 36, 36-44 (2018)).

Mispairing of α/β chains after TCR gene delivery stands out as a major bottleneck if safe and successful TCR gene therapy is to be achieved. To minimize the risks associated with mispairing, a battery of different solutions has been suggested, including modifications of the TCR sequence to circumvent mispairing (Govers, C. et al. TCRs genetically linked to CD28 and CD3epsilon do not mispair with endogenous TCR chains and mediate enhanced T cell persistence and anti-melanoma activity. *Journal of immunology* 193, 5315-5326 (2014); Knies, D. et al. An optimized single chain TCR scaffold relying on the assembly with the native CD3-complex prevents residual mispairing with endogenous TCRs in human T-cells. *Oncotarget* (2016); and Tao, C. et al. Imaging of T-cell receptor fused to CD3zeta reveals enhanced expression and improved pairing in living cells. *International journal of molecular medicine* 34, 849-855 (2014) or the detection (Shao, H. et al. TCR mispairing in genetically modified T cells was detected by fluorescence resonance energy transfer. *Molecular biology reports* 37, 3951-3956 (2010)) and elimination (Kieback, E., Charo, J., Sommermeyer, D., Blankenstein, T. & Uckert, W. A safeguard eliminates T cell receptor gene-modified autoreactive T cells after adoptive transfer. *Proceedings of the National Academy of Sciences of the United States of America* 105, 623-628 (2008)) of T cells carrying mispaired TCRs as well as knocking out endogenous TCR genes (Okamoto, S. et al. Improved expression and reactivity of transduced tumor-specific TCRs in human lymphocytes by specific silencing of endogenous TCR. *Cancer Res* 69, 9003-9011 (2009) and Provasi, E. et al. Editing T cell specificity towards leukemia by zinc finger nucleases and lentiviral gene transfer. *Nat Med* 18, 807-815 (2012)). These procedures still carry a considerable risk of creating mispaired TCRs of unknown specificity, while problems such as immunogenicity related to the modification of the TCR sequence (Davis, J. L. et al. Development of human anti-murine T-cell receptor antibodies in both responding and nonresponding patients enrolled in TCR gene therapy trials. *Clin Cancer Res* 16, 5852-5861 (2010)) or the inefficiency of the designed process impedes clinical advancement.

NK cells are promising candidates in cancer immunotherapy due to their capacity to kill tumor cells without the requirement of prior antigen exposure. The use of genetically modified (GM) NK cells redirected towards tumors via activating receptors (Pegram, H. J., Kershaw, M. H. & Darcy, P. K. Genetic modification of natural killer cells for adoptive cellular immunotherapy. *Immunotherapy* 1, 623-630 (2009) or chimeric antigen receptors (CARs) presents a promising prospect in clinical studies (Uherek, C. et al. Retargeting of natural killer-cell cytolytic activity to ErbB2-expressing cancer cells results in efficient and selective tumor cell destruction. *Blood* 100, 1265-1273 (2002)). CARs have been successfully delivered to NK cells and were shown to increase antigen-specific cytotoxic activity both in vitro and in vivo (Kruschinski, A. et al. Engineering antigen-specific primary human NK cells against HER-2 positive carcinomas. *Proceedings of the National Academy of Sciences of the United States of America* 105, 17481-17486 (2008) and Zhang, G. et al. Retargeting NK-92 for anti-melanoma activity by a TCR-like single-domain antibody. *Immunology and cell biology* 91, 615-624 (2013)). These improvements have rapidly been translated to experimental models (Lanier, L. L., Chang, C., Spits, H. & Phillips, J. H. Expression of cytoplasmic CD3 epsilon proteins in activated human adult natural killer (NK) cells and CD3 gamma, delta, epsilon complexes in fetal NK cells. Implications for the relationship of NK and T lymphocytes. *Journal of immunology* 149, 1876-1880 (1992)) and clinical trials, indicating that the adoptive transfer of GM NK cells could be an efficient approach in cancer immunotherapy (Dahlberg, C. I., Sarhan, D., Chrobok, M., Duru, A. D. & Alici, E. Natural Killer Cell-Based Therapies Targeting Cancer: Possible Strategies to Gain and Sustain Anti-Tumor Activity. *Frontiers in immunology* 6, 605 (2015)). While the two most common strategies for genetically targeting cytotoxic lymphocytes to specific antigens are the transfer of TCR or CAR genes (Stauss, H. J., Morris, E. C. & Abken, H. Cancer gene therapy with T cell receptors and chimeric antigen receptors. *Current opinion in pharmacology* 24, 113-118 (2015)), to the knowledge of the instant inventors, TCR-mediated targeting of NK cells has not yet been reported.

As discussed previously, the TCR complex is composed of six different chains: CD3 molecules (CD3δ, CD3γ, CD3ε, CD3ζ) assembled with the TCRα/β heterodimer. While NK cells lack the expression of TCR complex subunits except for CD3ζ, they express all necessary molecules for signaling (Table 1), indicating that these cells could signal if reprogrammed with a surface TCR complex. Therefore, to assemble a TCR complex on the NK cell surface, TCR α/β-expressing vectors were delivered into the NK cell lines, NK-92 and YTS, along with CD3δ, CD3γ and CD3ε in the presence or absence of CD3ζ. For the expression of TCRα/β chains, a lentiviral TyrTCR-IRES-eGFP vector (Brusko, T. M. et al. Human antigen-specific regulatory T cells generated by T cell receptor gene transfer. *PLoS One* 5, e11726 (2010)) was used that codes for a co-receptor-independent TCR against the peptide "YMDGTMSQV" SEQ ID NO: 1 from the melanoma antigen tyrosinase ($Tyr_{368-379}$) in complex with HLA-A*0201 (FIG. 4A). TCR/CD3 gene delivery into NK cells was performed using a 2-step genetic modification process as outlined (FIG. 30). Initially, CD3ε expression was assessed in GM NK-92 cells by flow cytometry. While intracellular staining showed high levels of CD3ε in cells receiving the DGE or DGEZ vectors alone, no CD3ε was detectable at the cell surface. Surface CD3ε expression was only detectable when the CD3 subunits were expressed together with TCR α/β chains (FIG. 4B). Thus, just like T lymphocytes, surface TCR expression in NK cells is the result of an assembly pathway that requires all subunits of the TCR complex (Kearse, K. P., Takahama, Y., Punt, J. A., Sharrow, S. O. & Singer, A. Early molecular events induced by T cell receptor (TCR) signaling in immature CD4+ CD8+ thymocytes: increased synthesis of TCR-alpha protein is an early response to TCR signaling that compensates for TCR-alpha instability, improves TCR assembly, and parallels other indicators of positive selection. *The Journal of experimental medicine* 181, 193-202 (1995) and Bettini, M. L. et al. Membrane association of the CD3epsilon signaling domain is required for optimal T cell development and function. *Journal of immunology* 193, 258-267 (2014)).

Figure 31:
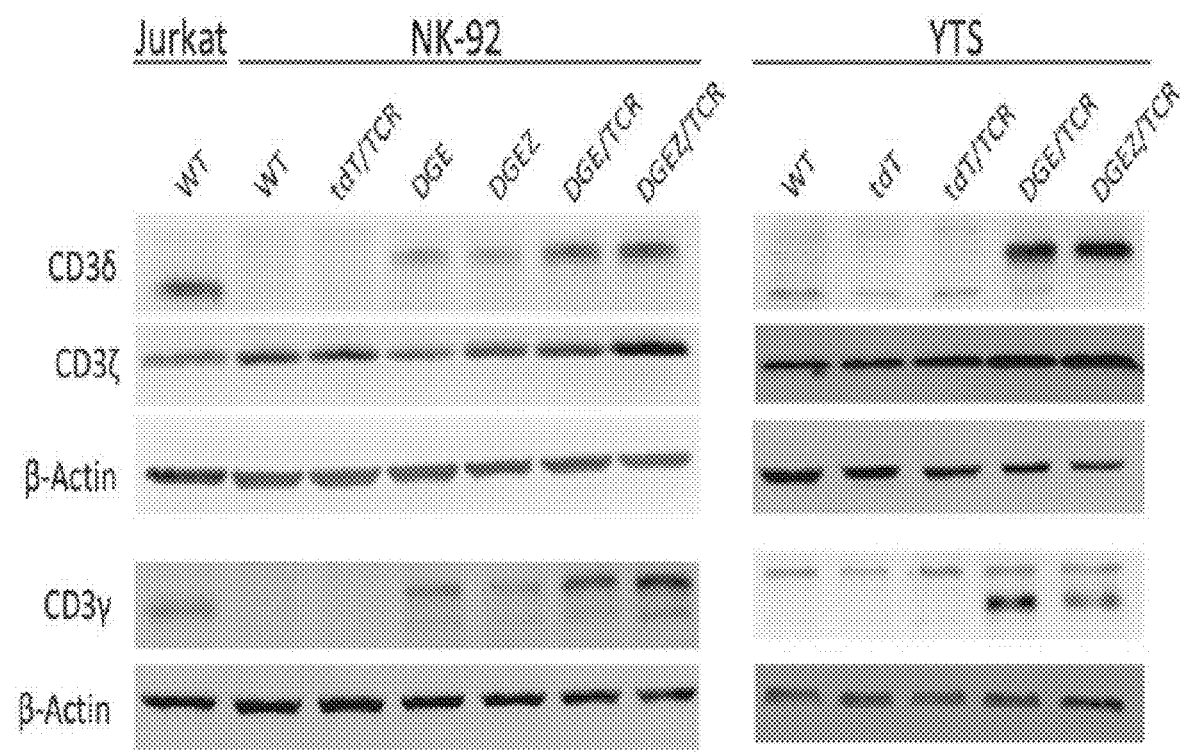
FIG. 31 shows a Western blot analysis for CD3δ, CD3γ, and CD3ζ in genetically-modified (GM) NK-92 and YTS cells.
Figure 15:
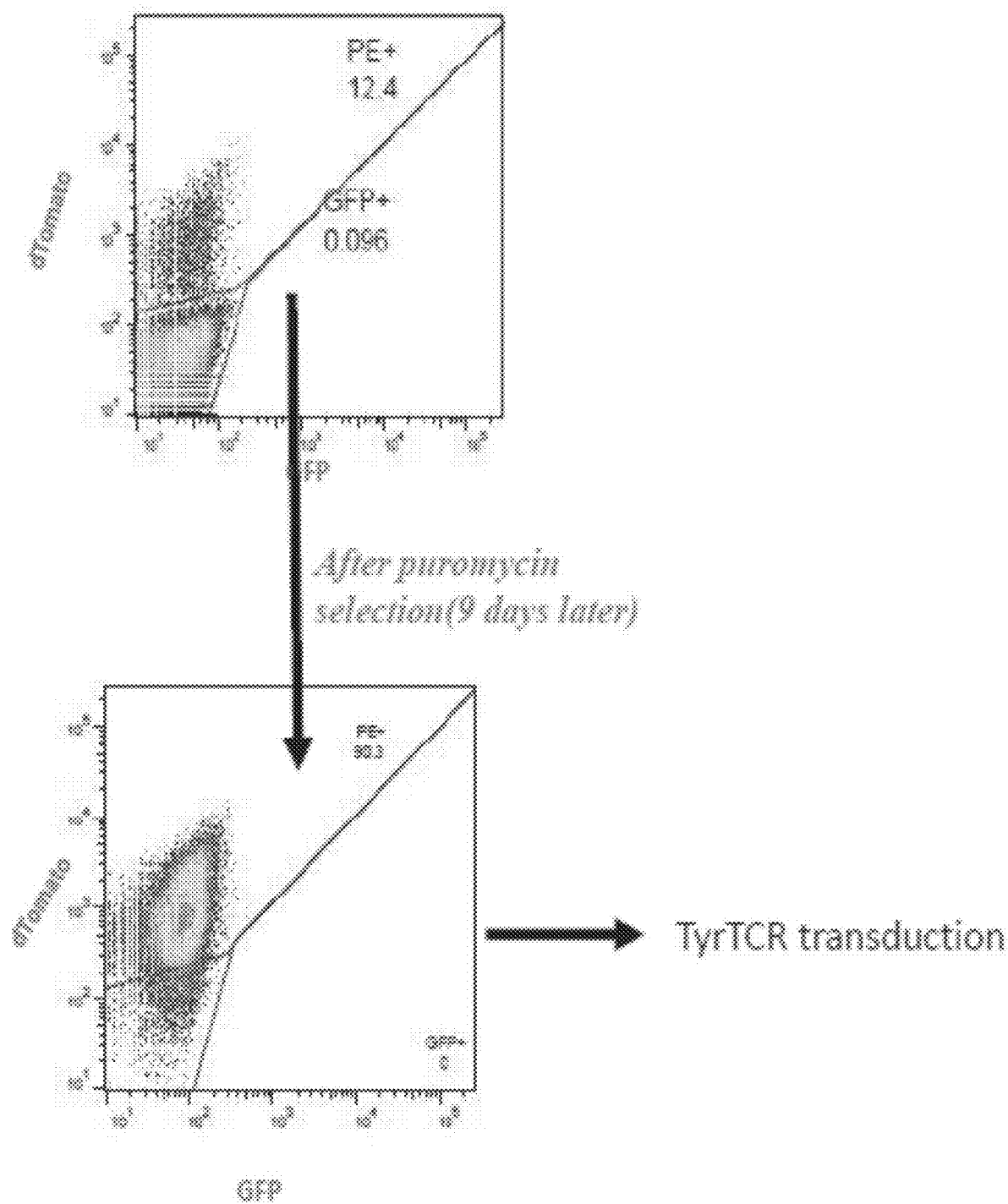
FIG. 15 shows TyrTCR transduction.
Figure 16:
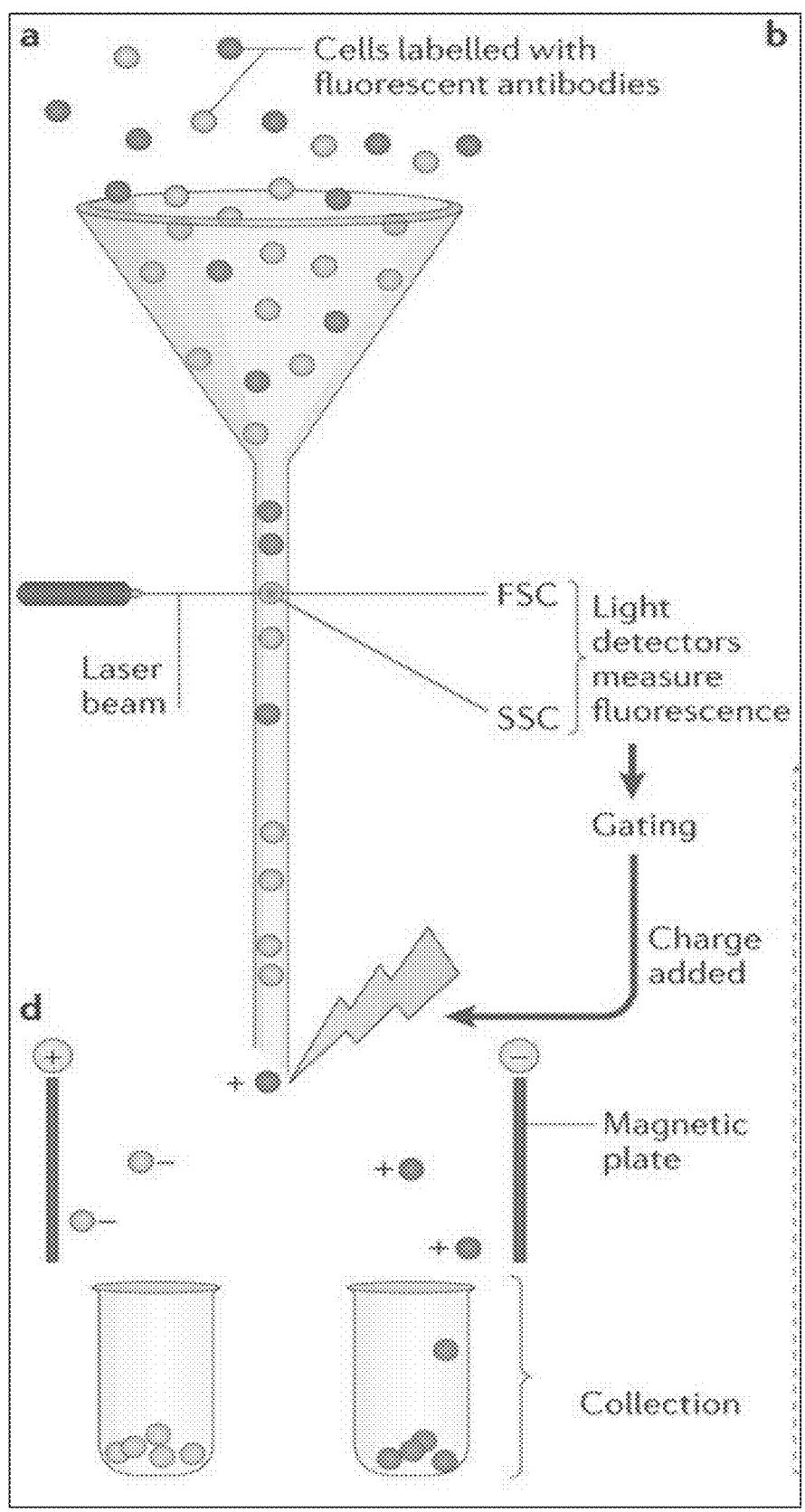
FIG. 16 illustrates isolation of the cell population via flow cytometry.
Figure 17:
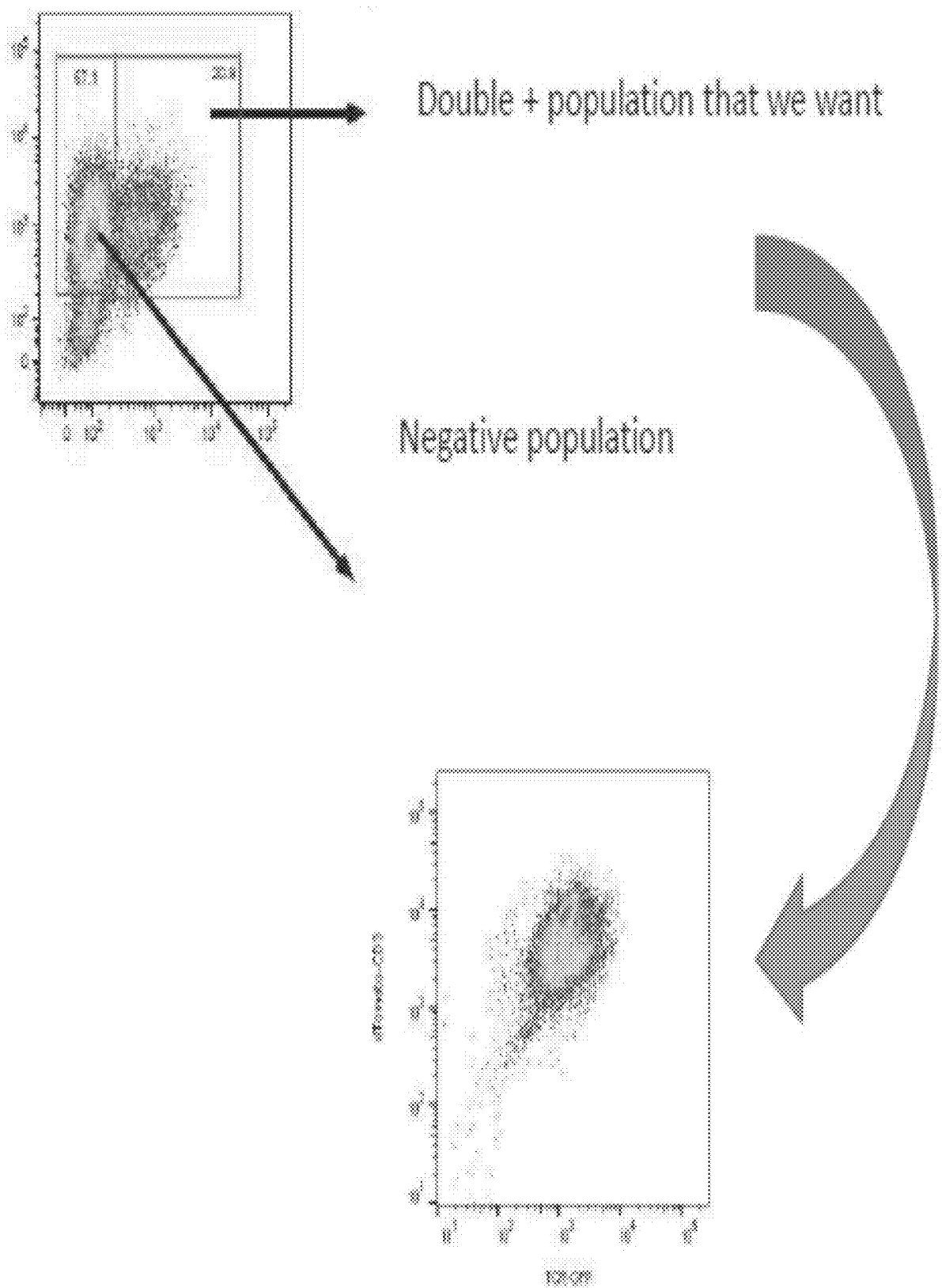
FIG. 17 shows data from isolation of the cell population via flow cytometry.
Figure 18A:
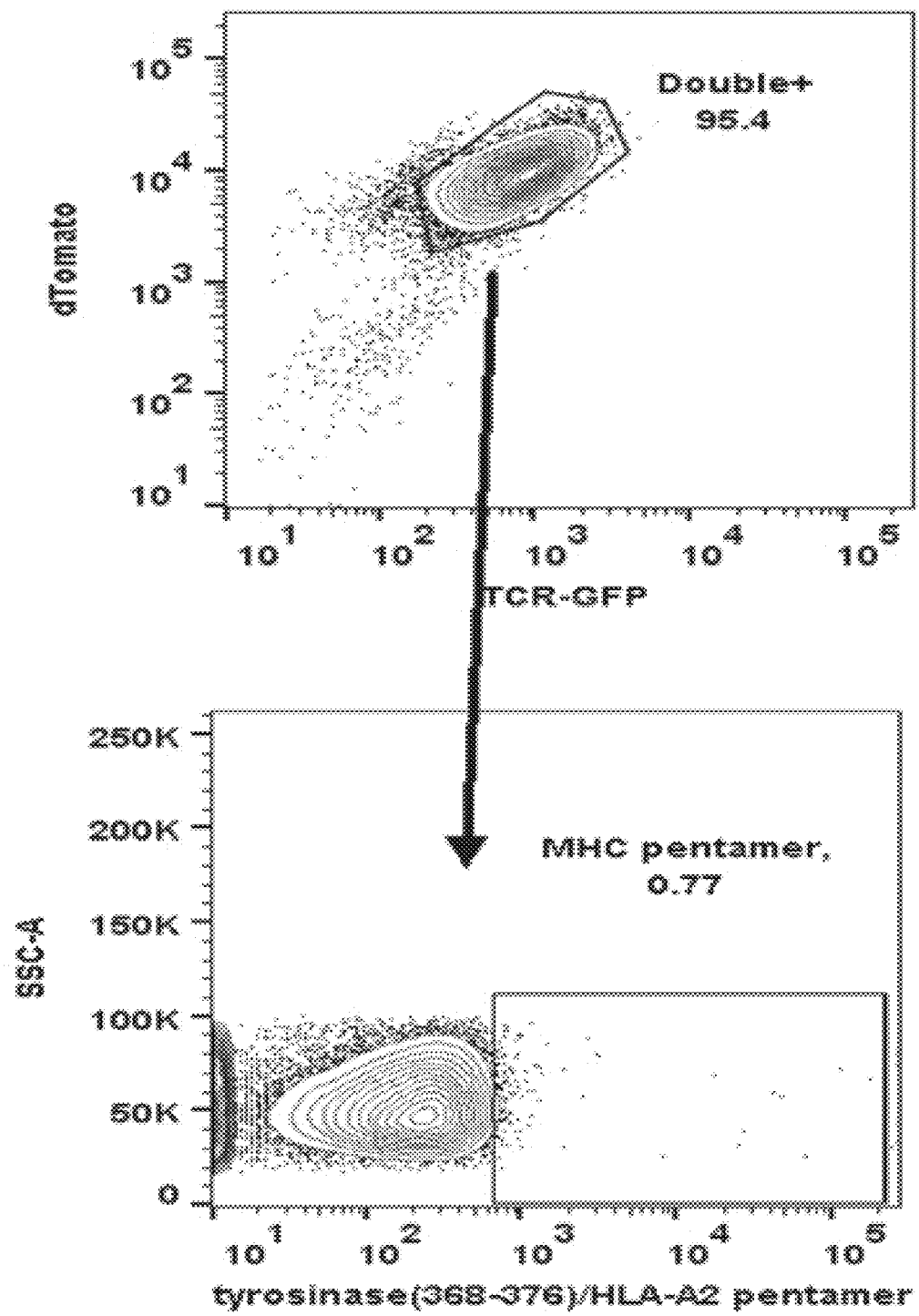
FIGS. 18A-C show tyrosinase (368-376) HLA-A2 pentameter staining on NK92 batch 1.
Figure 18B:
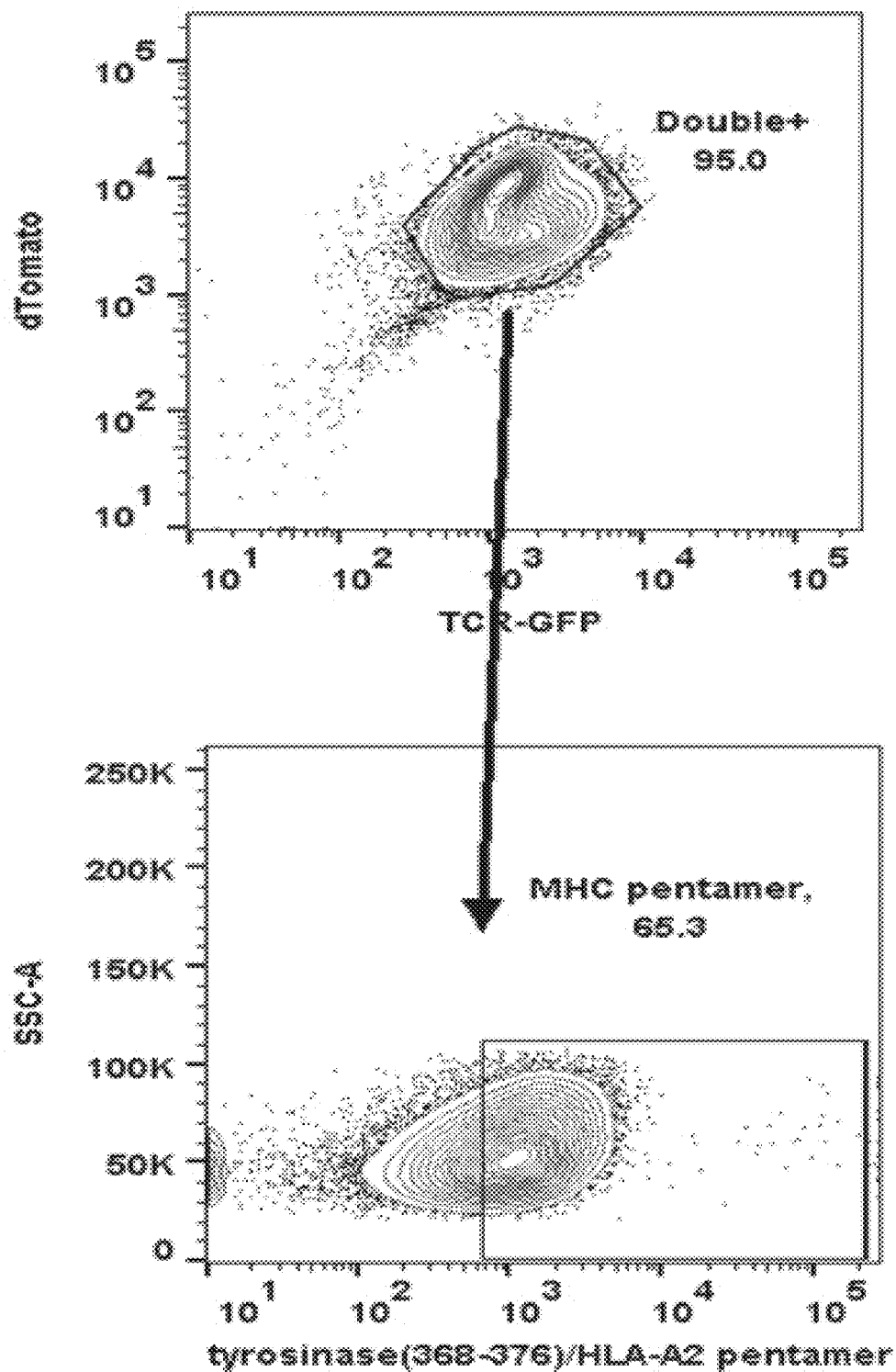
Figure 18C:
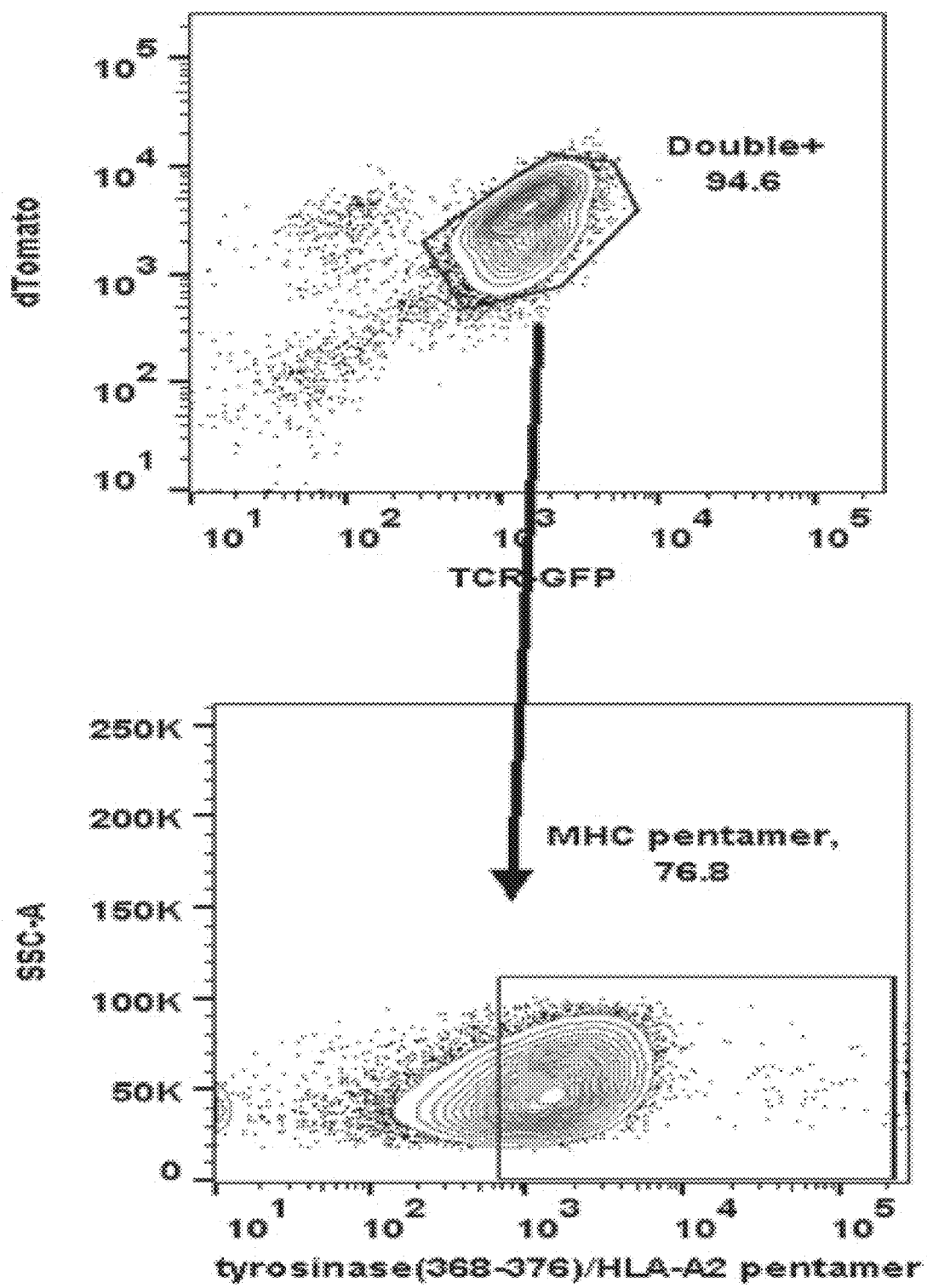
Figure 19A:
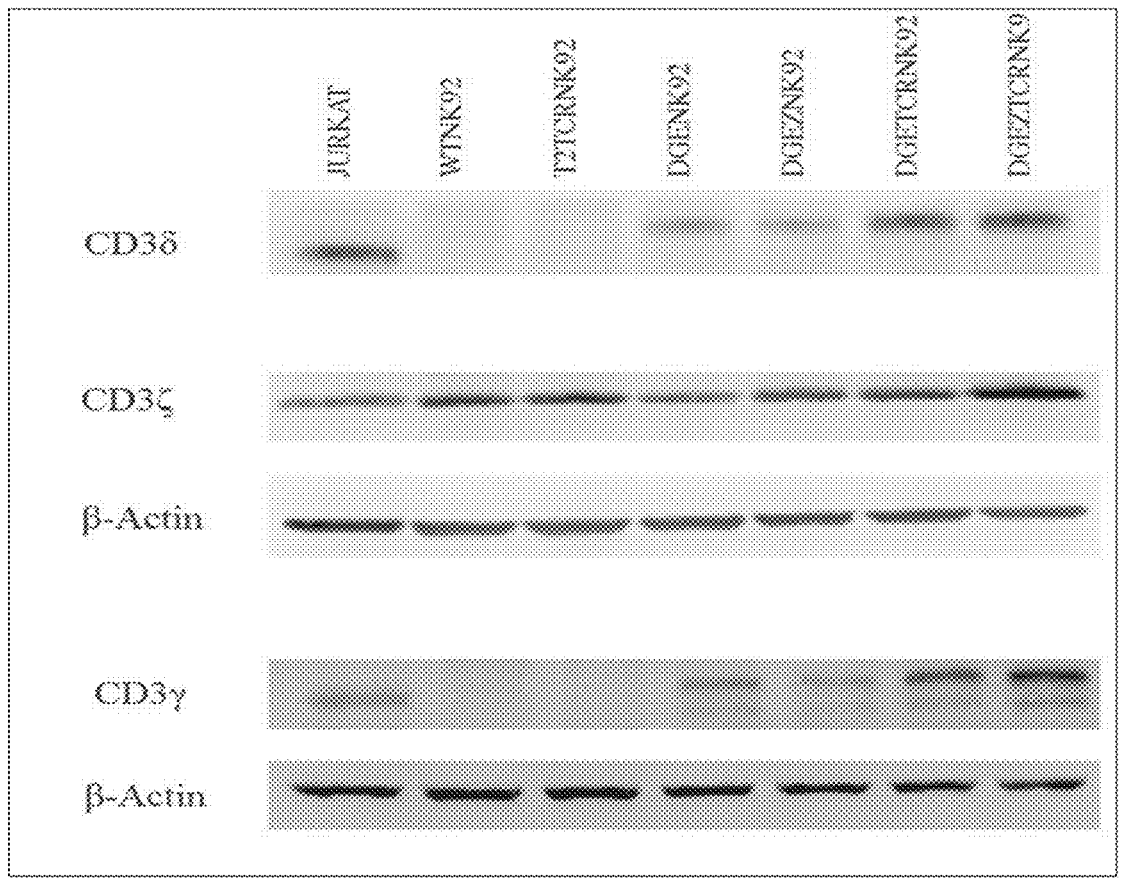
Figure 19B:
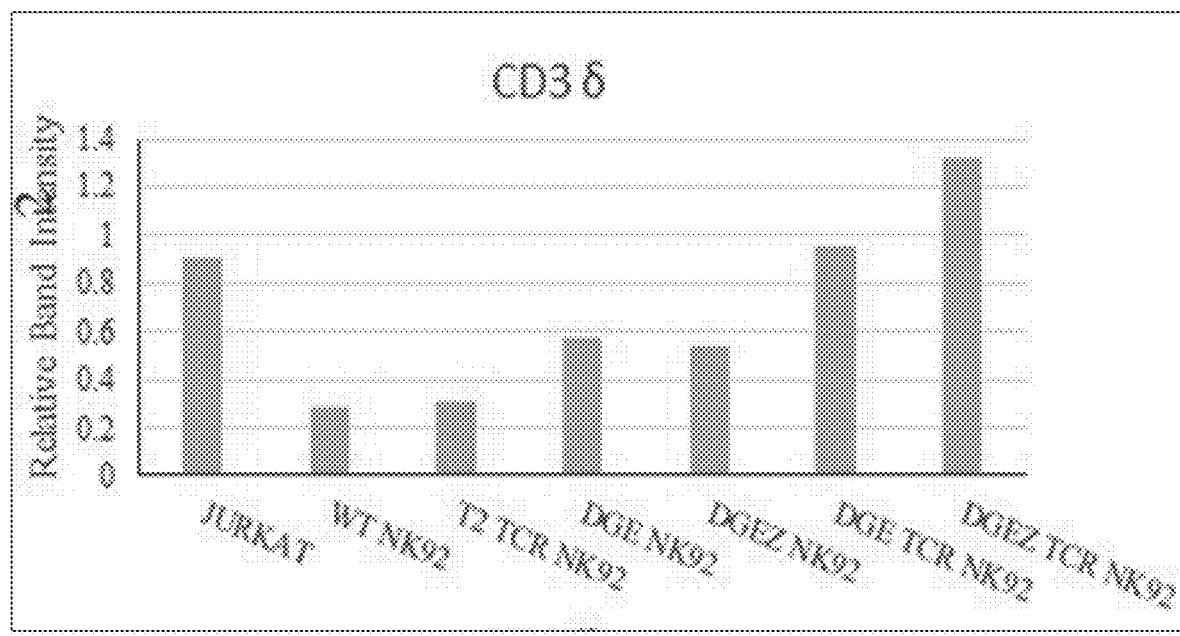
Figure 20:
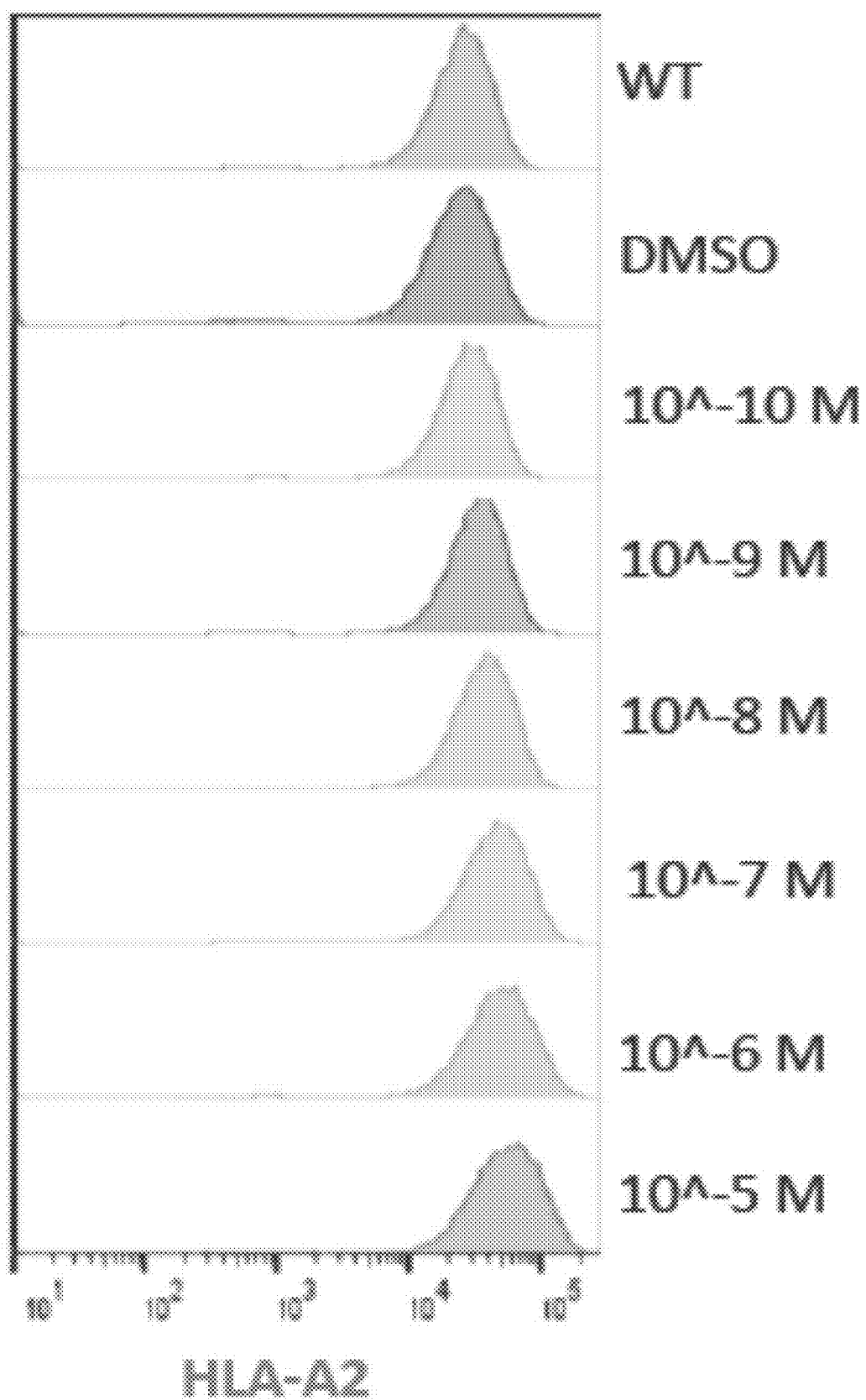
FIG. 20 shows results from a T2 peptide binding assay.
Figure 21:
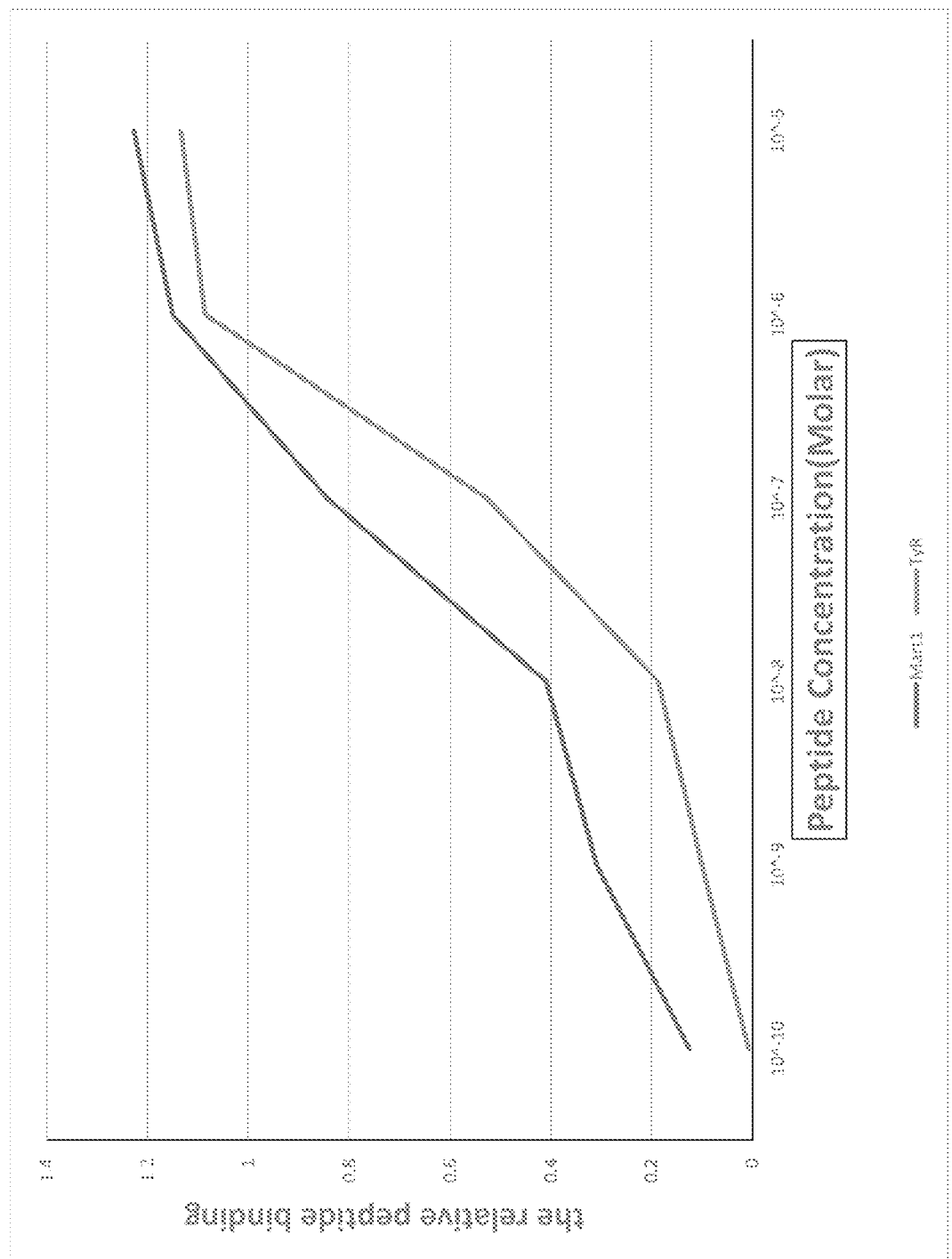
FIG. 21 is a graph showing results from a T2 peptide binding assay. Tyrosine SEQ ID NO:1 YMDGTMSQV, specificity and Mart-1 SEQ ID NO:2 ELAGIGILTV, no specificity.
Figure 23B:
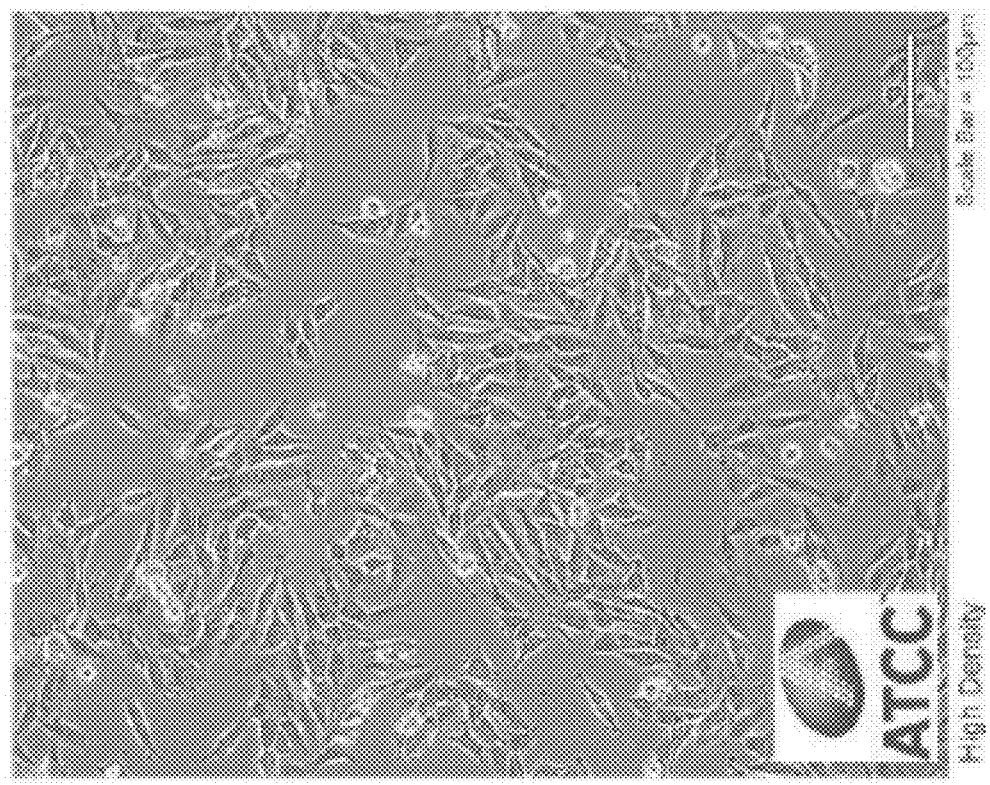
FIGS. 23A-B are photographs of cultured malignant melanoma cell line A375.
Figure 23A:
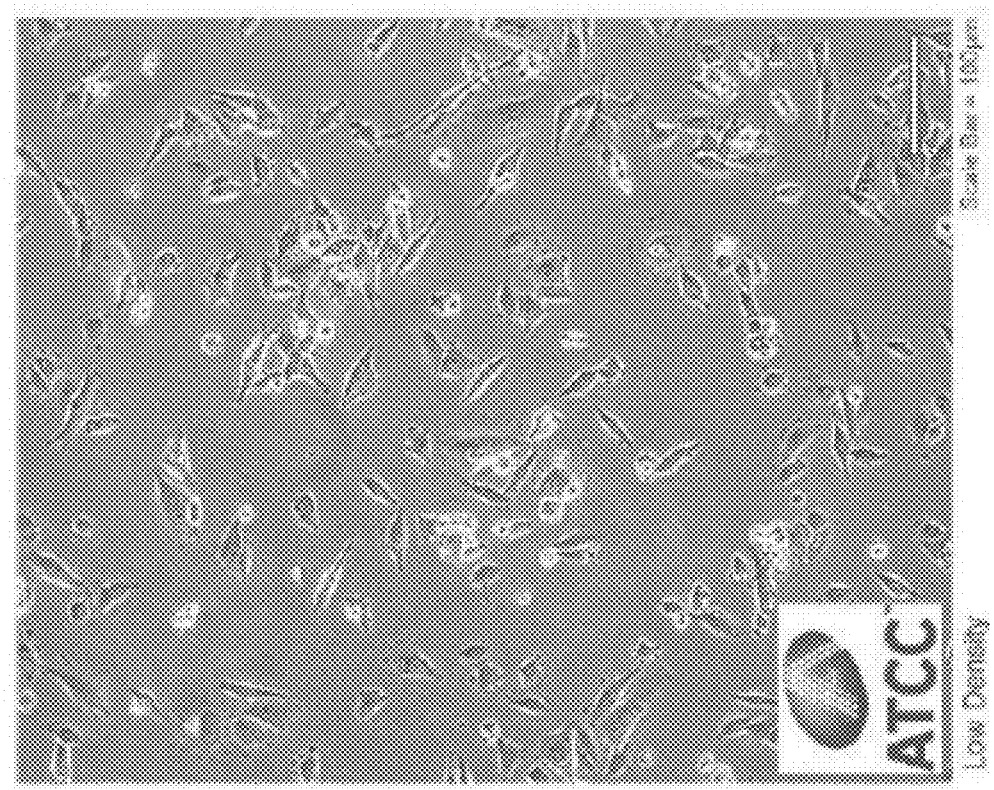
Figure 24A:
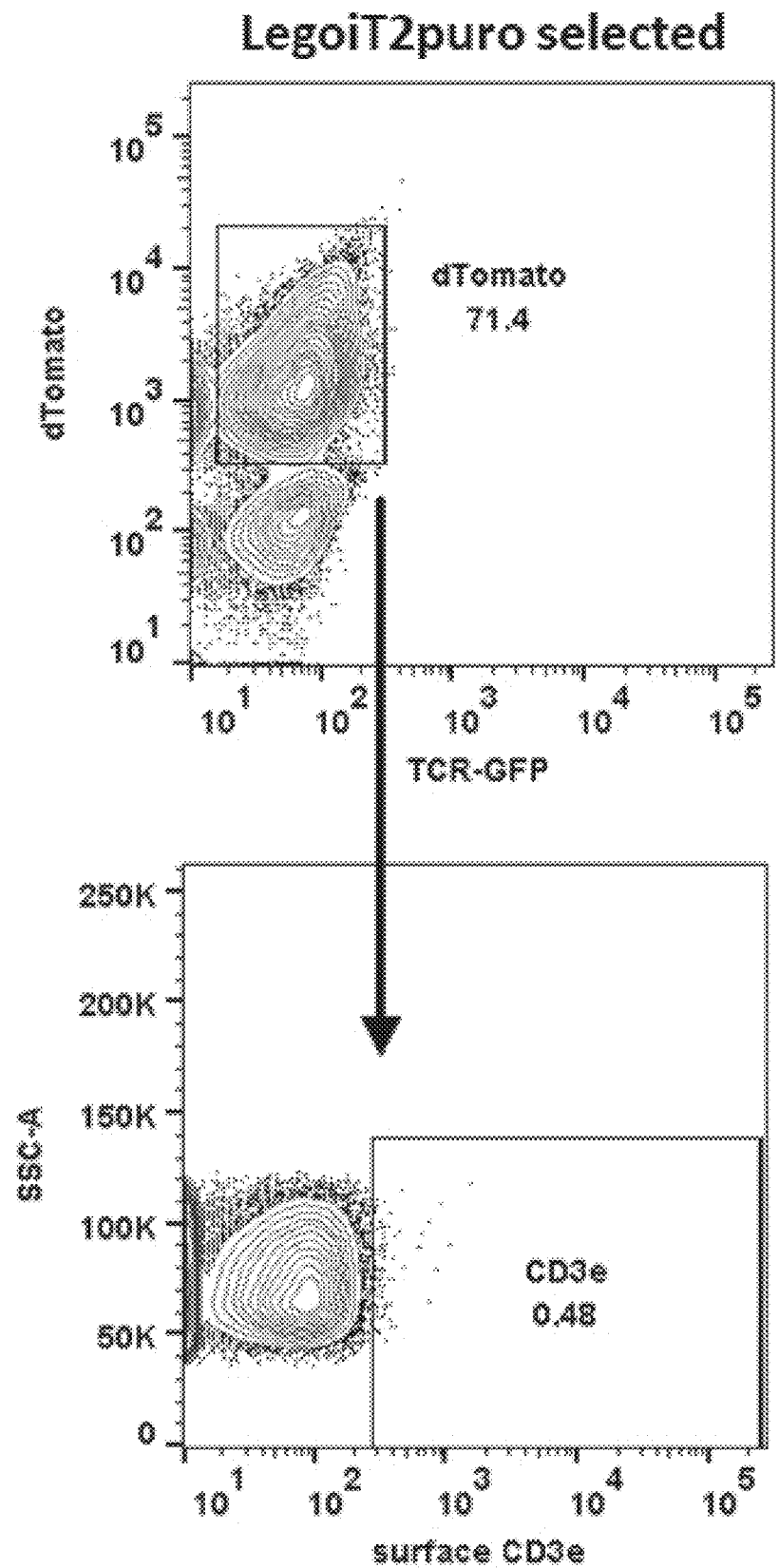
FIGS. 24A-C show surface expression of CD3e on YTS cells.
Figure 24B:
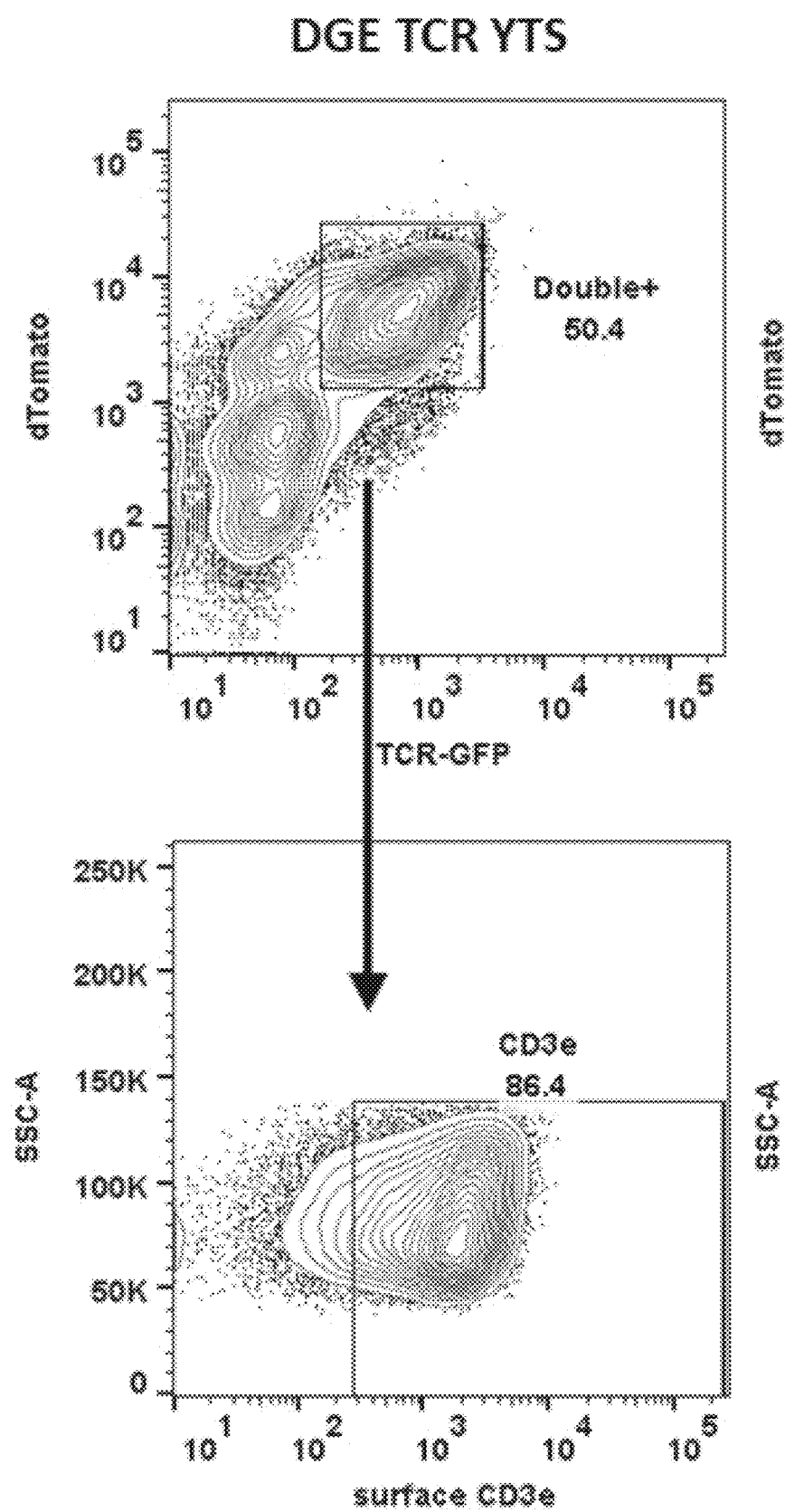
Figure 24C:
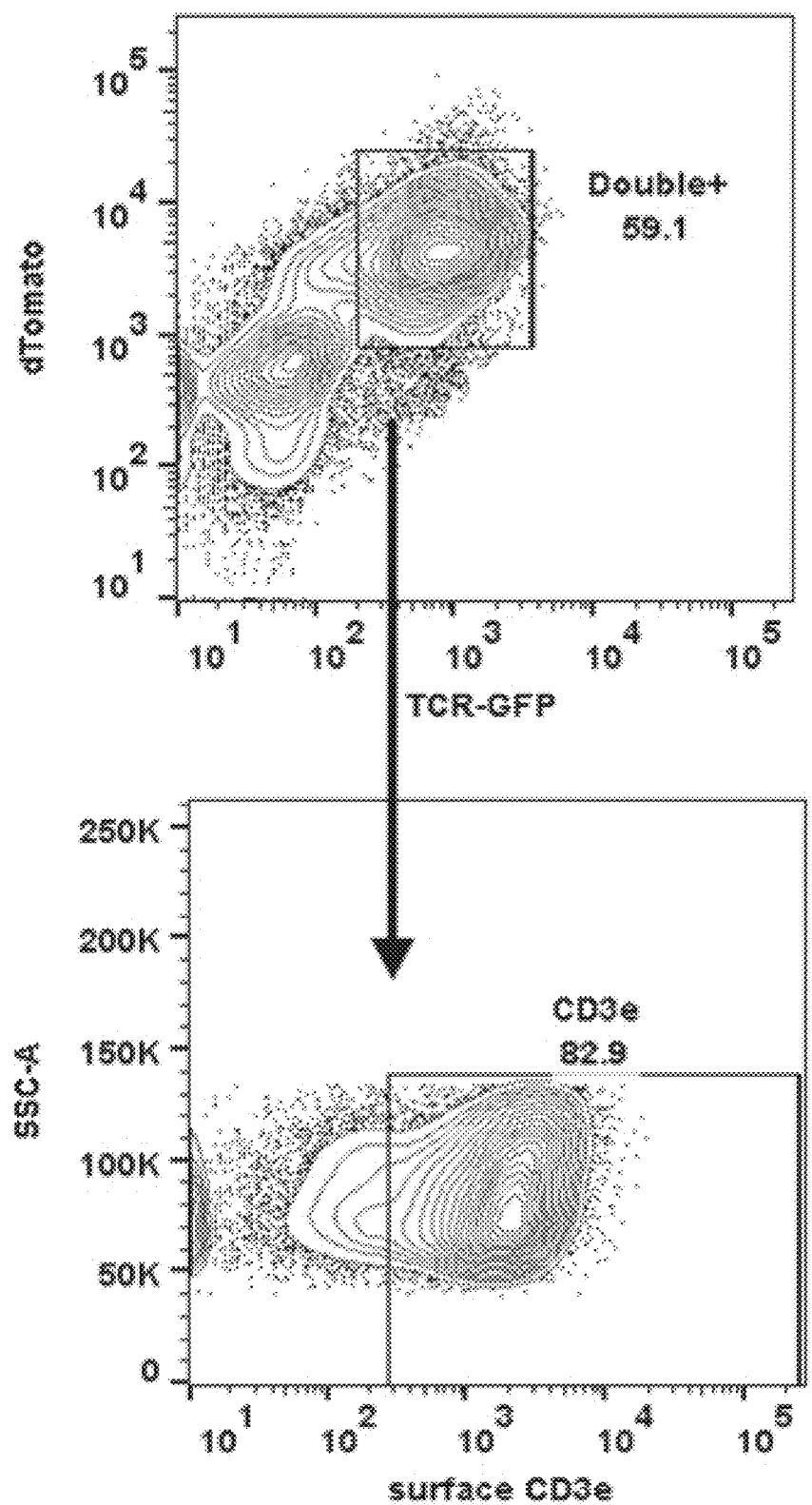
Figure 25A:
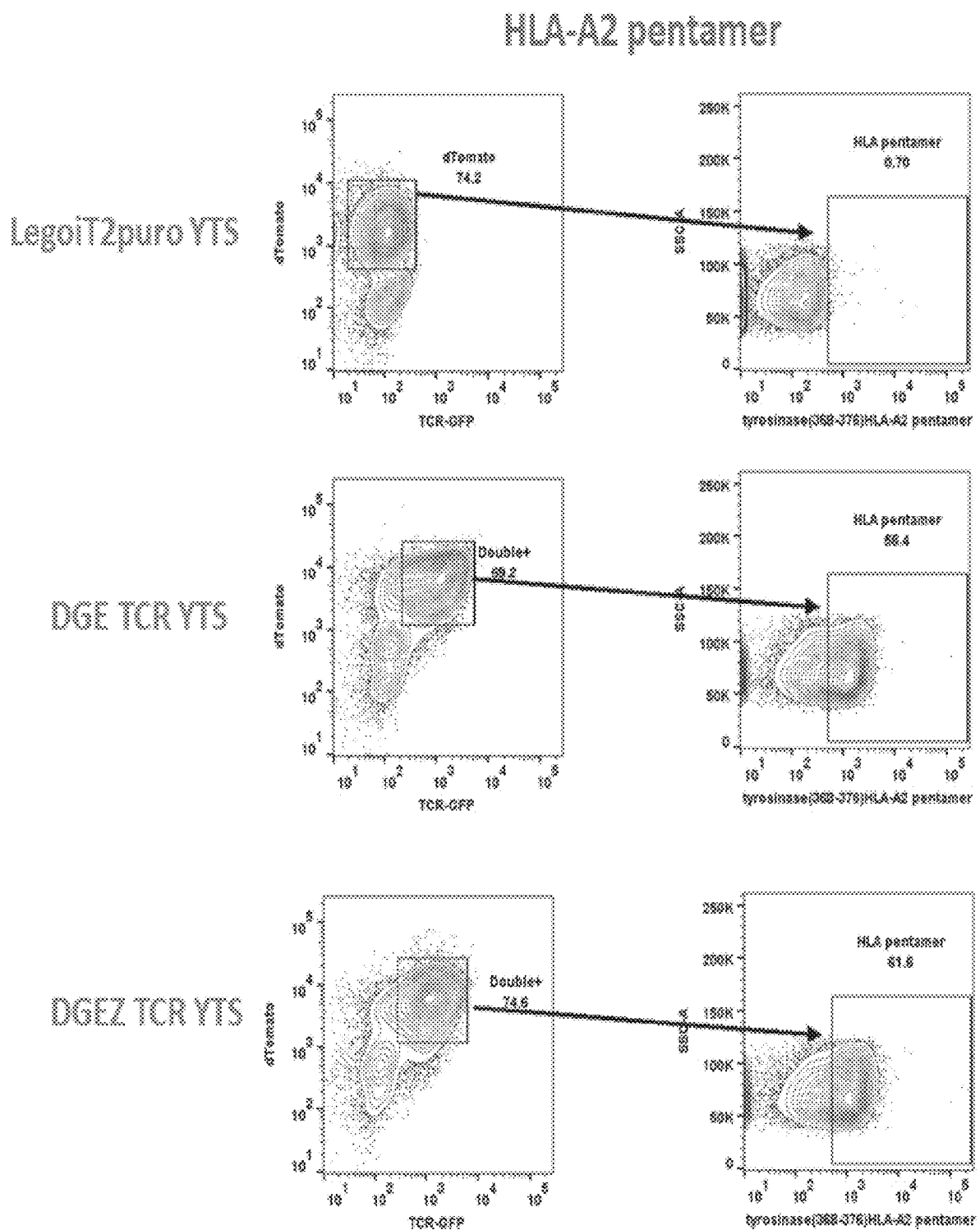
FIGS. 25A-B show data from assays using HLA-A2 pentameter and TCR antibody.
Figure 25B:
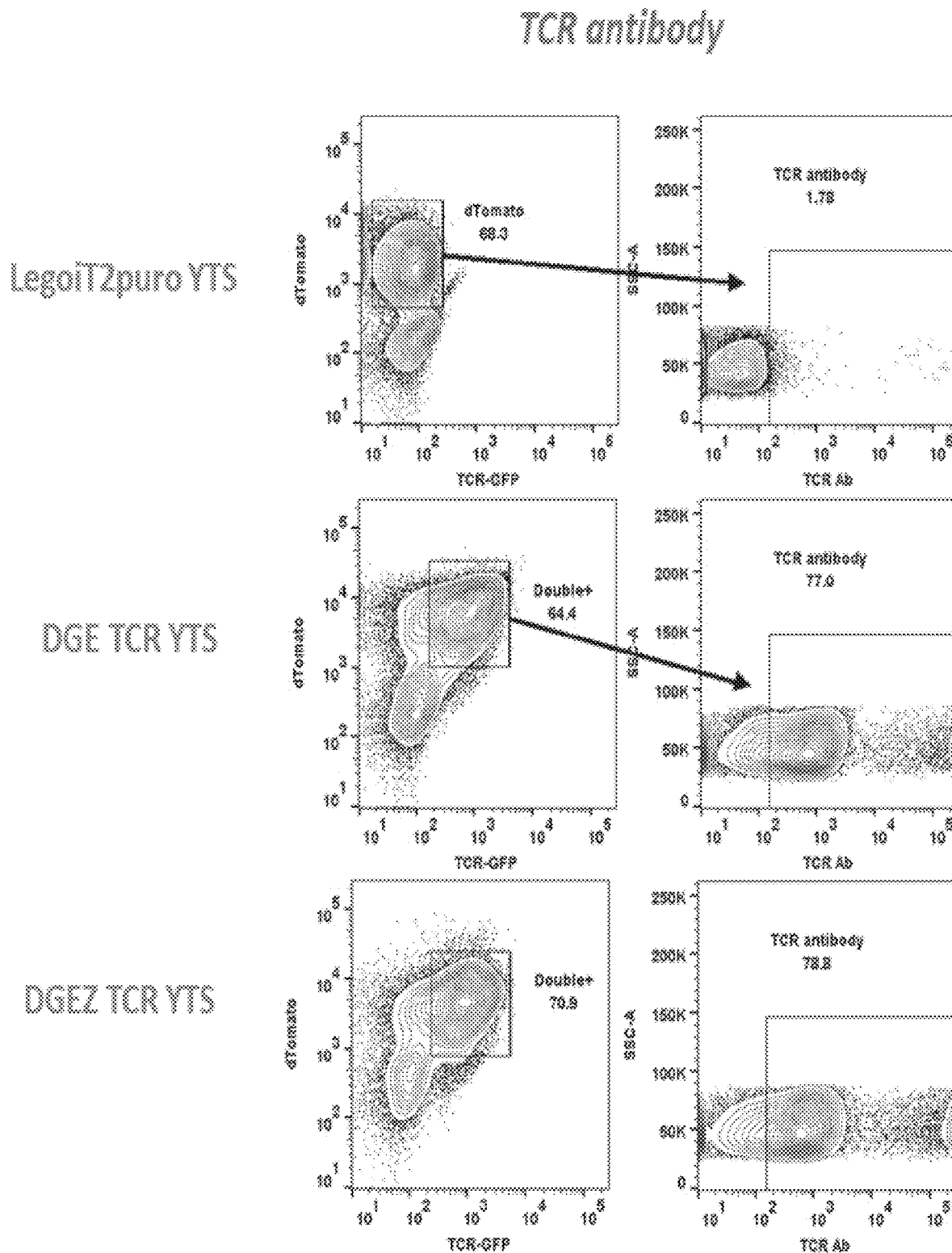
Figure 26:
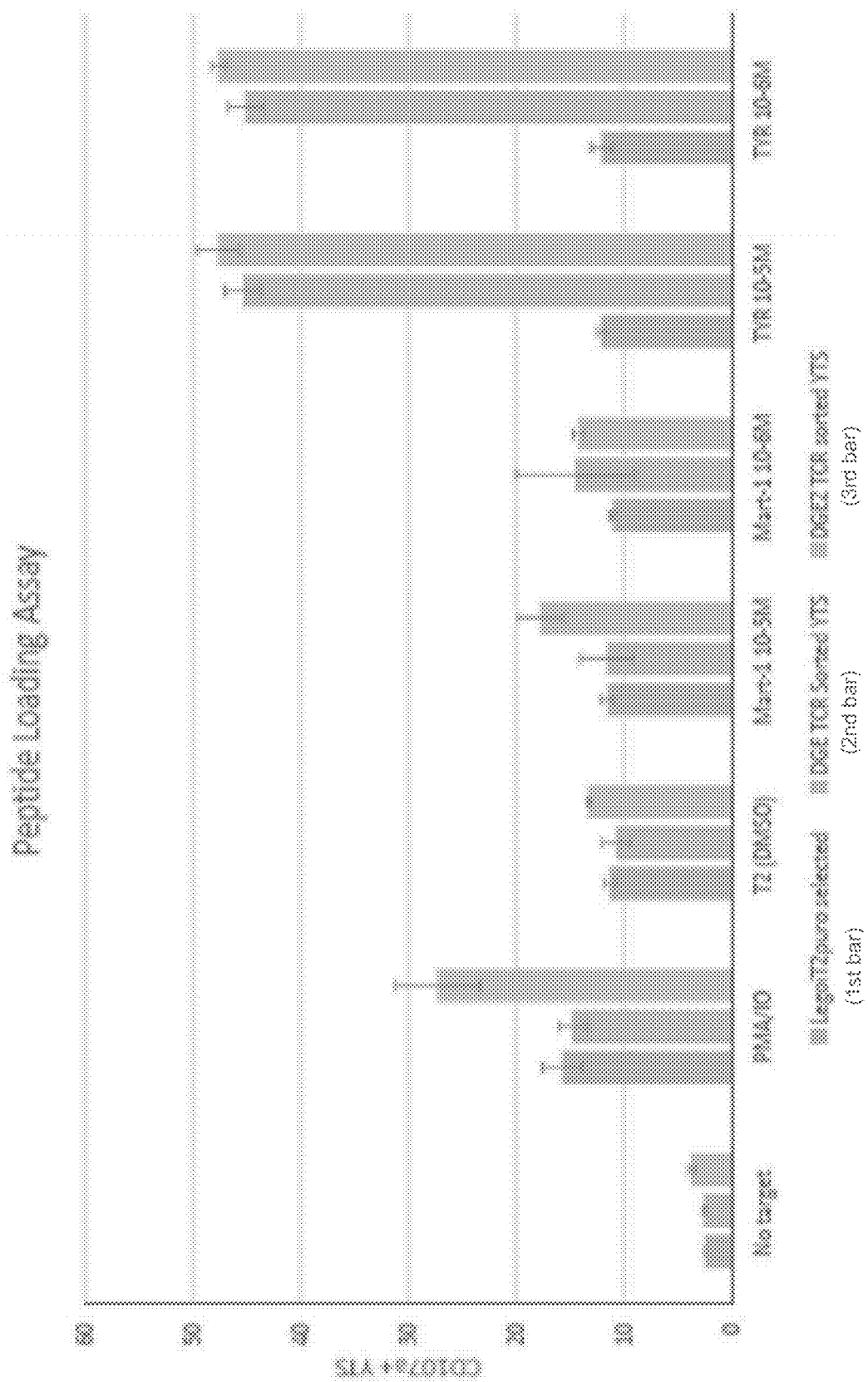
FIG. 26 is a bar graph showing CD107a degranulation of YTS TCR cells against T2 cells.
Figure 27:
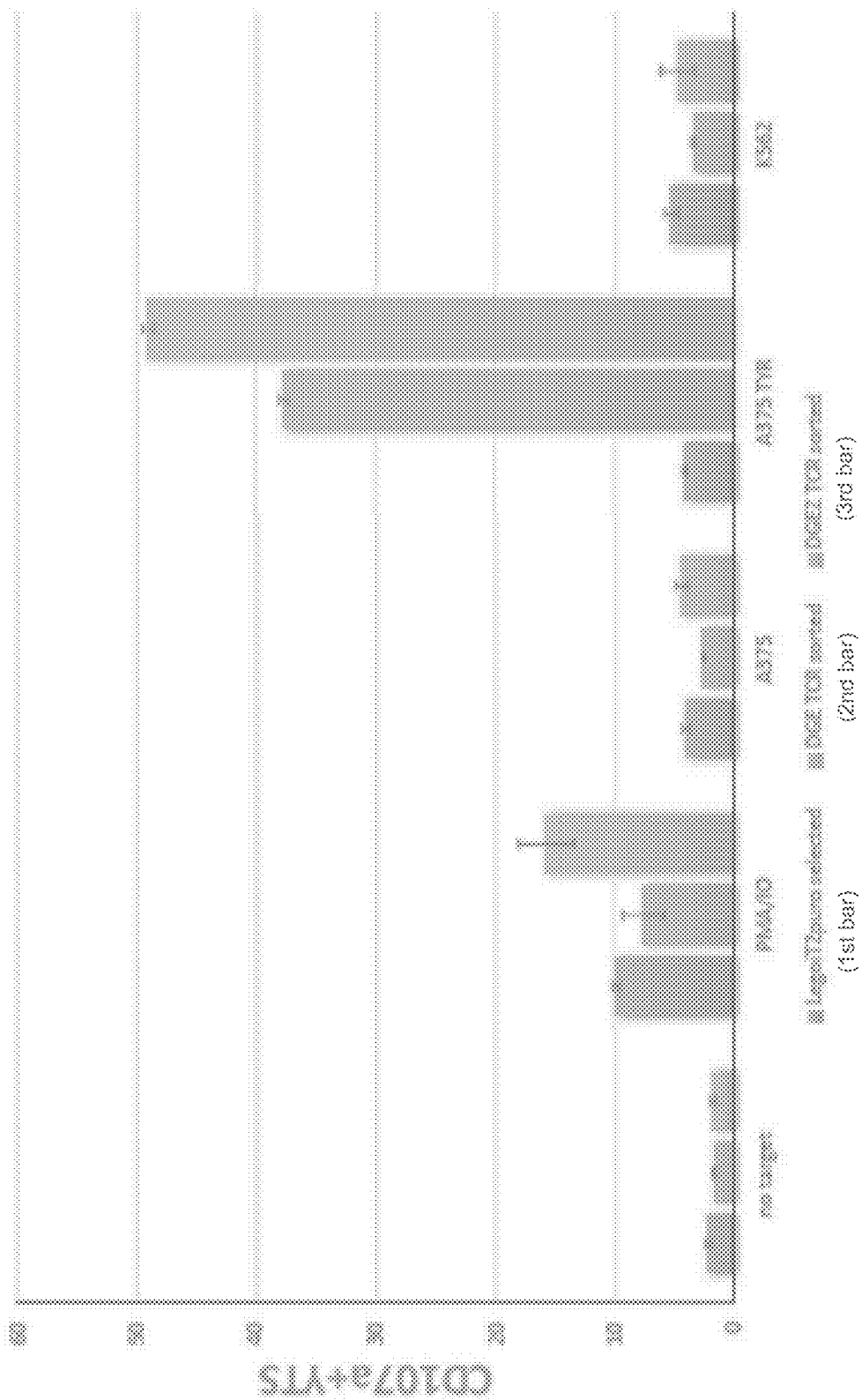
FIG. 27 is a bar graph showing CD107a degranulation of YTS TCR cells against A375 cells and A375(Tyr) cells.
Figure 28A:
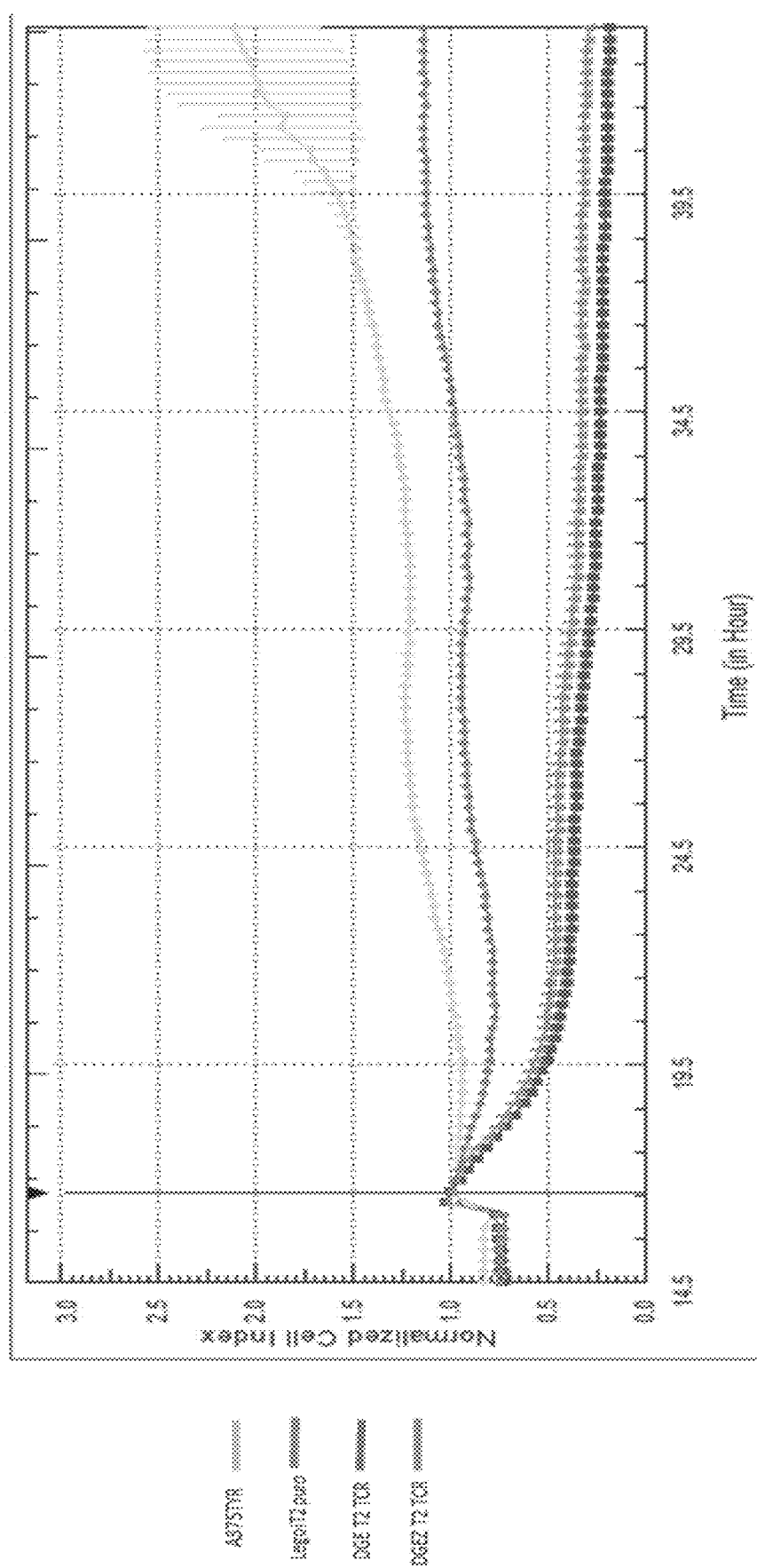
FIGS. 28A-B show results from Xcelligence® testing on YTS cells.
Figure 28B:
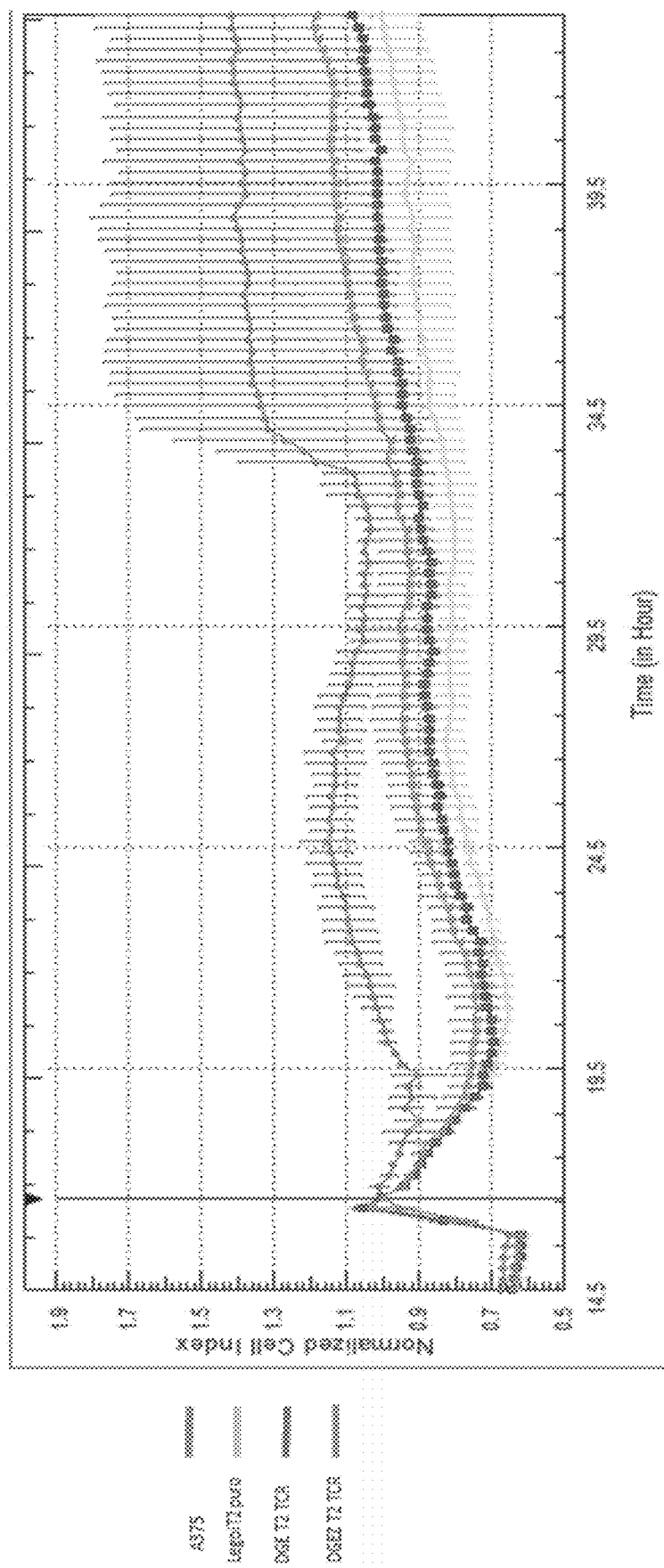
Figure 29A:
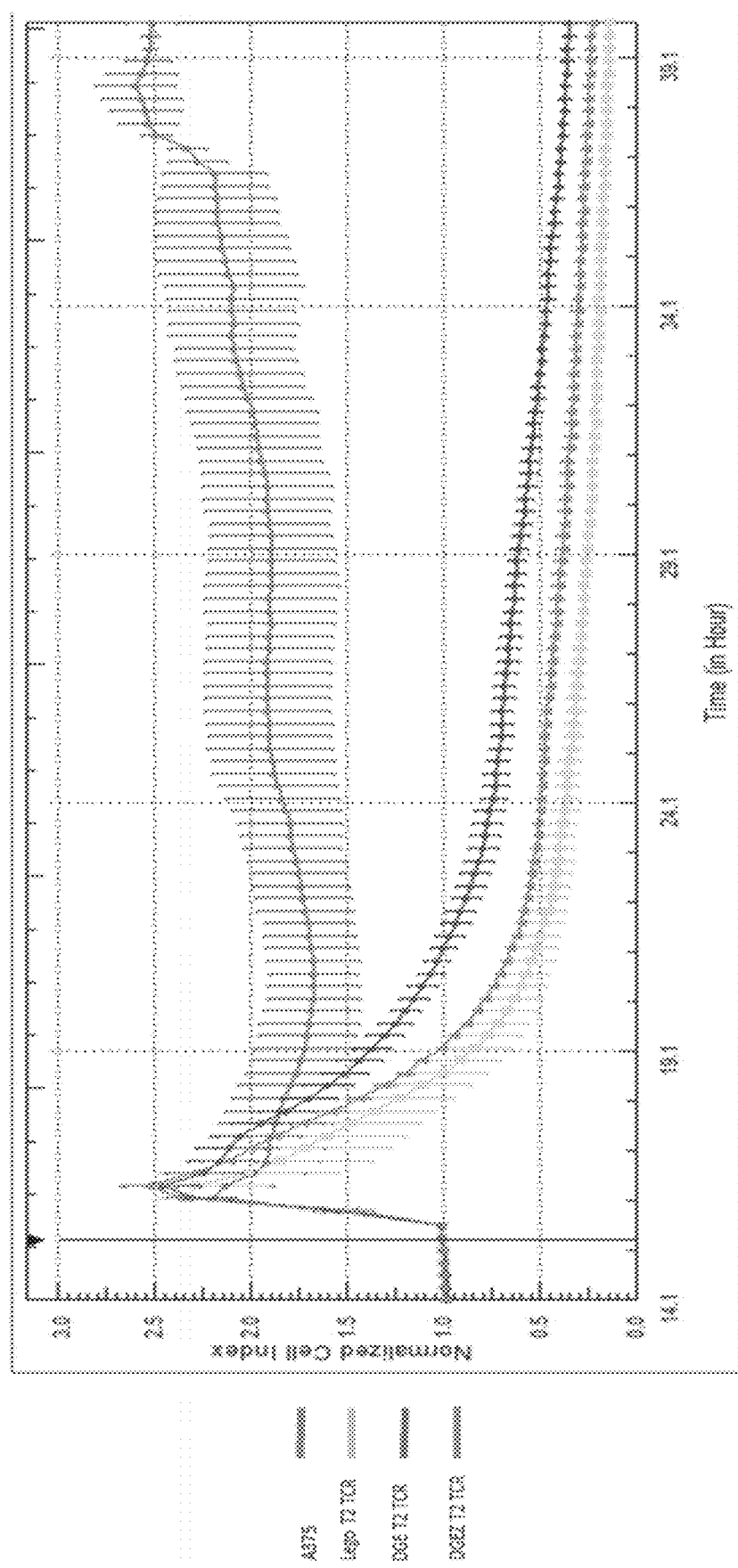
FIGS. 29A-B show results from Xcelligence® testing on NK92 cells.
Figure 29B:
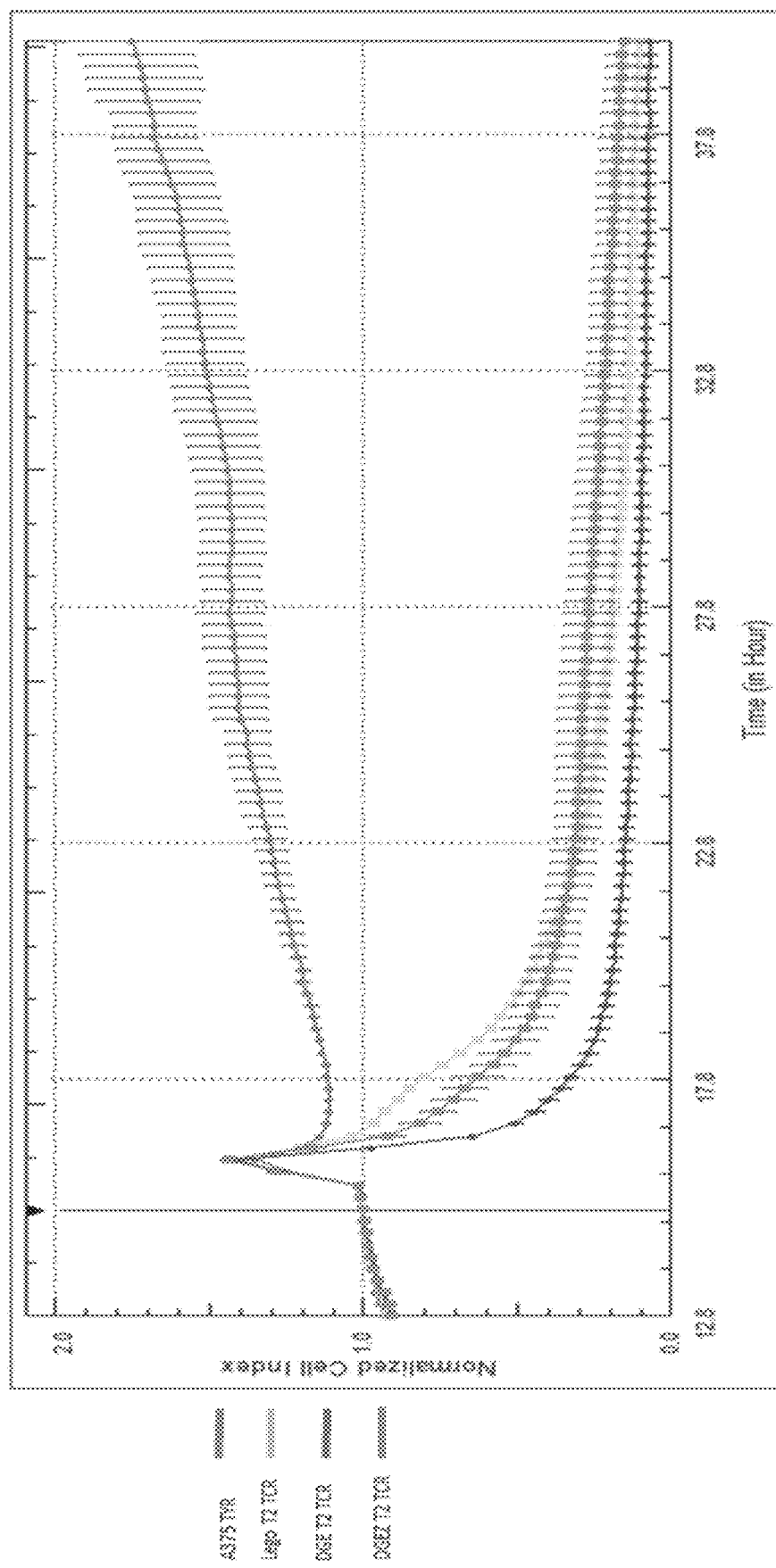

The expression of CD3δ, CD3γ, and CD3ζ in GM NK-92 and YTS cells was also characterized by immunoblotting (FIG. 31). Additionally, cell surface expression of the TCR complex was assessed by anti-TCR α/β antibody (FIG. 4D) and $Tyr_{368-379}$/HLA-A2-specific pentamers (FIG. 4F). In line with surface CD3ε expression patterns, only NK cells expressing TCR α/β together with the CD3 subunits could stably express the $Tyr_{368-379}$-specific TCR complex on the cell surface. The inclusion of ectopic CD3ζ expression appeared to only minimally increase cell surface staining of CD3ζ as well as the percentage of anti-TCR α/β$^+$ or $Tyr_{368-379}$/HLA-A2 pentamer$^+$ cells.

Figure 32:
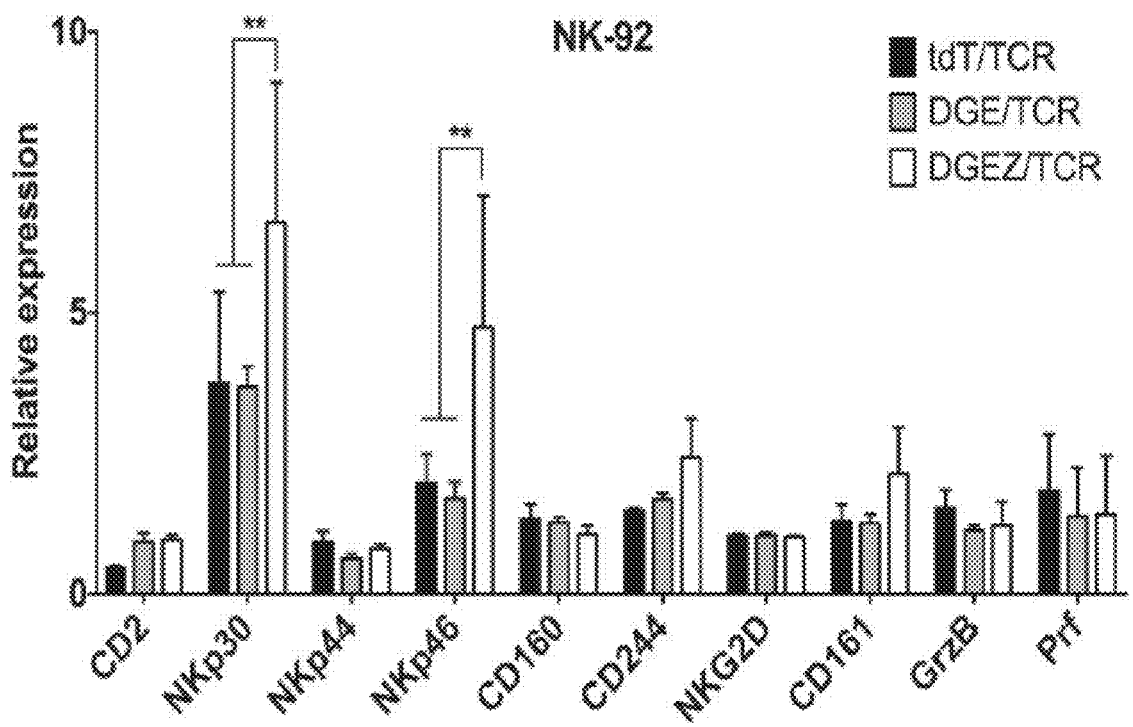
FIG. 32 is a bar graph showing flow cytometry-based phenotyping of NK cell surface receptors, intracellular Perforin (Prf), and Granzyme B (GrzB) levels for GM NK-92 cells.
Figure 33:
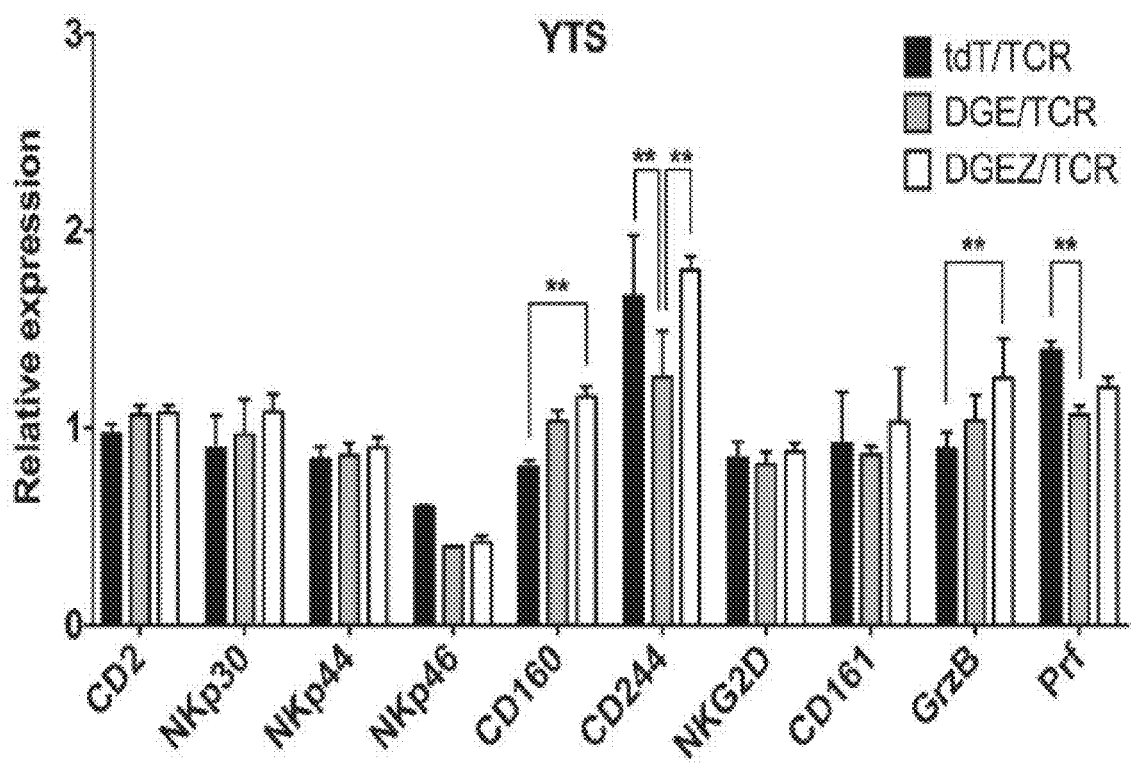
FIG. 33 is a bar graph showing flow cytometry-based phenotyping of NK cell surface receptors, intracellular Perforin (Prf), and Granzyme B (GrzB) levels for GM YTS cells.

Interestingly, flow cytometry-based phenotypic characterization of GM NK cells revealed other differences (FIGS. 32 and 33). In NK-92 cells, it was observed that the inclusion of CD3ζ in the vector resulted in significantly increased cell surface expression of the CD3ζ-coupled NK cell activating receptors; NKp30 and NKp46 (FIG. 32). In YTS cells, the overexpression of CD3ζ led to significantly higher levels of CD244 compared to DGE/TCR-expressing cells and significantly higher levels of CD160 compared to tdT/TCR expressing cells (FIG. 33). While previous data on the association of CD3ζ with CD244 (Bida, A. T. et al. 2B4 utilizes ITAM-containing receptor complexes to initiate intracellular signaling and cytolysis. *Molecular immunology* 48, 1149-1159 (2011)) may partially account for these results, the nature of the effect on CD160 remains to be elucidated at this point. Levels of intracellular Perforin and Granzyme B did not significantly change in GM NK-92 cells, while in YTS cells, elevated levels of Granzyme B in DGEZ/TCR cells and lower levels of Perforin in DGE/TCR cells were observed.

To investigate TCR-mediated antigen-specific triggering of NK cells, degranulation upon contact with the HLA-A2$^+$ T2 cell line loaded with antigenic peptides was assessed (FIG. 34A). Both DGE/TCR and DGEZ/TCR cells degranulated against mock-loaded (DMSO) and control-loaded (Mart-1) T2 cells similarly and at a slightly higher level than control cells expressing only tdT or tdT/TCR. Most importantly, T2 cells loaded with $Tyr_{368-379}$ peptide triggered degranulation by TCR-expressing NK-92 cells (FIG. 34A) at a significantly higher level, proving functionality and antigen-specificity of the introduced TCR complex.

To determine whether TCR-expressing NK cells have the capacity to recognize endogenously processed peptides in complex with HLA-A2, the response against the HLA-A2$^+$ melanoma cell line A375 and a derivative that overexpresses the tyrosinase protein; A375(Tyr) was assessed. NK cells expressing surface TCR complexes degranulated efficiently against A375(Tyr) targets (FIG. 34B) demonstrating that the introduced TCR has the capacity to recognize endogenously processed epitopes and trigger antigen-specific activation. Meanwhile, the degranulation of DGEZ/TCR expressing NK-92 cells against A375 targets were slightly elevated, hinting at a loss of antigen-specificity which could be due to the previously indicated phenotypic differences resulting from the overexpression of CD3ζ. Cytokine secretion upon co-culture of GM NK cells with A375 and A375(Tyr) targets was also analyzed. The results show high levels of antigen-specific TNF-α and IFN-γ secretion by TCR expressing NK cells upon triggering by A375(Tyr) cells as assessed by antibody arrays (FIGS. 34C-D) as well as flow cytometry (FIGS. 34E-F).

Collectively, these data show that NK cells expressing CD3δ, CD3γ, CD3ε and TCRα/β can detect antigenic peptides presented by MHC-I and selectively trigger effector functions. The inclusion of CD3ζ in vector design does not increase antigen-specific triggering but on the contrary, might increase background activity against non-specific targets.

To demonstrate the dynamics of antigen-specific responses, the cytotoxic activity of GM NK cells using electrical impedance-based analysis of A375 and A375(Tyr) cell survival upon co-culture with GM NK cells was analyzed. The results demonstrate that TCR expressing NK cells efficiently and specifically kill tyrosinase expressing targets (FIGS. 35A-B). Quantification of cytotoxic activity at the 4 h time-point (FIGS. 35C-D) during real-time cell analysis (RTCA) demonstrates the efficient and TCR-dependent cytotoxic activity against A375(Tyr) at various E:T ratios.

Figure 36B:
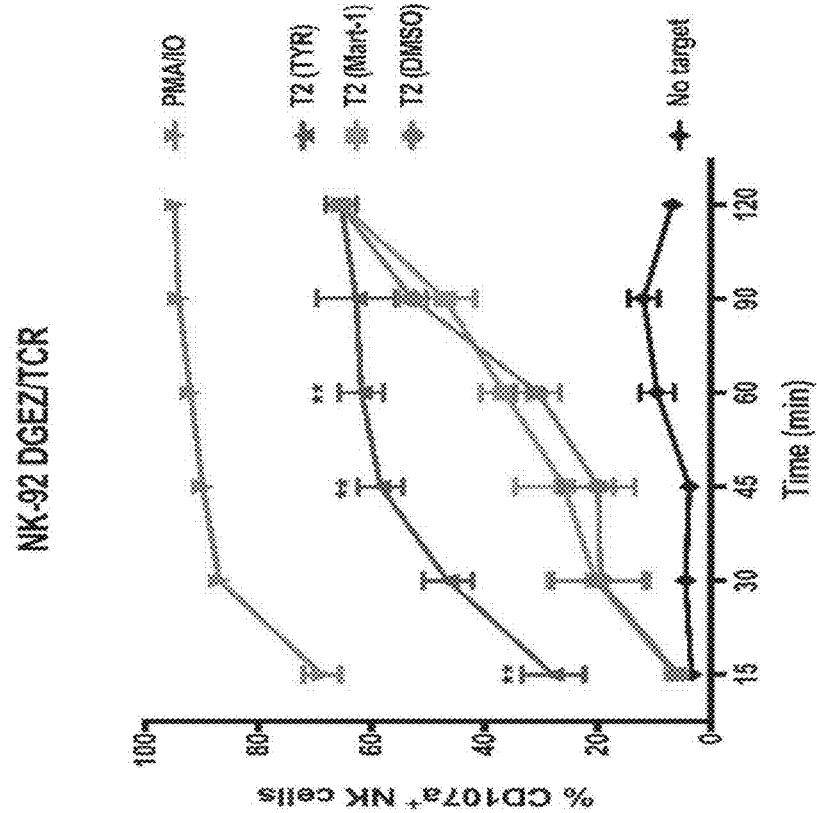
FIGS. 36A-B are graphs showing cell surface expression levels of CD107a on NK cells (indicative of degranulation). Cell surface expression levels were measured upon target cell exposure at a 1:1 ratio. T2 cells loaded with indicated peptides ($10^{-6}$M) or DMSO were mixed with NK-92 DGE/TCR or NK-92 DGEZ/TCR cells. Significant differences in degranulation against T2(Tyr) cells compared to T2(Mart-1) and T2(DMSO) cells are demonstrated on the plots. ($p<0.005$; *$p<0.0005$; ****$p<0.0001$, one-way ANOVA).
Figure 36A:
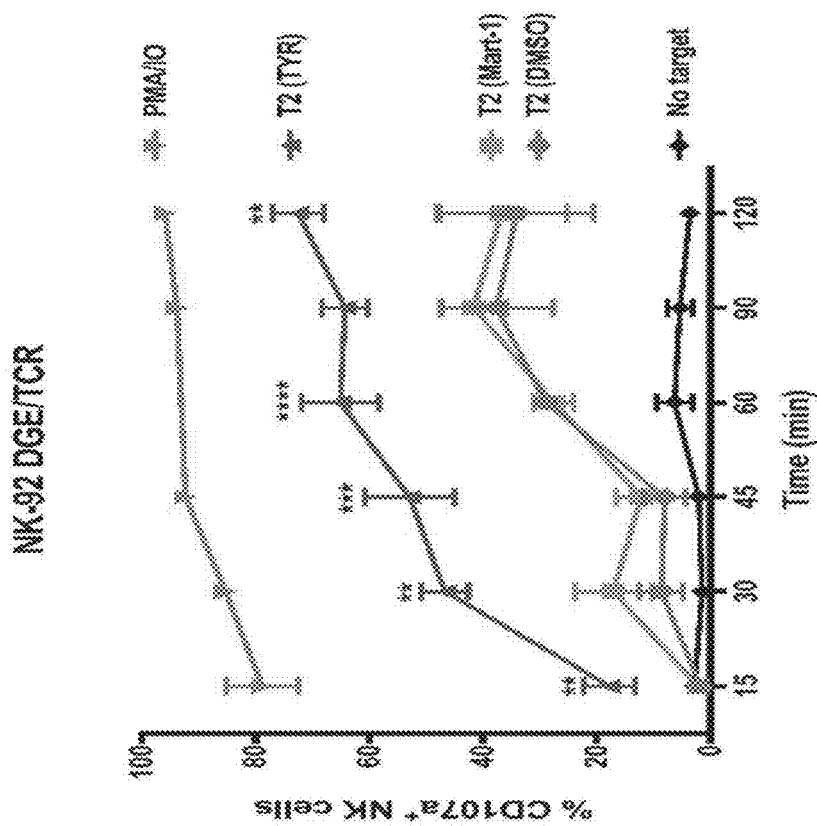
Figure 37A:
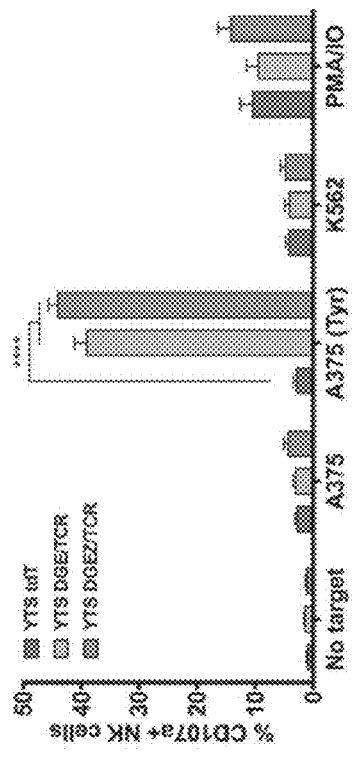
FIGS. 37A-D show data illustrating in vitro cytotoxic activity of TCR-expressing YTS cells.
Figure 37B:
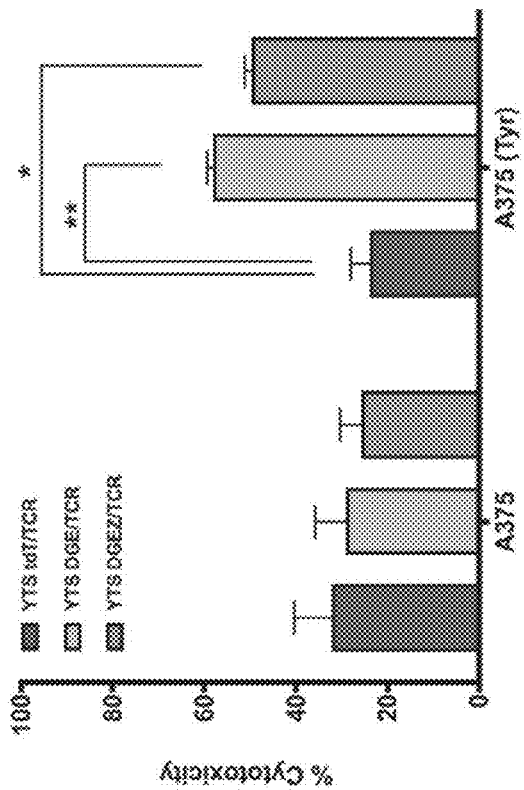
Figure 37C:
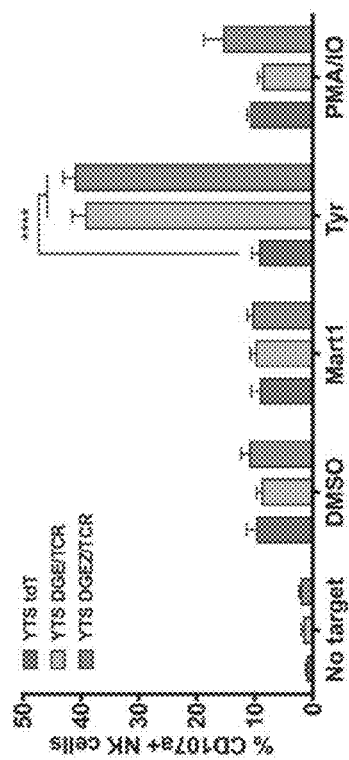
Figure 37D:
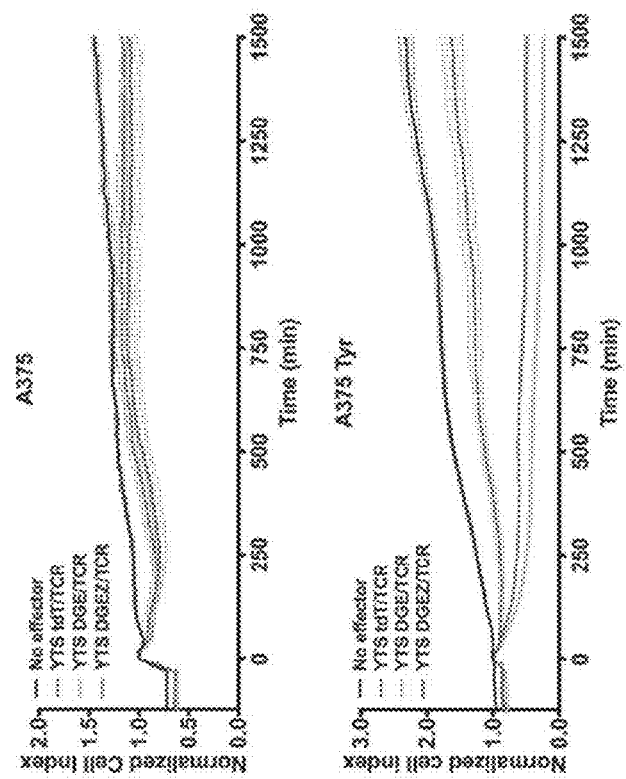

To further observe the dynamics of cytotoxic activity, live cell imaging of GM NK-92 cells in co-culture with A375 and A375(Tyr) targets was performed. Over a 2-hour period, NK-92 cells were observed to contact and rapidly induce apoptosis in A375(Tyr) targets. In line with this observation, GM NK-92 cells degranulated robustly against Tyr368-379-loaded T2 cells, as early as 15 minutes after co-culture initiation, while such effects were not observed against Mart-1 loaded T2 cells (FIGS. 36A-B).

Figure 38:
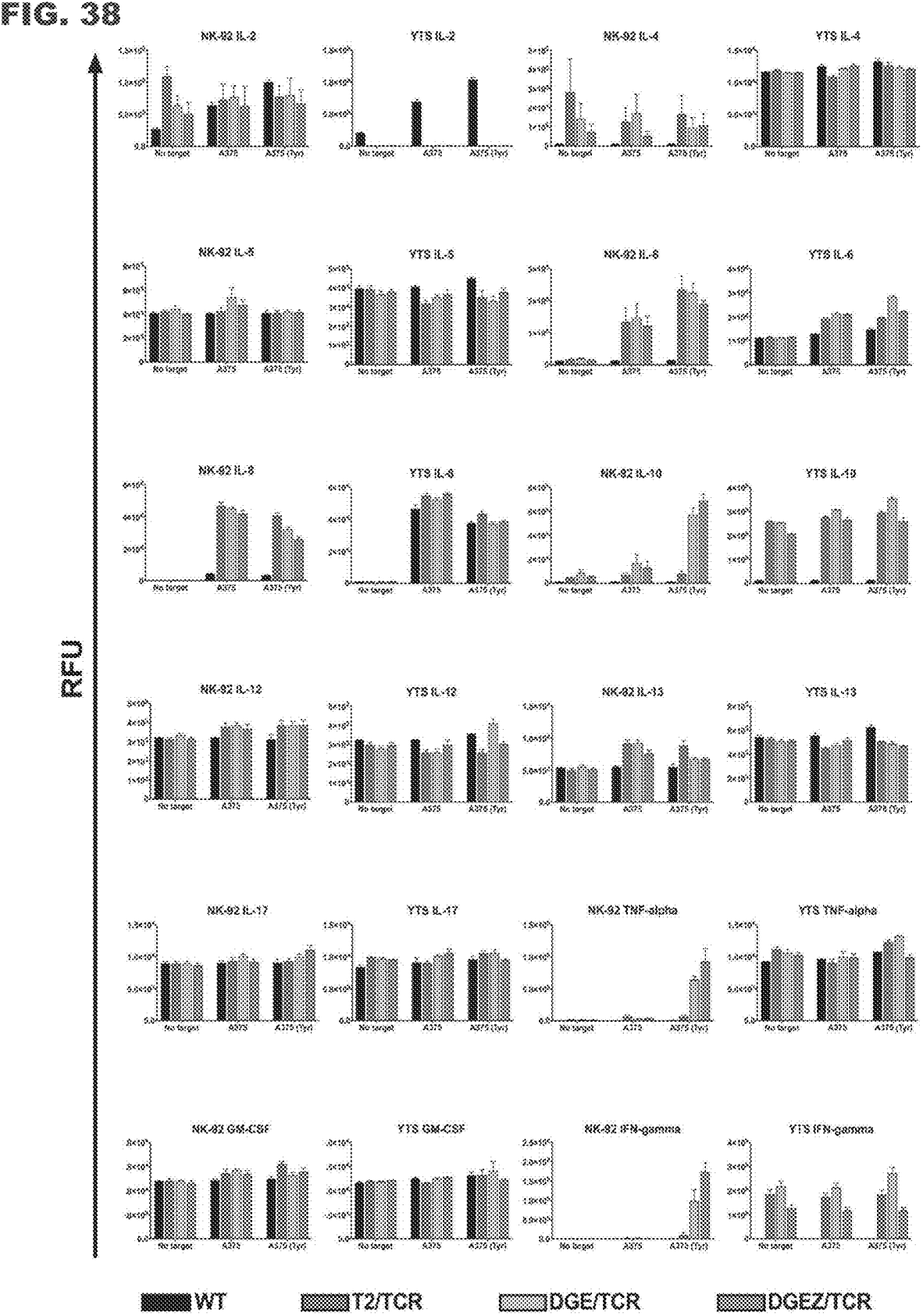
FIG. 38 is a cytokine secretion profile of GM NK-92 cells and GM YTS cells. Cytokine secretion was assessed by Pathscan Th1/Th2/Th17 cytokine antibody array after co-culture of cells with A375 or A375(Tyr) targets. RFU: relative fluorescence unit.

Similar results were recorded with GM YTS cells regarding antigen-specific degranulation, and cytotoxic activity while no loss of specificity was observed in YTS cells with ectopic CD3ζ expression (FIGS. 37A-D). In YTS cells, high levels of IL-10 and IFN-γ secretion were observed but no antigen-specific increase in cytokine secretion could be detected using antibody arrays (FIG. 38).

In an effort to simplify the process of genetic modification, lentiviral vectors encoding both the CD3 subunits and the TCR chains in a single plasmid were designed (FIG. 39A). NK-92 cells were transduced in a single-step with DGEiTCR or DGEZiTCR vectors and were enriched by FACS after staining for surface CD3(e) expression. In line with the results observed with the two-step GM cells, NK-92 cells transduced with single vectors expressing DGEiTCR or DGEZiTCR demonstrated antigen specific degranulation against A375(Tyr) and most importantly efficient killing activity against A375 cells expressing the tyrosinase antigen in vitro (FIG. 38).

The in vivo efficacy of GM NK cells against tyrosinase expressing tumor cells using a NOD/SCID animal model was investigated (FIGS. 35E-F). It was observed that after two doses of GM-NK cell injections, mice treated with NK-92 cells expressing DGE-TCR and DGEZ-TCR had smaller A375(Tyr) tumors than A375 tumors, already at day 6 and significantly smaller A375(Tyr) tumors at day 10 (FIG. 35F). These results indicate that TCR expressing NK-92 cells can efficiently target tumor cells expressing the cognate antigen/MHC complex in vivo and restrict tumor growth.

To the knowledge of the instant inventors this is the first proof-of-principle study demonstrating the capacity of NK cells eliciting MHC-restricted antigen-specific in vivo cytotoxicity against intracellular antigens. These experiments show that the delivery of TCR α/β genes into NK cells along with CD3 δ, γ, ε chains, but not necessarily CD3ζ, enables the surface expression of functional TCR complexes specific to a tyrosinase epitope ($Tyr_{368-379}$) in complex with HLA-A2. This strategy provides a novel source for cellular immunotherapy and presents a possible solution for the mispairing problem in TCR gene therapy.

The data demonstrates that the ectopic expression of CD3δ, CD3γ, CD3ε and TCR α/β heterodimer is necessary for establishment of a TCR complex on the surface of NK-92 and YTS cells. Owing to the native CD3ζ expression in NK cells, the inclusion of CD3ζ ectopic expression is not crucial but an abundance of CD3ζ may increase the efficiency of the TCR-complex assembly at the cell surface. However, the inclusion of CD3ζ seems to influence NK cell phenotype and the functional outcomes of these differences need to be carefully monitored.

Expressing functional TCRs on NK cells stands out as a unique discovery combining the robust and effective cytotoxic capacity of NK cells with the exclusive antigen specificity of T cells. This presents a novel approach to develop adoptive immunotherapy for cancer and viral infections. This study demonstrates the feasibility of functional TCR-expression in NK cells using an MHC-I-restricted TCR α/β heterodimer that functions independently of the co-receptors CD4 and CD8. While it remains unknown whether co-receptor-dependent TCRs can also confer antigen specificity to NK cells, it is possible to include CD4 or CD8 in the design of the genetic modification process. Testing this approach with different TCRs targeted against tumor-associated or viral antigens is warranted.

While further studies to better characterize the pros and cons of this approach compared to using T cells are necessary, this study presents a novel approach in immunotherapy. This study underlines the value of NK cells as a resource that has similar cytotoxic capacity with T cells but present themselves unburdened from endogenous TCR expression. These results demonstrate that the use of TCR-modified NK cells (NK-TCR) can overcome the major hurdle of "mispairing" in TCR gene therapy while enabling the targeting of intracellular antigens.

Protocols: (Methods and Materials)
Cell Lines

293FT cells were maintained in Dulbecco's Modified Eagle Medium (DMEM) (GIBCO) supplemented with 10% Fetal Bovine Serum (FBS) (GIBCO), 0.1 mM non-essential amino acids (NEAA) (Sigma-Aldrich, St. Louis, Mo., USA), 6 mM L-glutamine (Sigma-Aldrich), 1 mM sodium pyruvate (Sigma-Aldrich) and 20 mM HEPES (Sigma-Aldrich). NK-92 cells were maintained in CellGro SCGM (Cellgenix) medium supplemented with 20% FBS and 1000 U/ml rhIL-2 (Proleukin, Novartis). K562, A375 and A375(Tyr) (kind gift from Prof. Michael Nishimura, Loyola University Chicago) and T2 cells were maintained in RPMI-1640 medium (GIBCO) supplemented with 10% FBS. YTS cells were maintained in RPMI 1640 supplemented with 20% FBS, 1 mM Sodium Pyruvate, 0.1 mM NEAA, 20 mM L-Glutamine, 1× MEM Essential Vitamin Solution and 0.1 mM beta-mercaptoethanol.

Production of Lentiviral Vectors

For production of VSV-G pseudotyped lentiviral vectors, $14 \times 10^6$ 293FT cells were plated into a poly-D-lysine coated 150 mm dish (BD Biosciences, San Jose, Calif., USA). The following day cells were transfected with 30 μg of vector plasmid (LeGO vectors courtesy of Prof. Boris Fehse, University Medical Center Hamburg-Eppendorf, Hamburg, Germany), 15 of pMDLg/pRRE (Addgene, Cambridge, Mass., USA), 10 μg of pRSV-REV (Addgene) and 5 of phCMV-VSV-G (Addgene) using a calcium phosphate transfection kit (Sigma-Aldrich) in the presence of 25 μM Chloroquine (Sigma-Aldrich). 10 hours after transfection, the medium was changed and thereafter virus containing supernatant was collected every 24 hours for 2 days and stored in −80° C. until further use. A small aliquot from each production was used to determine viral titers by transduction of 293FT cells with serially diluted amounts of virus supernatant.

Lentiviral Transduction of NK Cells

For each lentiviral transduction, $0.25 \cdot 10^6$ NK-92 or YTS cells per well were seeded in a 24-well plate (BD Biosciences) and mixed with an appropriate amount of virus supernatant in the presence of 8 μg/ml of protamine sulfate and 3 μM BX795 (Sigma-Aldrich) in a final volume of 1 ml. The plates were incubated at 37° C., 5% $CO_2$ for 6 hours. At the end of the incubation, cells were spun down at 300×g for 10 minutes at room temperature after which the supernatants were removed from the wells and 1 ml of fresh growth medium per well was added. The cells were maintained in this medium for at least 3 days before expression of the transgene on the transfected cells was confirmed.

Flow Cytometry

The antibodies used for labeling NK cells were CD56 (NCAM16.2), CD3e (UCHT1), NKp30 (p30-15), CD244 (2-69), NKp44 (p44-8) from BD Biosciences and CD2 (RPA-2.10), NKG2D (1G11), NKp46 (9E2), CD161 (HP-3G10), CD160 (BY55), Perforin (dG9) and Granzyme B (GB11) from Biolegend.

All antibody stainings for flow cytometry were done according to the following protocol: For surface staining, the cells were washed once with PBS (containing 2% FBS and 1 mM EDTA) and incubated with appropriate amounts of antibody at 4° C. for 30 min. The labeled cells were then washed with PBS and data acquisition was performed. For intracellular staining, cells were fixed and permeabilized for 15 minutes in a solution containing 2% PFA in 1× Permeabilization Wash Buffer (BioLegend), washed two times with Permeabilization Wash Buffer and incubated with appropriate amounts of antibody at 4° C. for 30 min. The labeled cells were then washed with Permeabilization Wash Buffer and data acquisition was carried out. For data acquisition, FACSCanto (BD Biosciences), LSR Fortessa (BD Biosciences) or NovoCyte 3000 (ACEA Biosciences) instruments were used depending on availability. Data was analyzed with the FlowJo v10.1 software (TreeStar Inc.).

Intracellular Cytokine Staining

NK-92 cells were co-incubated with A375 target cells at a ratio of 1:1 in a final volume of 200 µl in V-bottomed 96-well plates at 37° C. and 5% $CO_2$ for 5 h. PMA and ionomycin stimulation was used as a positive control for activation. After 1 h of co-incubation, GolgiStop (BD) was added at a 1:200 dilution. After additionally 4 hours of co-incubation, the cells were first stained for surface expression with BV510-CD56 (BD Biosciences) at 4° C. for 20 minutes and then washed with PBS. The cells were then fixed with Fixation Buffer (BD Biosciences) and later stained with APC:IFNγ (Biolegend) and APC-TNFα (Biolegend) following the manufacturer's protocol. Flow cytometry data acquisition was performed by LSR Fortessa X20 (BD Biosciences) and the data was analysed using the FlowJo v10.1 software (TreeStar Inc.).

Western Blot Analysis

Cells were lysed in lysis buffer (1% Triton X-100, 0.15M NaCl, 0.002M EDTA (pH 8.0) and 0.05 M Trizma [pH 7.4]) and protease inhibitors (11836153001, Sigma Aldrich). Protein content was measured by Bradford assay (B6916, Sigma Aldrich), and analyzed under reducing conditions with 12% SDS-PAGE, followed by electroblotting on PVDF transfer membranes (Thermo Scientific). The membranes were blocked with 5% skimmed milk (Sigma Aldrich). Membranes were incubated overnight at 4° C. with the indicated primary antibodies. The dilutions of antibodies were prepared as follows: mouse anti-CD 247 (BD Pharmingen, 1:500), rabbit pAb CD3δ (Abcam, 1:300), goat pAb CD3γ (Abcam, 1:300), rabbit anti β-actin pAb HRP conjugate (Cell Signaling Technology, 1:2000). After washing, membranes were treated with horseradish peroxidase-conjugated secondary antibodies, donkey Anti-goat IgG-HRP (Santa Cruz Biotechnology, 1:2500) incubated overnight at 4° C., rabbit Anti-Mouse IgG-HRP (Sigma Aldrich, 1:80000) and goat Anti-Rabbit IgG-HRP (Cell Signaling Technology, 1:20000) incubated 1 hour at room temperature. Then the bands were visualized using ECL (0.45 mM Luminol, 0.625 mM Coumaric Acid, 0.07M Trizma [pH 8.8]) in Luminescent Image Analyzer (Image Quant LAS 4000 mini, GE Healthcare Life Sciences).

Peptides and HLA A2 Pentamers

Tyrosinase$_{(368-379)}$ (SEQ ID NO:1) and Melan-A/Mart-1$_{(27-35)}$ (SEQ ID NO:2) peptides as well as APC conjugated Tyrosinase$_{(368-379)}$/HLA-A2 pentamers were purchased from ProImmune Ltd. $0.5\times10^6$ NK-92 cells were washed once with PBS and incubated with 10 ul of Tyrosinase$_{(368-379)}$/HLA-A2 pentamers at 4° C. for 30 min. The labeled cells were then washed PBS twice and data acquisition was carried out.

Analysis of Cytokine Secretion by Antibody Array

For analysis of cytokine secretion in co-cultures of effector and target cells, PathScan® Th1/Th2/Th17 Cytokine Antibody Array Kit (Cell Signaling Technology) with Fluorescent Readout was used according to manufacturer's instructions. Briefly, $0.5\times10^6$ targets cells were mixed at 1:1 ratio with effector cells in 24-well plates at a final volume of 1.5 ml and incubated for 6 hours at 37° C. %5 $CO_2$. At the end of the incubation period, cell suspensions were transferred into microcentrifuge tubes and centrifuged at 500×g for 5 min. Supernatants were collected and filtered through a 0.22 µM syringe filter before application on to slides. The antibody array was used according to the kit protocol, using 75 µl of supernatant and slides were scanned using the Odyssey CLx Imaging System (LI-COR Biotechnology).

Analysis of NK Cell Degranulation

TAP-deficient T2 cells were pulsed with different concentrations of indicated peptides in serum free RPMI medium at 26° C. overnight in 5% $CO_2$. Cells were subsequently washed and incubated in RPMI medium at 37° C. for 60 min. NK-92 or YTS cells were co-incubated with peptide loaded T2 cells or A375 target cells at a ratio of 1:1 in a final volume of 200 µl in round-bottom 96-well plates at 37° C. and 5% $CO_2$ for 6 h. Fluorochrome-conjugated anti-CD107a (H4A3—Biolegend) mAb was added at the initiation of the assay. After 1 h of co-incubation, Monensin (Biolegend) was added at a 1:100 dilution. At the end of 6 h, the cells were washed, resuspended in ice-cold PBS and immediately analyzed by flow cytometry.

Analysis of NK Cell Cytotoxicity by Xcelligence RTCA

Real time cell viability experiments were performed using the xCELLigence RTCA DP device (ACEA Biosciences) placed in a humidified incubator at 37° C. and 5% $CO_2$. The E-16 plates were incubated with 100 µl of cell-free growth medium (10% FBS) at room temperature for 15 min. After incubation background impedance signal was measured to control all the connections. The target cells were seeded into E-16 plates at indicated concentrations which are $1\times10^4$ in 100 µl for A375 Tyr cells and $1.5\times10^4$ in 100 µl for A375 cells. The plates were mounted to the device and incubated for 30 min before starting the experiment. The target cells were allowed to grow for about 14-16 h before adding effector cells. The following day, the effector cells were added onto the target cells at an E:T ratio of 1:1. Real time measurements were performed by recording the Cell index (CI) every 15 min, for 40 h. Data analysis was carried out with the RTCA software (version 1.2, Roche Diagnostics).

Live Cell Imaging

For live cell imaging $0.25\times10^6$ A375 or A375(Tyr) cells were seeded in 6-well plates with glass coverslips (0.17 mm thickness, 25 mm diameter) at the bottom and left to grow overnight. The next day, the coverslips were removed from the plates, rinsed once with PBS and mounted into an Attofluor Cell Chamber (Invitrogen) and 900 µl fresh growth medium was added into the chamber. Thereafter, the chamber was put in the microscope and $0.1\times10^6$ effector cells resuspended in 100 µl medium were added. After letting the effector cells settle at the bottom of the chamber for 5 minutes, images were recorded with 15 sec intervals for a total of 2 hours. For incubation and analysis, a ZEISS Observer Z1 fluorescent microscope equipped with a XLmulti S1 Incubator unit was used. Image analysis and video exporting was done using the ZenPRO software.

Generation of iRFP670$^+$ A375 and A375(Tyr) Cells piRFP670-N1 (ID #45457) plasmid was purchased from Addgene. BamHI and EcoRI cut sites were implemented in primers that amplify the iRFP670 gene. After amplification, the PCR product was purified, cut with BamHI-EcoRI and cloned into LeGO backbone (after removal of GFP gene from the LeGO-G2 (ID #25917) plasmid) through the same cut sites making up LeGO-iRFP670 plasmid. Virus production was carried out as explained before. A375 and A375 (Tyr) cells were transduced with LeGO-iRFP670 overnight in the presence of 8 ug/ml Protamine Sulfate. 5 days after transduction, iRFP670+ cells were sorted by FACS. iRFP670 expression was detected in APC channel in flow cytometry experiments.

Animal Experiments iRFP670+ A375 and A375(Tyr) cells were prepared for injection at $10^6$ cells/ml in PBS. On day 0 of the experiment, $10^5$ tumor cells were injected per mouse in 100 ul PBS and 100 ul matrigel matrix (Corning) subcutaneously. Tumor formation was followed for three days after tumor injection. Effector NK-92 cells were prepared for injection at $10^7$ cells/ml in PBS with 2000 U recombinant human IL-2 per $10^7$ cells. $10^6$ effector cells were injected proxy-tumoral per mouse on days 4 and 7 post tumor injection. Intravital imaging using the Bruker Xtreme II system was performed on days 3, 6, 10 and 13 post tumor inoculation under isoflurane anesthesia.

and described in the specification. One skilled in the art will readily appreciate that the present invention is well adapted to carry out the objectives and obtain the ends and advantages mentioned, as well as those inherent therein. The modified cells, NK cells, modified NK cells, therapeutic compositions and uses, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

SEQUENCE LISTING

```
<160> NUMBER OF SEQ ID NOS: 2

<210> SEQ ID NO 1
<211> LENGTH: 9
<212> TYPE: PRT
<213> ORGANISM: human

<400> SEQUENCE: 1

Tyr Met Asp Gly Thr Met Ser Gln Val
1               5

<210> SEQ ID NO 2
<211> LENGTH: 10
<212> TYPE: PRT
<213> ORGANISM: human

<400> SEQUENCE: 2

Glu Leu Ala Gly Ile Gly Ile Leu Thr Val
1               5                   10
```

Statistical Analysis

For preparation of graphs and statistical analysis, Graph-Pad Prism (GraphPad Software Inc.) was used.

CONCLUSION

In conclusion, the instant invention presents a novel approach in immunotherapy intending to overcome the major hurdle of "mispairing" in TCR gene therapy by using NK cells as a source that have similar cytotoxic capacity as T cells but present themselves baggage-free with no endogenous TCR expression.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown

What is claimed is:

1. A modified Natural Killer (NK) cell expressing an antigen-specific functional T cell receptor (TCR) complex comprising ectopically expressed protein chains consisting of a T cell receptor (TCR) α chain, a T Cell receptor (TCR) β chain, a CD3 γ chain, a CD3 δ chain, and a CD3 ε chain, wherein said NK cell is free of an ectopically expressed CD3ζ chain.

2. The modified Natural Killer (NK) cell according to claim 1, wherein the modified Natural Killer (NK) cell is an NK-92 cell, a YTS cell, or a primary human NK cell.

3. The modified Natural Killer (NK) cell according to claim 1, wherein the antigen-specific functional T cell receptor (TCR) complex is specific for an antigen located on a cellular surface or for an intracellular antigen.

4. The modified Natural Killer (NK) cell according to claim 3, wherein the antigen is a tumor antigen, a tumor-associated antigen, a viral antigen, or a viral-associated antigen.

5. The modified Natural Killer (NK) cell according to claim 4, wherein the antigen is a melanoma-associated antigen.

6. The modified Natural Killer (NK) cell according to claim 5, wherein the melanoma-associated antigen is tyrosinase.

7. A therapeutic composition comprising the modified Natural Killer (NK) cell according to claim 1 and at least one pharmaceutically-acceptable carrier for administration of living cells.

8. A method for producing a modified Natural Killer (NK) cell expressing an antigen-specific functional T cell receptor (TCR) complex, the method comprising:
  providing a Natural Killer (NK) cell; and
  modifying the Natural Killer (NK) cell to express the antigen-specific functional T Cell receptor (TCR) complex, thereby producing the modified Natural Killer (NK) Cell;
  wherein the antigen-specific functional T cell receptor (TCR) complex comprises ectopically expressed protein chains consisting of a T cell receptor (TCR) α chain, a T Cell receptor (TCR) β chain, a CD3 γ chain, a CD3 δ chain, and a CD3 ε chain, wherein said NK cell is free of an ectopically expressed CD3ζ chain.

9. The method according to claim 8, wherein providing a Natural Killer (NK) cell includes providing a Natural Killer (NK) cell selected from the group consisting of an NK-92 cell, a YTS cell, and a primary human NK cell.

10. The method according to claim 8, wherein modifying the Natural Killer (NK) cell includes transferring sequences encoding a T cell receptor (TCR) α chain, a T Cell receptor (TCR) β chain, a CD3 γ chain, a CD3 δ chain, and a CD3 ε chain to the NK cell using one or more viral vectors.

11. The method according to claim 10, wherein the one or more viral vectors are lentiviral vectors or retroviral vectors.

12. A method for treating a disease in a subject in need thereof, the method comprising:
  providing a composition including the modified Natural Killer (NK) cell according to claim 1 and at least one pharmaceutically-acceptable carrier for administration of living cells; and
  administering the composition to the subject;
  wherein the disease is melanoma.

13. The method according to claim 12, wherein the subject is a human or an animal subject.

14. The method according to claim 12, wherein the antigen of the antigen-specific functional T cell receptor (TCR) complex is a melanoma-associated antigen.

15. The method according to claim 14, wherein the melanoma-associated antigen is tyrosinase.

16. A modified primary human Natural Killer (NK) cell expressing an antigen-specific functional T cell receptor (TCR) complex, wherein the antigen-specific functional T cell receptor (TCR) complex comprises ectopically expressed protein chains consisting of a T cell receptor (TCR) α chain, a T Cell receptor (TCR) β chain, a CD3 γ chain, a CD3 δ chain, and a CD3 ε chain, wherein said NK cell is free of an ectopically expressed CD3ζ chain and wherein the antigen of the antigen-specific functional T cell receptor (TCR) complex is an antigen derived from a tumor-associated intracellular antigen.

* * * * *